United States Patent
Haurwitz et al.

(10) Patent No.: US 9,605,246 B2
(45) Date of Patent: Mar. 28, 2017

(54) ENDORIBONUCLEASE COMPOSITIONS AND METHODS OF USE THEREOF

(71) Applicant: The Regents of the University of California, Oakland, CA (US)

(72) Inventors: Rachel E. Haurwitz, Berkeley, CA (US); Jennifer A. Doudna, Berkeley, CA (US); Blake Wiedenheft, Oakland, CA (US); Martin Jinek, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/735,383

(22) Filed: Jun. 10, 2015

(65) Prior Publication Data

US 2015/0284697 A1    Oct. 8, 2015

Related U.S. Application Data

(60) Division of application No. 13/671,120, filed on Nov. 7, 2012, now Pat. No. 9,115,348, which is a continuation-in-part of application No. PCT/US2011/035775, filed on May 9, 2011.

(60) Provisional application No. 61/333,163, filed on May 10, 2010, provisional application No. 61/365,627, filed on Jul. 19, 2010, provisional application No. 61/413,287, filed on Nov. 12, 2010.

(51) Int. Cl.
| | |
|---|---|
| *C12P 19/34* | (2006.01) |
| *C12N 9/22* | (2006.01) |
| *C07K 14/81* | (2006.01) |
| *C12Q 1/68* | (2006.01) |
| *C07K 1/22* | (2006.01) |

(52) U.S. Cl.
CPC .......... *C12N 9/22* (2013.01); *C07K 1/22* (2013.01); *C07K 14/8117* (2013.01); *C12P 19/34* (2013.01); *C12Q 1/6806* (2013.01); *C12Q 1/6816* (2013.01); *C12Q 1/6823* (2013.01)

(58) Field of Classification Search
None
See application file for complete search history.

(56) References Cited

U.S. PATENT DOCUMENTS

| | | |
|---|---|---|
| 5,034,506 A | 7/1991 | Summerton et al. |
| 5,489,677 A | 2/1996 | Sanghvi et al. |
| 5,602,240 A | 2/1997 | De Mesmaeker et al. |
| 5,874,304 A | 2/1999 | Zolotukhin et al. |
| 5,919,445 A | 7/1999 | Chao |
| 5,968,738 A | 10/1999 | Anderson et al. |
| 5,968,750 A | 10/1999 | Zolotukhin et al. |
| 5,976,796 A | 11/1999 | Szalay et al. |
| 5,985,577 A | 11/1999 | Bulinski |
| 5,990,479 A | 11/1999 | Weiss et al. |
| 6,020,192 A | 2/2000 | Muzyczka et al. |
| 6,066,476 A | 5/2000 | Tsien et al. |
| 6,207,392 B1 | 3/2001 | Weiss et al. |
| 6,251,303 B1 | 6/2001 | Bawendi et al. |
| 6,306,610 B1 | 10/2001 | Bawendi et al. |
| 6,319,426 B1 | 11/2001 | Bawendi et al. |
| 6,322,901 B1 | 11/2001 | Bawendi et al. |
| 6,423,551 B1 | 7/2002 | Weiss et al. |
| 6,426,513 B1 | 7/2002 | Bawendi et al. |
| 6,444,143 B2 | 9/2002 | Bawendi et al. |
| 6,576,291 B2 | 6/2003 | Bawendi et al. |
| 6,649,138 B2 | 11/2003 | Adams et al. |
| 6,815,064 B2 | 11/2004 | Treadway et al. |
| 7,537,912 B2 | 5/2009 | Wood et al. |
| 7,919,277 B2 | 4/2011 | Russell et al. |
| 8,361,725 B2 | 1/2013 | Russell et al. |
| 2004/0131637 A1 | 7/2004 | Chatfield |
| 2008/0124725 A1 | 5/2008 | Barrangou et al. |
| 2010/0093026 A1 | 4/2010 | Shimada et al. |
| 2011/0189776 A1 | 8/2011 | Terns et al. |
| 2011/0217739 A1 | 9/2011 | Terns et al. |
| 2011/0236530 A1 | 9/2011 | Manoury et al. |
| 2011/0300538 A1 | 12/2011 | Barrangou et al. |
| 2013/0158245 A1 | 6/2013 | Russell et al. |
| 2014/0302563 A1 | 10/2014 | Doudna et al. |

FOREIGN PATENT DOCUMENTS

| | | |
|---|---|---|
| EP | 1947177 | 7/2008 |
| WO | WO 93/03769 | 3/1993 |
| WO | WO 93/09239 | 5/1993 |
| WO | WO 93/19191 | 9/1993 |
| WO | WO 94/12649 | 6/1994 |

(Continued)

OTHER PUBLICATIONS

Adams, et al. PHENIX: a comprehensive Python-based system for macromolecular structure solution. Acta Crystallogr D Biol Crystallogr. Feb. 2010;66(Pt2):213-21. doi:10.1107/S0907444909052925. Epub Jan. 22, 2010.

(Continued)

*Primary Examiner* — Richard Hutson
(74) *Attorney, Agent, or Firm* — Bozicevic Field & Francis, LLP; Paula A. Borden

(57) ABSTRACT

The present disclosure provides variant Csy4 endoribonucleases, nucleic acids encoding the variant Csy4 endoribonucleases, and host cells genetically modified with the nucleic acids. The variant Csy4 endoribonucleases find use in a variety of applications, which are also provided. The present disclosure also provides methods of detecting a specific sequence in a target polyribonucleotide; and methods of regulating production of a target RNA in a eukaryotic cell.

14 Claims, 38 Drawing Sheets

(56) References Cited

FOREIGN PATENT DOCUMENTS

| WO | WO 94/28938 | 12/1994 |
|---|---|---|
| WO | WO 95/00655 | 1/1995 |
| WO | WO 95/11984 | 5/1995 |
| WO | WO 96/17951 | 6/1996 |
| WO | WO 2006/123537 | 11/2006 |
| WO | WO 2007/025097 | 3/2007 |
| WO | WO 2010/011961 | 1/2010 |
| WO | WO 2010/054108 | 5/2010 |
| WO | WO 2011/143124 | 11/2011 |
| WO | WO 2012/164565 | 12/2012 |
| WO | WO 2013/088446 | 6/2013 |
| WO | WO 2013/098244 | 7/2013 |
| WO | WO 2013/141680 | 9/2013 |
| WO | WO 2013/142578 | 9/2013 |

OTHER PUBLICATIONS

Ali, et al. Adeno-associated virus gene transfer to mouse retina. Hum Gen Ther. Jan. 1, 1998;9(1):81-6.

Ali, et al. Gene transfer into the mouse retina mediated by an adeno-associated viral vector. Hum Mol GEnet. May 1996 ; 5(5):591-4.

Altschul, et al. Gapped BLAST and PSI-BLAST: a new generation of protein database search programs. Nucleic Acids Res. Sep. 1, 1997;25(17):3389-402.

Amantana, et al. Pharmacokinetics, biodistribution, stability and toxicity of a cell-penetrating peptide-morpholino oligomer conjugate. Bioconjug Che. Jul.-Aug. 2007;18(4)1325-31. Epub Jun. 21, 2007.

Barrangou, R. RNA-mediated programmable DNA cleavage. Nat Biotehcnol. Sep. 2012;30(9):836-8. doi:10.1038/nbt.2357.

Beloglazova, et al. A novel family of sequence-specific endoribonucleases associated with the clustered regularly interspaced short palindromic repeats. J Biol Chem. Jul. 18, 2008;283(29):20361-71. doi: 10.1074/jbc.M803225200. Epub May 15, 2008.

Bennett et al. Real-time, noninvasive in vivo assessment of adeno-associated virus-mediated retinal transduction. Invest Opthalmol Vis Sci. Dec. 1997;38(13):2857-63.

Bhaya, et al. CRISPR-Cas systems in bacteria and archaea: versatile small RNAs for adaptive defence and regulation. Annu Rev. Genet. 2001;45:273-97. doi: 10/1146/annurev-genet-110410-132430.

Borras, et al. Adenoviral reporter gene transfer to the human trabecular meshwork does not alter agueous humor outflow. Relevance for potential gene therapy of glaucoma. Gene Ther. Apr. 1999;6(4):515-24.

Branchini, et al. 2Red-emittingn luciferases for bioluminescence reporter and imaging applications. Anal Biochem. Jan. 15, 2010;396(2):290-7. doi: 10/1016/j.ab.2009.09.009. Epub Sep. 11, 2009.

Brouns, et al. Small CRISPER RNAs guide antiviral defense in prokaryotes. Science. Aug. 15, 2008;321(5891):960-04. doi: 10.1126/science. 1159689.

Busso, et al. Construction of a set Gateway-based destination vectors for high-throughput cloning and expression screening in *Escherichia col*. Anal Biochem. Aug. 15, 2005, 343(2):313-21.

Cai, et al. Solution structure of P22 transcriptional antitermination N peptide-boxB RNA complex. Nat Struct Biol. Mar. 1998;5(3):203-12.

Camarero, et al. Synthesis of proteins by native chemical ligation using Fmoc-based chemistry. Protein Pept. Lett. Nov. 2005; 12(8):723-8.

Carr, et al. Genome engineering. Nat Biotechnol. Dec. 2009;27(12)1151-62. doi:10.1038/nbt.1590.

Carrier, et al. Expression of human IL-1 beta in *Salmonella typhimurium*. A model system for the delivery of recombinant therapeutic proteins in vivo. J Immunol. Feb. 15, 1992;148(4):1176-81.

Carte, et al. Cas6 is an endoribonuclease that generates guide RNAs for invader defense in prokaryotes. Genes Dev. Dec. 15, 2008;22(24):3489-96. doi:10/1101/gad.1742908.

Carte, et al. "Binding and cleavage of CRIPSR RNA by Cas6", RNA: 2010; 16(11):2181-2188.

Chatfield, et al. Use of the nirB promoter to direct the stable expression of heterologous antigens in *Salmonella* oral vaccine strains: development of a single-dose oral tetanus vaccine. Biotechnology (N Y). Aug. 1992; 10(8):888-92.

Chylinski, et al. The tracrRNA and Cas9 families of type II CRIPSR-Cas immunity systems. RNA Biol. May 2013;10(5):726-737 doi:10.4161/rna.24321. Epub Apr. 5, 2013.

Cong, et al. multiplex genome engineering using CRISPER/Cas systems. Science. Feb. 15, 2013, 339(6121):819-23. doi:10.1126/science.1231143. Epub Jan. 3, 2013.

Co-pending U.S. Appl. No. 14/403,413, filed Nov. 24, 2014.

De Boer, et al. The tac promoter: a functional hybrid derived from the trp and lac promoters. Proc Natl Acad Sci USA. Jan. 1983;80(2):21-5.

Dunstan, et al. Use of in vivo-regulated promoters to deliver antigens from attenuated *Salmonella enteric* avar. Typhimurium. Infect Immun. Oct. 1999; 62(10)5133-41.

Ebihara, et al. Crystal structure of hypothetical protein TTHB192 from Thermus thermophilus HB8 reveals a new protein family with an RNA recognition motif-like domain. Protein Sci. Jun. 2006; 15(6):1494-9. Epub May 2, 2006.

Emsley, et al. Coot: model-building tools for moelcular graphics. Acta Crystallogr D Biol Crystsallogr. Dec. 2004; 60( Pt 12 Pt 1): 2126-32. Epub Nov. 26, 2004.

Estarellas, et al. Molecular dynamic simulations of protein/RNA complexes: CRIPSR/Csy4 endoribonuclease, Biochim. Biophys. Acta (2013), http://dx.doi.org/10.1016/j.bbagen.2014.10.021.

European Search Report and Search Opinion dated Feb. 7, 2014 for EP Application No. 11781086.1.

Flannery, et al. Efficient photoreceptor-targeted gene expression in vivo by recombinant adeno-associated virus vector. Proc Natl Acad Sci USA. Nov. 15, 1993;90(22):1061307.

Flotte, et al. Stable in vivo expression of the cystic fibrosis tansmembrane conductance regulator with an adeno-associated virus vector. Proc Natl Acad Sci USA. Nov. 15, 1993;90(22):10613-7.

Ganesan. Solid-phase synthesis in the twenty-first century. Mini Rev Med Chem. Jan. 2006;6(1):3-10.

GenBank Accession No. EAZ52875.1 Feb. 25, 2008.

GenBank Direct Submission M33159.1. T. thermophiles insertion sequences Is1000A and Is1000B. May 5, 1993. [Retrieved from the internet Oct. 24, 2013: http://www.ncbi.nim.nih.gov/nuccore/M33159] (nucleotides 6325-6290).

Grissa, et al. The CRISPRdb database and tools to display CRISPRs and to generate dictionaries of spacers sand repeats. BMC Bioinformatics. May 23, 2007; 8:172.

Grosse-Kunstleve, et al. Substructure search procedures for macromolecular structures. Acta Crystallogr D Biol Crystallogr. Nov. 2003;59(Pt 11):1996-73. Epub Oct. 23, 2003.

Haft, et al. A guild of 45 CRISPR-associated (Cas) protein families and multiple CRISPR/Cas subtypes exist in prokaryotic genomes. PLoS Comput Biol. 2005 No; 1(6):e60. Epub Nov. 11, 2005.

Hale, et al. RNA-guided RNA cleavage by a CRISPR RNA-Cas protein complex. Cell Nov. 25, 2009; 139(5):945-56. doi:10.1016/j.cell.2009.07.040.

Harborne, et al. Transcriptional control, translation and function of the products of the five open reading frames of the *Escherichia coli* nir operon. Mol Microbiol. Oct. 1992;6(19):2805-13.

Haurwitz, et al. Sequence- and structure-specific RNA processing by a CRISPR endonuclease. Science. Sep. 10, 2010;329(599)1355-8. doi: 10.1126/science.1192272.

Haurwitz, et al. Csy4 relies on an unusual catalytic dyad to position and cleave CRISPR RNA. EMBO J Epub Apr. 20, 2012, 31(12):2824-32.

Heasman, Morpholino oligos: making sense of antisense? Dev Biol. Mar. 15, 2002; 243(2):209-14.

Holm, et al. Protein structure comparison by alignment of distance matrices. J Mo. Bio. Sep. 5, 1993;233(1):123-38.

(56) References Cited

OTHER PUBLICATIONS

Horvath, et al. CRISPR/Cas, the immune system of bacteria and archaea. Science. Jan. 8, 2010;327(5962)167-70. doi:10.1126/science.1179555.
Hudziak, et al. Resistance of morpholino phosphorodiamidate oligomers to enzymatic degradation. ANtisense Nucleic Acid Drug Dev. 1996 Winter; 6(4):267-72.
Huppler, et al. Metal binding and base ionization in the U6 RNA intramolecular stem-loop structure. Nat Struct Biol. Jun. 2002;9(6):431-5.
International search report and written opinion dated Feb. 17, 2012 for PCT/US2001/035775.
International search report and written opinion dated Jan. 18, 2014 for PCT/US2013/045602.
International search report and written opinion dated Mar. 7, 2013 for PCT Application No. PCT/EP2012/076674.
International search report dated Mar. 11, 2014 for PCT Application No. PCT/US2013/053287.
Jansen, et al. Identification of genes that are associated with DNA repeats in prokaryotes. Mol. Microbiol.
Jinek, et al. A programmable dual-RNA endonuclease in adaptive bacterial immunity. Science. Aug. 17, 2012;337(6096):816-21. doi: 10/1126/science.1225829. Epub Jun. 28, 2012.
Jinek et al. RNA-programmed genome editing in human cells. Elife. 2013;2:e00471. doi:10.7554/eLife.00471. Epub Jun. 28, 2013.
Jomary, et al. Rescue of photoreceptor functoin by AAV-mediated gene transfer in mouse model of inherited reitnal degeneration. Gene Ther. Jul. 1997;4(7):683-90.
Kabsch. XDS. Acta Crystallogr D Biol Cyrstallogr. Feb. 2010;66(Pt 2):125-32. doi: 10.1107/S0907444909047337. Epub Jan. 22, 2010.
Kunin, et al. Evolutionary conservation of sequence and secondary structures in CRISPR repeats. Genome Biol. 2007;8(4):R61.
Lee, et al. RNA-protein analysis using a conditional CRISPR nuclease. Proc Natl Acad Sci USA. Apr. 2, 2013, 110(14):5416-21.
Legault, et al. NMR structure of the bacteriophage lambda N peptide/boxB RNA complex: recognition of GNRA fold by an arginine-rich motif. Cell. Apr. 17, 19987; 93 (2):289-99.
Li, et al. In vivo transfer of a reporter gene to the retina mediated by an adenoviral vector. Invest Opthalmol Vis Sci. Apr. 1994;35(5):254309.
Li, et al. Phentoype correction in retinal pigment epithelium in murine mucopolysaccharidosis VII by adenovirus-mediated gene transfer. Proc Natl Acad Sci USA Aug. 15, 1995;92(17):7700-4.
Lillestol, et al. A putative viral defense mechanism in archaeal cells. Archaea. Aug. 2006;2(1):59-72.
Lillestol, et al. CRISPR families of the crenarchaeal genus *Sulfolobus*: bidirectional transcription and dynamic properties. Mol Microbiol. Apr. 2009;72(1):259-72. Doi: 10.1111/j.1365-2958.2009.06641.x.Epub Feb. 23, 2009.
Makaraova, et al. evolution and classification of the CRISPR-Cas systems. Nat Rev Microbiol. Jun. 2011;9(6):467-77. Doi:10.1038/nrmicro2577. Epub May 9, 2011.
Mali, et al. RNA-guided human genome engineering via Cas9. Science. Feb. 14, 2013;339(6121):823-6. Doi: 10.1126/science.1232033. Epub Jan. 3, 2013.
Marraffini, et al. CRISPR interference: RNA-directed adaptive immunity in bacteria and archaea. Nat Rev Genet. Mar. 2010;11(3):181-90. Doi:10.1038/nrg2749.
Matz, et al. Fluroescent proteins from nonbioluminescent *Anthoza* species. Nat biotechnol. Oct. 1999;17(10):969-73.
McCoy, et al. Phaser crystallographic software. J Appl Crystallogr. Aug. 1, 2007;40(Pt 4):658-674. Epub Jul. 13, 2007.
McKelvie, et al. Expression of heterologous antigens in *Salmonella typhimurium* vaccine vectors using the in vivo-inducible, SPI-2 promoter, ssaG. Vaccine. Sep. 3, 2004;22(24-26):3243-55.
Melton, et al. Efficient in vitro synthesis of biologically active RNA and RNA hybridization probes from plasmids containing a bacteriophage SP6 promoter. Nucleic Acids Res. Sep. 25, 1984;12(18):7035-56.

Mendelson, et al. Expressoin and rescue of a nonselected marker from an integrated AAV vector. Virology. Sep. 1998; 166(1) 154-65.
Merriefield, et al. Solid phase peptide synthesis. I. The synthesis of a tetrapeptide 1963; 85;2149-2156.
Mezzanotte, et al. In vivo bioluminescence imaging of murine xenograft cancer models with a red-shifter thermostable luciferase. Mol Imaging Biol. Aug. 2010; 12(4)406-14. Doi:10.1007/s11307-009-0291-3. Epub Nov. 25, 2009.
Miyoshi, et al. Stable and efficient gene transfer into the retina using an HIV-based lentiviral vector. Proc Natl Acad Sci USA. Sep. 16, 1997;94 (19):10319-626.
Morcos, et al. Vivo-Morpholinos: A non-peptide transported delivers morpholinos into a wide array of mouse tissues. BioTechniques. 2008I 45:616-626.
Ngo, et al. In the Protein Folding Problem and Tertiary Structure Prediction, 1994, Merz et al. (ed.), Birkhauser, Boston, MA. pp. 433 and 492-495.
Partridge, et al. A simple method for delivering morpholino antisense oligos into the cytoplasm of cells. Antisense Nucleic Acid Drug Dev. 1996 Fall;6(3):169-75.
Patent Examination Report No. 1, Australia Patent Application No. 2011253222, mailed Aug. 13, 2013, 3 pages.
Rolling, et al. Evaluation of adeno-associated vius-mediated gene transfer into the rat retina by clinical fluorescence photography. Hum Gene. Ther. Mar. 1, 1999; 10(4):641-8.
Sakamoto, et al. A virectomy improves the transfection efficiency of adenoviral vector-mediated gene transfer to Muller cells. Gene Ther. Aug. 1998;5(8):1088-97.
Samulski, et al. Helper-free stocks of recombinant adeno-associated viruses: normal integration does not require viral gene expression. J Virol. Sep. 1989; 63(9):3822-8.
SBI. Precisionx Cas9 SmartNuclease vector system user manual. System Biosciences. 2013.
Sizemore, et al. Attenuated Shigella as a DNA delivery vehicle for DNA-mediated immunization. Science. Oct. 13, 1995;270(5234):299-302.
Sorek, et al. CRISPR—a widespread system that provides acquired resistance against phages in bacteria and archaea. Nat Rev. Microbiol. Mar. 2008;6(3):181-6.
Sternberg, et al. Mechanism of substrate selection by a highly specific CRISPR endoribonuclease. RNA (Apr. 2012), 18(4):661-72.
Summerton, et al. Morpholino antisense oligomers: design, preparation, and properties. Antisense Nucleic Acid Drug Dev. Jun. 1997; 7(3):187-95.
Summerton. Morpholino antisense oligomers: the case for an RNase H-independent structural type. Biochim Biophys Acta. Dec. 1999 10.1489 (1):141-58.
Takahashi, et al. Rescue from photoreceptor degeneration in the rd mouse by human immunodeficiency virus vector-mediated gene transfer. J. Virol Sep. 1999;73(9):7812-6.
Tang, et al. Identification of 86 candidates for small non-messenger RNAs from the archaeon Archaeoglobus fulgidus. Proc Natl Acad Sci USA. May 28, 2002;99(11):7536-41.
Tang, et al. Identification of novel non-coding RNAs as potential antisense regulators in the archaeon Sulfolobus solfataricus. Mol Microbiol. Jan. 2005;55(2):469-81.
Terns, et al. CRISPR-based adaptive immune systems. Curr Opin Microbiol. Jun. 2011;14(3):321-7. Doi:10.1016/j.mib.2011.03.005. Epub Apr. 29, 2011.
Terwilliger, et al. Iterative model building, structure refinement and density modification with the PHENIX AutoBuild wizard. Acta Crystallogr D Biol Crystallogr. Jan. 2008;64(Pt 1):61-9. Epub Dec. 5, 2007.
UniProt Direct Submission D7BB61_MEISD. CRISPR-associated protein Cas6. May 16, 2012. [Retrieved from the Internet Oct. 24, 2013: http://www.uniprot.org/uniproUD7BB61.txt?version+9 ]; in entirety.
Valdivia, et al. Bacterial genetics by flow cytometry: rapid isolation of *Salmonella typhimurium* acid-inducible promoters by differential fluorescence induction. Mol Microbiol. Oct. 1996;22(2):367-78.

(56) References Cited

OTHER PUBLICATIONS

Van Der Oost, et al. CRIPSR-based adaptive and heritable immunity in prokaryotes. Trends Biochem Sci. Aug. 2009;34(8):401-7. Doi:10.1016/j.tibs.2009.05.002. Epub Jul. 29, 2009.
Vonrhein, et al. Automated structure solution with autoSHARP. Methods Mol Biol. 2007;364:215-30.
Wiedenheft, et al. RNA-guided genetic silencing systems in bacteria and archaea. Nature. Feb. 15, 2012,482(7385):331-8. Doi:10.1038/nature10886.
Yen, et al. Exogenous control of mammalian gene expression through modulation of RNA self-cleavage. Nature; 431:471-6. Sep. 23, 2004 (Sep. 23, 2004). Entire document.
Young. An improved method for the detection of peroxidase-conjugated antibodies on immunoblots. J. Virol Methods. Apr.-May 1989;24(1-2):227-35.

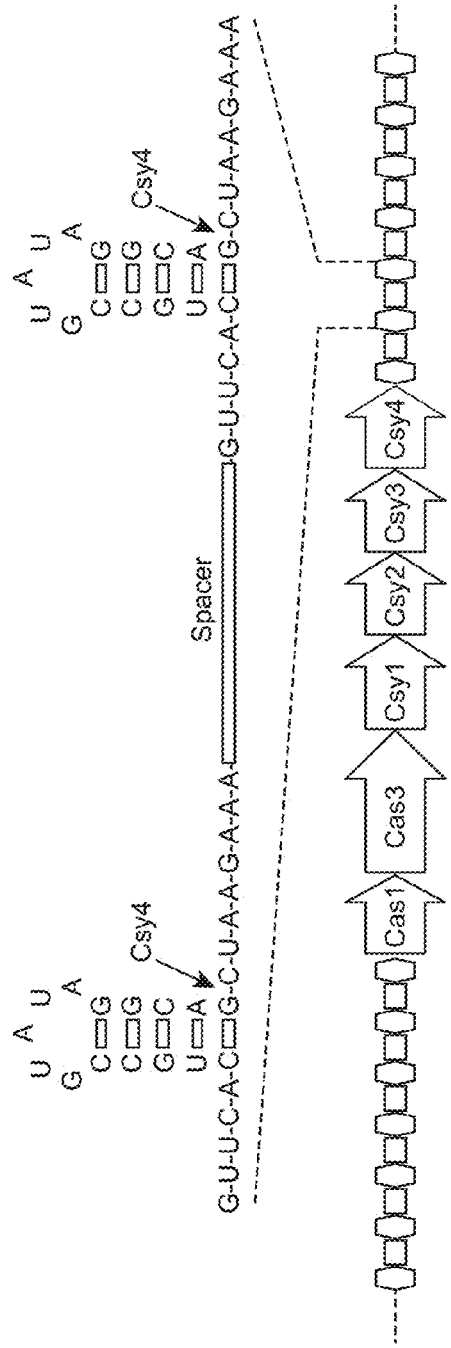
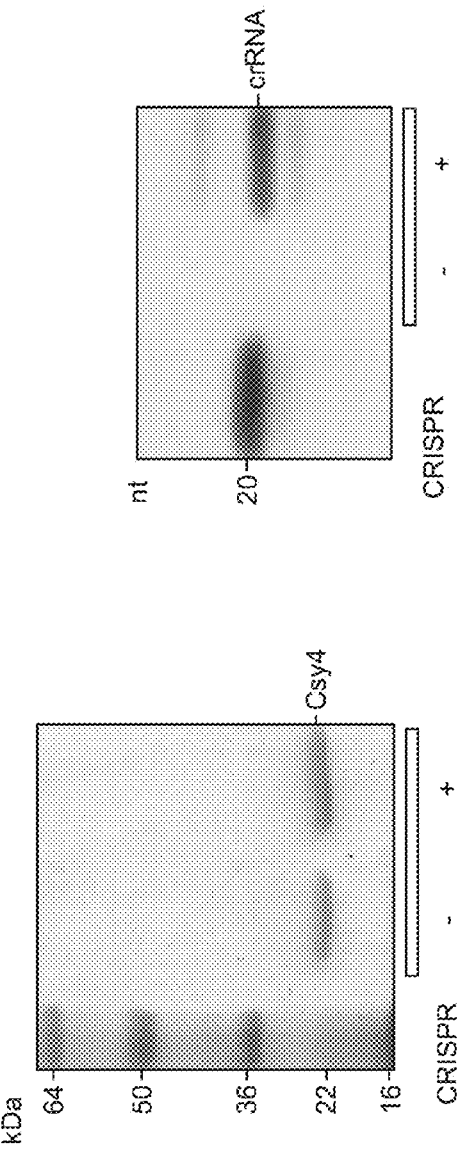
FIG. 1A
FIG. 1B
FIG. 1C

FIG. 5A

Csy4 sequence
>gi|116650369|ref|YP_790814.1| hypothetical protein PA14_33300 [Pseudomonas aeruginosa UCBPP-PA14]
MSVLFGKLHQALVAQGDRIGVSFPDLDESRSLGERLRIHASADDLRALLARPWLEGLRDHLQFGEPAVVPHPTPYRQVSRVQAKSNPERLRRLMRRH
DLSEEEARKRIPDTVARALDLPFVTLRSQSTGQHFRLFIRHGPLQVTAEEGGFTCYGLSKGGFVPWF (SEQ ID NO:5)

RNA recognition sequence
GUUCACUGCCGUAUAGGCAGCUAAGAAA (SEQ ID NO:1)

FIG. 5B

Csy4 sequence
>gi|107101871|ref|ZP_01365789.1| hypothetical protein PaerPA_01002916 [Pseudomonas aeruginosa PACS2]
MDHYLDIRLRLPDPEFPPAQLMSVLFGKLHQALVAQGDRIGVSFPDLDESRSRLGERLRIHASADDLRALLARPWLEGLRDHLQFGEPAVVPHPTPYRQVSRVQVKSN
PERLRRLMRRHDLSEEEARKRIPDTVARTLD
LPFVTLRSQSTGQHFRLFIRHGPLQVTAEEGGFTCYGLSKGGFVPWF
(SEQ ID NO:6)

RNA recognition sequences
GUUCACUGCCGUGUAGGCAGCUAAGAAA (SEQ ID NO:7)
GUUCACUGCCGUAUAGGCAGCUAAGAAA (SEQ ID NO:1)

FIG. 5C

>gi|254235433|ref|ZP_04928756.1| hypothetical protein PACG_01340 [Pseudomonas aeruginosa C3719]
MDHYLDIRLRLPDPEFPPAQLMSVLFGKLHQALVAQGDRIGVSFPDLDESRSRLGERLRIHASADDLRAL
LARPWLEGLRDHLQFGEPAVVPHPTPYRQVSRVQAKSNPERLRRLMRRHDLSEEEARKRIPDTVARTLD
LPFVTLRSQSTGQHFRLFIRHGPLQVTAEEGGFTCYGLSKGGFVPWF
(SEQ ID NO:8)

RNA recognition sequences
GUUCACUGCCGUGUAGGCAGCUAAGAAA (SEQ ID NO:7)
GUUCACUGCCGUAUAGGCAGCUAAGAAA (SEQ ID NO:1)

FIG. 5D

>gi|254240857|ref|ZP_04934179.1| hypothetical protein PA2G_01531 [Pseudomonas aeruginosa 2192]
MDHYLDIRLRLPDPEFPPAQLMSVLFGKLHQALVAQGDRIGVSFPDLDESRSRLGERLRIHASADDLRAL
LARPWLEGLRDHLQFGEAVVPHFTPYRQVSRVQAKSNPERLRRLMRRHDLSEEEARKRIPDTVARTLD
LPFVTLRSQSTGQHFRLFIRHGPLQATAEEGGFTCYGLSKGGFVPWF (SEQ ID NO:9)

RNA recognition sequences
GUUCACUGCCGUGUAGGCAGCUAAGAAA (SEQ ID NO:7)
GUUCACUGCCGUAUAGGCAGCUAAGAAA (SEQ ID NO:1)

FIG. 5E

>gi|242238181|ref|YP_002986362.1| CRISPR-associated protein, Csy4 family [Dickeya dadantii Ech703]
MDHYIEIRVLPDLEFSAVQLISALFAKLHRALGQRATGAIGVSFPDVDKTLGERLRLHGSVQEFAALEQT
GWLKGLRDYTAIIEPLPVFAGAKKHRTVRRVQVKSSAERLRRRAVSKGRMTEDEAATRIPYAVEKRSSLPY
LPIRSLSSGQTFLLFVEHGPLQDKPVAGAFSSYGLSATTTIPWF (SEQ ID NO:10)

RNA recognition sequences
GUUCACUGCCGUAGGCAGCAGCUAGAAA (SEQ ID NO:11)
GUUCACUGCCGAGUAGGCAGCUAGAAA (SEQ ID NO:12)

FIG. 5F

>gi|261822890|ref|YP_003260996.1| CRISPR-associated protein, Csy4 family [Pectobacterium wasabiae WPP163]
MDHYIDIRVQPDPEFTAPQLINALFAKLHERALGQLADGKIGISFPEVGKTLGECLRLHGTADALSTLEKT
GWLKGLRDYIQVSECKAVPNNVKFRTVRRVQLKTSAERLRRSVNKGWLTEAEAAARIPDAVEKRSTLPF
VQIRSLSNGQMFFVEVEHGPLQNAPATGRFSSYGLSARATVPWF (SEQ ID NO:13)

RNA recognition sequence
GUUCACUGCCGUAUGCAGCAGCUAGAAA (SEQ ID NO:14)

FIG. 5G

>gi|253990195|ref|YP_003041551.1| hypothetical protein PAU_02718 [Photorhabdus asymbiotica subsp. asymbiotica ATCC_43949] MDYYFEILVLPDPEFPSKQSLMEALFAKLHRALGQVGNGRIGVSFPCARKTLGDKLRIHGASEALNDLQAL
PWLKGLRDYTEIMDIQPVPQDTQYRRVSRVQVKSASAERLRRSIKKGWLTEEQARQRIPISKEQRTHLPF
LLVKSLSSQTFPLFIEQGPIEDKPTPGVFSSYGLSASATIPWF (SEQ ID NO:15)

RNA recognition sequences
GUUCACUGCCGUACAGGCAGCUUAGAAAA (SEQ ID NO:16)
GUUCACUGCCGUACAGGCAGCUAGAAAA (SEQ ID NO:17)
ACUGCCCGUACAGGCAGUUAGAAA (SEQ ID NO:18)
GUUCACUGCCGUACAGGCAGCUAGAAA (SEQ ID NO:19)
GGGUACUGCCGUACAGGCAGCUAGAAA (SEQ ID NO:20)
GUUCACUGCCGUACAGGCAGCUUAGAAA (SEQ ID NO:21)

FIG. 5H

\>gi|307132482|ref|YP_003884498.1| hypothetical protein Dda3937_03453 [Dickeya dadantii 3937]
MDHYIEIRVLPDPEFSGVQLLSALFAKLHRALGORATGAIGVSFPDAGKTLGERLRLEGSVQELAALEQT
GWLRGLRDYTAITEPLPVPAGVKHRTVRRVQVKSSAERLRRRAVNKGRMTVDEADARIPYTVEKRTSLPY
LPLRSLSNGQTFLLFVEHGPLQDKPVAGAFSSYGLSAVATIPWF (SEQ ID NO:22)

RNA recognition sequences
GUUCACUGCCGUAGGCAGCUUAGAAA (SEQ ID NO:23)
GUUCACUGCGAGUAGGCAGCUUAGAAA (SEQ ID NO:12)

FIG. 5I

\>gi|285019813|ref|YP_003377524.1| CRISPR-associated protein, csy4 family [Xanthomonas albilineans GPE PC73]
MQHYIDLIHLRPDPELAPYQLLGALYARLHRSLVTLNTTRIGVSFPGHDNRVPTLGTHLRLHGDDSTIHHL
MATTWLRGVRDHVTITSIGAVPSEAVHRQVTRVQAKSSPERLRRRAMRRHGISEDLAVQRIPDSAAEQLR
LPFVVLGSRSTGQTAPPVFVRHGPVQQEFVPGDFSSYGLSRGATVPWF (SEQ ID NO:24)

RNA recognition sequences
GUUCACUGCCGUAGGCAGCCAGCAGAAA (SEQ ID NO:25)
UUCACUGCCGUAGGCAGCCAGCAGAAA (SEQ ID NO:26)
GUUCACUGCCGUAUAGGCAGCUCAGAAA (SEQ ID NO:27)

FIG. 5J

\>gi|501122605|ref|YP_051772.1| hypothetical protein ECA3684 [Pectobacterium atrosepticum SCRI1043]
MDHYIDIRVQPDPEFTASQLLNALFAKLHRVLGQLANGKIGISFPEVGKTLGECLRLHGEDALSTLEKT
SWLKGLRDYTQVSECKVVPNGVKFRTVRRVQLKSSAERLRRSVSKGWLTAAEAAARIPDAVEKRSALFF
VQIKSLSNGQMFFVFVEHGPLQNAPTAGRFSSYGLSTREATVPWF (SEQ ID NO:28)

RNA recognition sequence
GUUCACUGCCGUACAGGCAGCUUAGAAA (SEQ ID NO:21)

FIG. 5K

\>gi|37525730|ref|NP_929074.1| hypothetical protein plu1796 [Photorhabdus luminescens subsp. laumondii TT01]
MDYYLEIRVLPDLEFSQQSLFEAIFAKLHRALGQLSNGQVGVSFPCARRTLGDTLRIHGSSEAINDLQAL
PWLKGLRDYTEVIDIQPIPQETKYRCVSRVQVKSSAERLRRAIKKGWLTGRQARQRIPISKRQRTHLPF
LFIKSLSSGQSFLLFVKQGPIQDKPTSGIFSSYGLSSSATIPWF (SEQ ID NO:29)

RNA recognition sequences
GUGCACUGCCGUACAGGCAGCUUAGAAA (SEQ ID NO:17)
GUUCACUCCCGUACAGGCAGCUUAGAAA (SEQ ID NO:21)

FIG. 5L

>gi|297569494|ref|YP_003690838.1| CRISPR-associated protein, Csy4 family [Desulfurivibrio alkaliphilus AHT2]
MVMAMDCYVEISLLPDEFPDSILMNALFAKLHRALAENGKQEIGVSFPEFGKKINSKLRIHGSEESLKR
LMDLNWIQGMKDYTRVSGIAKVPDSCQYRFVKRVQAKSSVDRLYRRSVKKGWLSEENAEQQKERAREGRL
KLPFVQLKSQTTGQQFRLFIQHGSLQEKPVTGRFSSYGLSNEATVPWF (SEQ ID NO:30)

RNA recognition sequence
GUUCACUGCCGCACAGGCAGCUCAGAAA (SEQ ID NO:31)

FIG. 5M

>gi|251788340|ref|YP_003003061.1| Csy4 family CRISPR-associated protein [Dickeya zeae Ech1591]
MDHYIEIRVLPDLEFSAVQLLSALFAKLHRALGQAHGAIGVSFPDVGKTLGERLRLHGSRGALHALEQT
GWRTGLRDYSTITDVLTVFTGAQYRTVRRVQVKSSAERLRRAVSKGWLTADEAAARIPYAVEKRTSLPY
LPLRSLSSGQPFLLFVEHGPLQDKPVAGTFSSYGLSATATIPWF (SEQ ID NO:32)

RNA recognition sequences
GUUCACUGCCGUGUAGGCAGCUUAGAAA (SEQ ID NO:23)
GUGCACUGCCGUAUAGGCAGCUUAGAAA (SEQ ID NO:33)

FIG. 5N

>gi|221255621|ref|NP_669044.1| hypothetical protein y1727 [Yersinia pestis KIM 10]
MDHYLDIRVLPDPEFSAQTHLEALFAKLHRALVATIPGRVGVSFPTAGKTLGSQLRLHGSRGDLLELQSA
GWLKGLQDYCECSETLPVPADVKHRTIRRVQVKSSAQRLRRSVSKGWLTEEQARLRIPDSHDKRCDLPF
LRLKSRSSEQYFLLFIEQGTLQASATTGEFSAYGLSVNATIPWF (SEQ ID NO:34)

RNA recognition sequences
GUUCACUGCCGCACAGGCAGCUUAGAAA (SEQ ID NO:19)
UGUUCACUGCCCACAGGCAGCUUAGAAAA (SEQ ID NO:35)

FIG. 5O

>gi|271501952|ref|YP_003334978.1| Csy4 family CRISPR-associated protein [Dickeya dadantii Ech586]
MDHYIEIRVLPDPEFSAVQLLSALFAKLHRALGQRATGDIGVSFPDAGKTLGERLRLHGSVQALAALEQT
GWLKGLRDYSTITDVLTVFTCAQYRTVKRVQVKSSAERLRRRAVSKGRMTADEAAARIPYAAEKRTSLPY
LPLRSLSSGQTFLLFVEHGPLQEKPVAGVFSSYGLSATATIPWF (SEQ ID NO:36)

RNA recognition sequences
GUGAACUGCCGCAUAGGCAGCUUAGAAA (SEQ ID NO:37)
GUUCACUGCCGAGUAGGCAGCUUAGAAA (SEQ ID NO:12)

FIG. 5P

>gi|111176230067|ref|YP_851980.1| hypothetical protein APECO1_1206 [Escherichia coli APEC O1]
MAVSLVRNRNKELPMDHYLEIRVLPDPEFSSEMLMAALFAKLHRVLGARGQGDIGVSFPDVNVMPGARLR
LHGSAQALQALEASTWRKGLHDYCQCSPVTPVPEIKGWRVVSRVQVKSNPQRLLRKSVKKGWLTEEQAIE
RLATQAEQRTDLPFTNMKSLSSQQLFKLFIRHGDLLKEPVKGEFSSYGLSATATIPWF (SEQ ID NO:38)

RNA recognition sequence
GUUCACUGCCGUACAGGCAGCUUAGAAA (SEQ ID NO:21)

FIG. 5Q

>gi|91209927|ref|YP_539913.1| hypothetical protein UTI89_C0896 [Escherichia coli UTI89]
MDHYLEIRVLPDPEFSSEMIMAALFAKLHRVLGARGQGDIGVSFPDVNVMPGARLRLHGSAQALQALEAS
TWRKGLTDYCQCSPVTPVPEIKGMRVVSRVQVKSNPQRLLRRSVKKGWLTEEQAIERLATQAEQRTDLPF
LNMKSLSSQQLFKLFIRHGDLLKEFVKGEFSSYGLSATATIPWF (SEQ ID NO:39)

RNA recognition sequence
GUUCACUGCCGUACAGGCAGCUUAGAAA (SEQ ID NO:21)

FIG. 5R

>gi|123780812|ref|YP_002892564.1| CRISPR-associated protein, Csy4 family [Tolumonas auensis DSM 9187]
MDHVLDIRLLPEEPEVSESFLNALFAKLHVRLGQAQGRVGVSFPDHHKRLGDLLRLHGQRTDLQAIMA
DDWLQGLKGYTQCSEVLPIPATVSYRAVKRVQAKSAHNKRQRSIAKGWLTESEAQIRIPDFQQKELHLPF
VQLKSRSNGQMMRVYVEHGPVLAVPVSGYFNAYGLSSIATIPWF (SEQ ID NO:40)

RNA recognition sequence
CUUCACUGCCGCACAGGCAGCUUAGAAA (SEQ ID NO:41)

FIG. 5S

>gi|259907505|ref|YP_002647861.1| CRISPR-associated protein Csy4 [Erwinia pyrifoliae Ep1/96]
MDHYQDIRVRVDEENGEAVLLAQVFMHLHQVLMRAANGRIGISFPNVKRTLGDRIPLHGTLDDLSALQQS
GWNKCLRDYIACSDIAPVPKGAAWRTVRRVQVKSSAERLRRSVNKGWLSEQEAAERISVLNEQRSNLPF
LQIKSGSNGQAWRLFIEHGSIVSAPSDGSFSSYGLSAAATIPWF (SEQ ID NO:42)

RNA recognition sequences
GUUCACUGCCGCACAGGCAGCUUAGAAA (SEQ ID NO:19)
UUCACUGCCGUACAGGCAGCUUAGAAAA (SEQ ID NO:43)

FIG. 5T

>gi|218688670|ref|YP_002396882.1| hypothetical protein ECED1_0855 [Escherichia coli ED1a]
MAVSIVRNRNKELPMDHYLETRVLPDPEFSSEMLMAALFAKLHRVLGARGQGDIGVSFPDVNVMPGTHLR
LHGSAQALQELEASTWRKGLTDYCQCSPVTPVPEIKGWRVVSRVQVKSNPQRLLRRSVKKGWLTEEQAIE
RLATQAEQRTDLPFLNMKSLSSQQQFKLFIRHGDLLKEPVKGEFSSYGLSATATIPWF (SEQ ID NO:44)

RNA recognition sequence
GUUCACUGCCGUACAGGCAGCUUAGAAA (SEQ ID NO:21)

FIG. 5U

>gi|121603426|ref|YP_996233.1| CRISPR-associated Csy4 family protein [Verminephrobacter eiseniae EF01-2]
MSTHYIDITLRPDPEFSPAHLNALHAQLHLALVQLGTGDVCVSFPGFILRGEHSHLGTFLRLHGATSAI
QRLQALSWLRGMRDHVKTSEVAPVPTEFTQHRVVRRVQAKSSPERSRRRIMPRLEIDEAQALQRIPDQHGR
RLALPYLRLQSASKGQVFRLFTERGPLLDTPSFGSFGTYGLSTQATIPWF (SEQ ID NO:45)

RNA recognition sequences
GUUCACUGCCGAUAGGCAGCUCAGAAA (SEQ ID NO:46)

FIG. 5V

>gi|34497206|ref|NP_901421.1| hypothetical protein CV_1751 [Chromobacterium violaceum ATCC 12472]
MDHYLDIRLLPDADFGPPVIMNALYAKLHRALAAQQRDIGVSFPGYDPAPSSHDGKPLPPTLGLTLRLH
GSAAALDGLMARRWLSGFADHAIVGDIRPVPAGASAVSVRRQAKSSPARARDRLMRRQGISAEEAPRRI
PDETAQRLNLPYLTVDSASTGQCFRLFVEQQAAPSIAAGSFNAYGLSAAAALPAW (SEQ ID NO:47)

RNA recognition sequences
GUUCACUGCCGGAUAGGCAGCUUAGAAA (SEQ ID NO:48)

FIG. 5W

>gi|188532992|ref|YP_001906789.1| hypothetical protein ETA_08450 [Erwinia tasmaniensis Eti/99]
MDRVQDIRVRVDAEMTAPVLIAQVFMRLHQVLMRAANGRIGISFPDVKLITLGDRIRLHGTILDDLSSLQQS
GWDKGLTDYIACSAIDPVPPGAAWRTVRRVQVKSSAERLRRSVNKGWLNEAFAAERINVLSEQRSDLPY
LQIKSGSNGHAWRLFIEHGPLVSVPVNGGFSSYGLSATATVPWF (SEQ ID NO:49)

RNA recognition sequences
GUUCACUGCCGCACAGGCAGCUUAGAAA (SEQ ID NO:19)
GUUCACUGCCGUACAGGCAGCUUAGAAG (SEQ ID NO:50)

FIG. 5X

>gi|160896663|ref|YP_001562245.1| CRISPR-associated Csy4 family protein [Delftia acidovorans SPH-1]
MAMTSHYIDTTILPDEFSHAHILGALVAKLHRAIVQLGSTDIGISFPGYSLRPRTLGTTILRLHGSEAAL
RGLMEQPMLQGMRDHVHCTPALVPEGAVPCIVQRRQEFKTSPDRLRRRMRRKGETAEQAAAAIPDSVER
TPDLPYVQLRSASTGQPFCLFVEQKAVQGTAGOEGFNTYGLSLGTAVPWF (SEQ ID NO:52)

RNA recognition sequence
GUUCGCUGCCGGGUAGGCAGCUCAGAAA

FIG. 5Y

>gi|146311064|ref|YP_001176138.1| CRISPR-associated Csy4 family protein [Enterobacter sp. 638]
MDHYLEIRVLSDPEFSEETLMAALFAKLHRALGARGQGDIGVSFPRYSIKPGDTLRLHGSAQSLDELEKM
AWRKGLSDYCLCKGVLPAPDVNAWRCVSRVQVKSSPQRLMRRSVKKGWLTEHEAQQRLLNLQEARTDLPW
LNLQSLSTGQSFRLFTRHGDIVDMPMCGEFSSYGLSATATIPWF (SEQ ID NO:53)

RNA recognition sequence
GUUCACUGCCGUACAGGCAGCUUAGAAA (SEQ ID NO:21)

FIG. 5Z

>gi|289209612|ref|YP_003461678.1| CRISPR-associated protein, Csy4 family [Thioalkalivibrio sp. K90mix]
MDHYLDLRVMPDPEFKETTLLGALVSKLHRRIVSMSADDIGISLPDHEQEPPLGRRLRVHGTQGRLNLLM
QDEWLGGMQSLVDATPVQPVPDQVTYRPVRRRQYKTNAERLRRRPMRRHGESYEEARQHIPDTVERRVNT
PFLSVQSASTGQRFSLFTEHGPPQQHASPGRFNTYGLSQDATVPWF (SEQ ID NO:54)

RNA recognition sequence
GUUAGCUGCCGCACAGGCAGCUCAGAAA (SEQ ID NO:55)

FIG. 5AA

>gi|128385631|ref|YP_162420.2| Csy4 family CRISPR-associated protein [Zymomonas mobilis subsp. mobilis ZM4]
MLANPVDSYQDIYILPMQEIAPHIIMEKLIFSLLHLEIVRLGSQHIGISFPEHDNNKPCLGSRLRLHGTGA
DLHELALSGMITRLDDYLYCEDIKSVPEIRQYCVVSRVQAKSSPARLRRAIRRHGFHDEEAKKVIPDTA
FERLELPFIMTGSCSTKQPRFPVFISHKIIQNFLMNGNFNSYGLSLGASVPWF (SEQ ID NO:56)

RNA recognition sequence
GUUCACUGCCGCACAGGCAGCUUAGAAA (SEQ ID NO:19)

FIG. 5AB

>gi|260752282|ref|YP_003225714.1| CRISPR-associated protein, Csy4 family [Zymomonas mobilis subsp. mobilis NCIMB 11163] MLANPVDSYQDIYILPNQEIAPHIMEKLFSLLHELEVRLGSQHIGISFPEHDNNKPCLGSRLRLHGAGA DLHELALSGNITRLDDYLYCEDIKSVPEIRQYCVVSRVQAKSSPARLRRAIRHNGFHDEEAKKVIPDTA FERRLELPFIMTGSCSTKQRPPVFISHKIIQDKIMNGNFNSYGLSLGASVPWF (SEQ ID NO:57)

RNA recognition sequence
GUUCACUGCCGCACAGGCAGCUUAGAAA (SEQ ID NO:19)

FIG. 5AC

>gi|121592915|ref|YP_984811.1| CRISPR-associated Csy4 family protein [Acidovorax sp. JS42] MTTHYINITILPDPEFSHAHTLGALVAKLHRALVQGHTTDIGVSYPQHVSQPLTKRTLGAVIRLHGTPEA LQRLMEEDWLKGMRDHTQVGELLPVPANAQHRTYRRKQFKTNADRLRRRMQRKGETAEQAAAAIPDTVE RRPDLPFVQLRSSTGQSFCLCVEHGPLPVAGAFNAYGHGHDATVPWF (SEQ ID NO:58)

RNA recognition sequences
GUUCACUGCCGUAUAGGCAGCUUCAGAAA (SEQ ID NO:59)

FIG. 5AD

>gi|317051103|ref|YP_004112219.1| Csy4 family CRISPR-associated protein [Desulfurispirillum indicum S5] MDSYIEIRILPDQEFEATTLMSYVFAKLHRALVESGRSDIGVSFPEAGKTPGALLRLHGSLAALESIMTL SWLTGLQDYTQTSGILQVPAQAAYVQVARVQSKMTASRIRRALKRGSLSEERALELLQSRDQLNQPFFRL LSASTAQKFPLFIEQRNAEKAGKQSVYSAYGLSVGGSTVPWF (SEQ ID NO:60)

RNA recognition sequence
GUUCACUGCCGUAUAGGCAGCUUCAGAAA (SEQ ID NO:59)

FIG. 5AE

>gi|54303643|ref|YP 133636.1| hypothetical protein PBPRB1991 [Photobacterium profundum SS9]
MMDSYVDIQLKPDAEMREAELSSKVFTKFHKALATLNTNKIGISFFQMNLKLGRLFRIHGNASLLKDLQG
IKWLGALAGYCQVGEITVVPDQVQYRVISVKRSNLSKAKLKRLIARGSIDKDGEKRYKVKMLSQGFDNPY
LDLFSSSTGQVYRKFFEFGDIQATSVSDEFDSYGLSNTATIPWF (SEQ ID NO:61)

RNA recognition sequence
GUUCACUGCCGCACAGGCAGCUUAGAAA (SEQ ID NO:19)

FIG. 5AF

>gi|54292953|ref|YP 122340.1| hypothetical protein plpl0047 [Legionella pneumophila str. Lens]
MDHYLDISILPDSEFTTPVLMNAIYTNLHKALHTLASTNIGVSFPKYSSTLGNLLRIHGKKEALQELQNL
NWIGGMIGYCEASLIKTVPADTKFRTVSRKQPTMSQSKLRRLIKRNSLTEDEIRQYKAKMFSKGLDNPYI
ELVSVSNGQRHRRYIEFGELFNEPIPGLFDQFGLSNSATVPWFD (SEQ ID NO:62)

RNA recognition sequences
GUUCACUGCCGUACAGGCAGCUUAGAAA (SEQ ID NO:21)
GUUCACUGCCGCACAGGCAGCUUAGAAA (SEQ ID NO:19)

FIG. 5AG

>gi|54295752|ref|YP 128167.1| hypothetical protein lpl2842 [Legionella pneumophila str. Lens]
MDHYLEISILPDSEFTTPVLMNAIYTNLHKALHTLASTSIGVSFPKYSSTLGNILRIHGKKEVLQDLQNL
NWIGGMIGYCEASLIKTVPADTKFRTVSRKQPTMSQSKLRRLIKRNTLTEDEIRQYKAKMFSKGLDNPYI
ELVSVSNGQRHRRYIEFGELFNEPSPGLFDQFGLSNSATVPWFD (SEQ ID NO:63)

RNA recognition sequences
GUUCACUGCCGUACAGGCAGCUUAGAAA (SEQ ID NO:21)
GUUCACUGCCGCACAGGCAGCUUAGAAA (SEQ ID NO:19)

FIG. 5AH

>gi|146292921|ref|YP_001183345.1| CRISPR-associated Csy4 family protein [Shewanella putrefaciens CN-32]
MRSYIDIRLKPDAEMREAELSSKVFTKFHKALVTLNSHKIGISFPQMKLSLGQLFRIHGDASLLHDLQGI
DWLGPLAGYCQVTAVSAVPDHVQYRIVSVKRSNLSKAKLKRLIARGSIDKDGEKRYKVKMLGQGFDNPYL
DLFSSSTGQVYRKFFEFSDIQAHPLDGEFDSYGLSKTATVPWF (SEQ ID NO:64)

RNA recognition sequence
GUUCACCGCCGCACAGGCGGCUUAGAAA (SEQ ID NO:65)

FIG. 5AI

>gi|296106567|ref|YP_003618267.1| hypothetical protein lpa_01476 [Legionella pneumophila 2300/99 Alcoy]
MDYYVDILIKPDSEKSLNFLLSTLYTKLHKVLADMASTNIGVSFPKYNITLGNILRIHSKKVVLDELLGM
NFLSGINNYYEVSPIKSVPADSKFRIISRKQTTMSQSKMRRLFKRGSMTVGDIRQYKAKMFAKSIDNPYL
ELVSGSNGYRYRYIEFGELLDQPVYGEFDRFGLSKTATVPWFD (SEQ ID NO:66)

RNA recognition sequence
GUUAACUGCCGCACACAGGCAGCUUAGAAG (SEQ ID NO:67)

FIG. 5AJ

>gi|260772736|ref|ZP_05881652.1| hypothetical protein VIB_001192 [Vibrio metschnikovii CIP 69.14]
MDSYIEIRLQPDAEMPEAELSSKVFTKFPHKALVTLHSNQIGISFPEVNVKLGRLFRIHGEASFLHDLQGL
NWLGPFLSGYCQVSEILAIPEQVQYRVISVKRSNLSQAKLRRLIARGSIDKEGEKRYKVKMLSQGFDNPYL
DLFSSSTKQVHRKFFEFGEIQPLPVSGKFDSYGLSHTTTVPWF (SEQ ID NO:68)

RNA recognition sequences
GUUCACUGCCGCACAGGCAGCUUAGAAA (SEQ ID NO:19)
GUUCACUGCCCAUAGGCAGCUUAGAAA (SEQ ID NO:69)

FIG. 5AK

>gi|157146437|ref|YP_001453756.1| hypothetical protein CKO_02197 [Citrobacter koseri ATCC BAA-895]
MAITPVPAVKGWRTVSRVQVKSSPQRLLRRSVRKGWLTEEQAQRLVESTEQHSDLPYLNVKSLSNQQF
RVFIRHSELRSEPVSGTFTSYGLSSTATIPWF (SEQ ID NO:70)

RNA recognition sequence
UGUUCACUGCCGUACAGGCAGCUUAGAAA (SEQ ID NO:21)

FIG. 5AL

>gi|262402803|ref|ZP_06079364.1| hypothetical protein VOA_000785 [Vibrio sp. RC586]
MDAYIDIRLMPDAEMREAELSSKVFIKFHKALVKLRSNKIGISFPEANIKLGRLFRLHGEMSALHDLQGL
NWLGPLAGYCKITTVTHVPDQVQYRIISVKRSNLSKAKLTRLIARGSIDKDGEKRYKVKMLSQGFDNPYL
DLSSSTGQVYRKFFEFSDIQADPVDGEFDSYGLSKTATVPWF (SEQ ID NO:19)

RNA recognition sequences
GUUCACUGCCGCACAGGCAGCUUAGAAA (SEQ ID NO:72)
AGUGUUCACUGCCGAAUAGCAGCUAAGAA (SEQ ID NO:72)

FIG. 5AM

>gi|229523353|ref|ZP_04412760.1| hypothetical protein VIF_000211 [Vibrio cholerae TM 11079-80]
MMDAYIDIRLMPDAEMREAELSSKVFIKFHKALVKLQSNKIGISFPEANIKLGRLFRLHGEVSALHDLQG
LNWLGPLAGYCKITTVTHVPDQVEYRIISVKRSNLSKAKLARLIARGSIDKDGEKRYKVKMLRQGFDNPY
LDLSSSSTGQVYRKFFEFSDIQAEPVDGEFDSYGLSKTATVPWF (SEQ ID NO:73)

RNA recognition sequence
GUUCACUGCCGCACAGGCAGCUUAGAAAU (SEQ ID NO:74)

FIG. 5AN

>gi|237748015|ref|ZP_04578495.1| crispr-associated protein [Oxalobacter formigenes OXCC13]
MKHYIEILTGSPDFPLYHLWSKLYTQLHLALVENRDASDQVNIGVSFPEYFNEEKGMGFLGTRLRLFA
EDETSLQKIDIQKWHVRLNDCIHITPVCRVPLNEITGYATFSRKHIKSNAERIARRQMKRHKDLSFHETV
QRYQKNLAKSPLFFIQLESLTNSHPFKLFIEKKPAINASLKVFTTYGLSAESTIPEF (SEQ ID NO:75)

RNA recognition sequence
GUUCACUGCGUAUAGGCAGCUUAGAAG (SEQ ID NO:76)

FIG. 5AO

>gi|119945137|ref|YP_942817.1| CRISPR-associated Csy4 family protein [Psychromonas ingrahamii 37]
MKYLIDITILPDIEIPLGFIWQKVFQQVHIALADNKVGENESDIALSLPNYGDKAFPIGNKLRLFSVSEQ
ALERLAITKWLKRFTDHTHITSVKAVPESANEYACFTRKQFNTNISKLARRRAKRHMETFEKALQYYDNF
AEEQTKLPFMNIKSLITNMAQERIFIERSITKIPKQGTFNCYGLSQAIATVPWF (SEQ ID NO:77)

RNA recognition sequence
GUGUUCCCGUGCCACGGGGAUGAACCG (SEQ ID NO:78)

FIG. 5AP

>gi|146328647|ref|YP_001209099.1| hypothetical protein DNO_0170 [Dichelobacter nodosus VCS1703A]
MNFYQEITILPDAEVSLYFIWSKVYGQLHIALADVRNRYGIDTIGVNFPHYVEEQNHKVVAARLGDQLR
IFALAENDLEKLQINQWLERLSDYVHIKRISKIEPNKVTGYVVKRYRYPSLDKVALRFAQFRKINFEEA
RKHCTKYKHQAKNYPFIMLKSQSNQEYYKLSIRQENAQESVSGRFNVYGIINSATGIVTVPNW (SEQ ID NO:79)

RNA recognition sequence
GUUCACCGCGCCACCAGGCGGCUUAGAAA (SEQ ID NO:65)

FIG. 5AQ

>gi|160876478|ref|YP_001555794.1| CRISPR-associated Csy4 family protein [Shewanella baltica OS195]
MNHYLDITLLPNEEVGHYFLWEKLYHQVHLALVEHKNRVGQFEIAAAFPQFNEMDNSLGSKLRLLATQPQ
HLEDLKVSNWLRHFTDYLHISSIRPVPEKIEVYVAYSRPAIRANKAREIARRMKRHNETLEQATAHFEGF
KPKKTKAPFVYMQSYTKDSRFPLFIQQTHSAVVKEGSVSFDSYGLSSRGYLPKF (SEQ ID NO:80)

RNA recognition sequence
GUUCACCGCCGCCACAGGCGGCUUAGAAA (SEQ ID NO:65)

FIG. 5AR

>gi|153001745|ref|YP_001367426.1| CRISPR-associated Csy4 family protein [Shewanella baltica OS185]
MNHYLDITLLPNEEVGHYFLWEKLYHQMHLALVEHKNRVGQFEIAAAFPQFNEMDNNLGSKLRLLATQPQ
HLEDLKVSNWLRHFTDYLHISSIRPVPDKIEVYVAYSRPAIRANKAREIARRMKRHNETLVQATAHFEGF
KPKKTKAPFVYMQSYTKDSRFPLFIQQTHSAVVKEGNVSFDSYGLSSRGYLPKF (SEQ ID NO:81)

RNA recognition sequence
GUUCACCGCCGCCACAGGCGGCUUAGAAA (SEQ ID NO:65)

FIG. 5AS

>gi|169795154|ref|YP_001712947.1| hypothetical protein ABAYE1000 [Acinetobacter baumannii AYE]
MMNWYQEITLIDQDEISLYFTWSKVYTQLHIAFAEHSNEQGRISFGYSFPQYRENEQKKIGFLGTKIRVF
ASSENDLQQINLGKWLERFIDYVHITQPREVPRAKITGYAHYRVNHRMSVEERIVHQAQRRNISLDQAR
QHFKQYVEQPVVEPYVSLKSLSAKREENVDRPYRLYIGKSIVDEARDGMFGTYGLSRMTTVPEF (SEQ ID NO:82)

RNA recognition sequence
GUUCAUGGGGGCAUACGCCAUUAGAAA (SEQ ID NO:83)

FIG. 5AT

>gi|213158184|ref|YP_002320235.1| crispr-associated protein, Csy4 family [Acinetobacter baumannii AB0057]
MNWYQEITLIDQDRISLYFIWSKVYTQLHIAFAEHSNEQGRISFQVSFPQYRINEQKIGFLGTKIRVFA
SSENDLQQLNLGKWLERFIDYVHITQPREVPRAKITGYAHYYRVPNHRMSVEERIVHQAQRRNISLDQARQ
HFKQYVEQPVVEPYVSLKSLSAKREENVDRPYRLYIGKSLVDEARDGMFGTYGLSRMFTVPEF (SEQ ID NO:84)

RNA recognition sequence
GUUCAUGGCGGCAUUAGAAA (SEQ ID NO:83)

FIG. 5AU

>gi|115602173|ref|NP_245245.1| hypothetical protein PM0308 [Pasteurella multocida subsp. multocida str. Pm70]
MTTHYIEIKAIPQMDMLQSEVIGHCMQILHQFLPHFEGRVGVAFPAYGLIGRTLGGIVRLEANQEDCNQLH
QQLLRSGLSDYALISEVSKTPLPTEHRSYSRVBRKGOSAIRRTEKRLKSQGRWDESIRADMQRQQNVAF
FPHCBLKSASTGQRFILAVKENRMPQSCVGVFNAYGLSNSATVPHF (SEQ ID NO:85)

RNA recognition sequences
GUUCACCAUCCUGUAGAUGCCUUAGAAA (SEQ ID NO:86)
GUUAACUGCCGUAAGAGGCAGCUUAGAAA (SEQ ID NO:87)

FIG. 5AV

>gi|293390434|ref|ZP_06634768.1| Csy4 family CRISPR-associated protein [Aggregatibacter actinomycetemcomitans D7S-1]
MTVQTHYIEIKAIPQVDMLQTEVIGFCLQKLHQILPHFEGRIGLAFPAYGNDKTLGGIIRLFGTENDCGF
IHFKLQSIRDYALISEVMPIPEKVRSYRIVQRHQPKGQSSIRRAEKRIHAQGKWNEEVLQNMLQKQATQR
IYPHAHLKSSTKQFILAIKSVHQTKAVEGVFSAYGLSQTTTVPHF (SEQ ID NO:88)

RNA recognition sequence
CUUCACUGCCGAAUAGGCAGCUUAGAAA (SEQ ID NO:89)

FIG. 5AW

>gi|152996699|ref|YP_001341534.1| CRISPR-associated Csy4 family protein [Marinomonas sp. MWYL1]
MKHYIDITLLPSDDIGVHFLWNSKLMMQVHLALVEIQNECKQVPVAVSFPKYQRENEKLGFVGNKLRLFA
NDKTDLERLNFGKWLHRLEDYVHIKSIADVPNDVISYESFNRRSKSGSPDKHIKRRMQRHNEFTWEQAAAF
FKGYSMEKADKDLPFIRMKSLHSDNEFCMSIIRKRAAPSNKHIMFNTYGLSAEGVLPKF (SEQ ID NO:90)

RNA recognition sequence
GUUCGCGCCGAGCACGCGGCUUAGAAA (SEQ ID NO:91)

FIG. 5AY

>gi|258645690|ref|ZP_05733159.1| CRISPR-associated protein, Csy4 family [Dialister invisus DSM 15470]
MEYQEFILLPCAEVSLAFLMTKVFTQLHIAFADEKNKSGHNLYAVSFPEVRETGLGEKIRVFAEAQELE
RLNLSKVLGRLLDYVHCTSIRKVFERKLRGYAVYSRYQPEGSIWKARRYAKRHPGVTIEEAARLLQGKR
KSVRLPYIQMKSLSRGGTFSLFIKKRVEKESALTECGTYGLSNNRFTVPEF (SEQ ID NO:92)

RNA recognition sequences
GUUAACUGCCGCAUAAGGUAGUUUAGAAA (SEQ ID NO:93)
GUUAUCUGCCGCGUAUAGGCAGCUUAGAAA (SEQ ID NO:94)

FIG. 5AZ

>gi|165975671|ref|YP_001651264.1| hypothetical protein APJL_0216 [Actinobacillus pleuropneumoniae serovar 3 str. JL03]
MSELTHYIELKAIPQVDILQTDVIAHGLQILHKFLPLYQGEHGLSFPAYGLGRTLGGHIRVFGNEQHCTQ
IKTQLIGEGLQDYVLITSVTPVPREIVEYHRYQRVHRKGQSAIRRFTEQFLVQQGKWTEEIRQEMLIBQQN
QKVFPYVKLKSGSTKQHFVLAIRQIRLAEPASGLFNAYGLSQAATVPHF (SEQ ID NO:95)

RNA recognition sequence
CUUCACUGCCGUAUAGGCAGCUUAGAAA (SEQ ID NO:96)

FIG. 5BA

>gi|190149486|ref|YP_001968011.1| hypothetical protein APP7_0217 [Actinobacillus pleuropneumoniae serovar 7 str. AP76]
MSELTHYIELKAIPQVDILQTDVIAHGLQILHKFLPLYQGEIGLSFPAYGLGRTLGGIIRVFGNEQHCTQ
IKTQLIGEGLQDYVLITSVTPVPEEIVEYHRYQRVHRKGQSAIRRTEQFLVQQGKWTEEIRQEMLHQQN
QKVFPYVKLRSGSTKQHFVLAIRQLRLAEPVSGLFNAYGLSKIATVPHF (SEQ ID NO:96)

RNA recognition sequence
CUUCACUGCCGUAUAGGCAGCUUAGAAA (SEQ ID NO:97)

FIG. 5BB

>gi|303253029|ref|ZP_07339182.1| hypothetical protein APP2_1978 [Actinobacillus pleuropneumoniae serovar 2 str. 4226]
MSELTHYIELKAIPQVDILQTDVIAHGLQILHKFLPLYQGEIGLSFPAYGLGRTLGGIIRVFGNEQHCTQ
IKTQLIGEGLQDYVLITSVTPVPEEIVEYHRYQRVHRKGQSAIRRTEQFLVQQGKWTEEIRQEMLHQQN
QKVFPHVKLRSGSTKQHFVLAIRQLRLAEPSFGLFNTYGLSKIATVPHF (SEQ ID NO:98)

FIG. 5BC

>gi|303251662|ref|ZP_07337835.1| hypothetical protein APP6_0866 [Actinobacillus pleuropneumoniae serovar 6 str. Femo]
MSELTHYIELKAIPQVDILQTDVIAHGLQILHKFLPLYQGEIGLSFPAYGLGRTLGGIIRVFGNEQHCTQ
IKTQLIGEGLQDYVLITSVTPVPEEIVEYHRYQRVHRKGQSAIRRTEQFLVQQGKWTEEIRQEMLHQQN
QKVFPHVKLRSGSTKQHFVLAIRQLRLAEPSFGLFNTYGLSKIATVPHF (SEQ ID NO:99)

FIG. 5BD

>gi|116627507|ref|YP_820126.1| dephospho-CoA kinase [Streptococcus thermophilus LMD-9]
MSKTMIGLFSGGIASGKSTVVEIIKDAGYKVIDADQLVHDMQVKGGRLYQALLDMLGDGILLFNGELNRP
KLGQLIFSSEEMRYQSAEIQGKIIREELAAKPDCLAKEEDVFFMDIPLLFENDYQDWFDQIWLVAVSPQV
QGQRLMKRNHLSAEEAGMRIASQMPLAEKLPYASIVIDNNGNIDDLKKKVKGAIRDLANLV (SEQ ID NO:100)

FIG. 6

His29Ala 1 mdhyldirir pdpefppaqi msvlfgklaq alvaqggdri gvsfpdldes rsrlgerlri
 61 hasaddlral larpwiegir dhiqfgepav vphptpyrqv srvqvksnpe rlrrrlmrrh
121 diseeearkr ipdtvaraid lpfvtirsqs tgqhrifir hgplqataee ggftcygisk
181 ggfvpwf (SEQ ID NO:101)

His29Ala/Ser50Cys 1 mdhyldirir pdpefppaqi msvlfgklaq alvaqggdri gvsfpdldec rsrlgerlri
 61 hasaddlral larpwiegir dhiqfgepav vphptpyrqv srvqvksnpe rlrrrlmrrh
121 diseeearkr ipdtvaraid lpfvtirsqs tgqhrifir hgplqataee ggftcygisk
181 ggfvpwf (SEQ ID NO:102)

Figure 11A

Csy4 sequence
>*Pseudomonas aeruginosa* (Pa14)
MDHYLDIRLRPDPEFPPAQLMSVLFGKLHQALVAQGGDRIGVSFPDLDESRSRLGERLRIHASA
DDLRALLARPWLEGLRDHLQFGEPAVVPHPTPYRQVSRVQAKSNPERLRRRLMRRHDLSEEEAR
KRIPDTVARALDLPFVTLRSQSTGQHFRLFIRHGPLQVTAEEGGFTCYGLSKGGFVPWF (SEQ
ID NO:104)

Pa14 H29A
MDHYLDIRLRPDPEFPPAQLMSVLFGKLAQALVAQGGDRIGVSFPDLDESRSRLGERLRIHASA
DDLRALLARPWLEGLRDHLQFGEPAVVPHPTPYRQVSRVQAKSNPERLRRRLMRRHDLSEEEAR
KRIPDTVARALDLPFVTLRSQSTGQHFRLFIRHGPLQVTAEEGGFTCYGLSKGGFVPWF (SEQ
ID NO:105)

RNA recognition sequence (short and long forms)

GUUCACUGCCGUGUAGGCAGCUAAGAAA (SEQ ID NO:7)
GUUCACUGCCGUAUAGGCAGCUAAGAAA (SEQ ID NO:1)

Figure 11B

>*Escherichia coli* UTI89 (Ec89)
MDHYLEIRVLPDPEFSSEMLMAALFAKLHRVLGARGQGDIGVSFPDVNVMPGARLRLHGSAQALQALEAS
TWRKGLTDYCQCSPVTPVPEIKGWRVVSRVQVKSNPQRLLRRSVKKGWLTEEQAIERLATQAEQRTDLPF
LNMKSLSSQQLFKLFIRHGDLLKEPVKGEFSSYGLSATATIPWF (SEQ ID NO:39)

Ec89 H29A
MDHYLEIRVLPDPEFSSEMLMAALFAKLARVLGARGQGDIGVSFPDVNVMPGARLRLHGSAQALQALEAS
TWRKGLTDYCQCSPVTPVPEIKGWRVVSRVQVKSNPQRLLRRSVKKGWLTEEQAIERLATQAEQRTDLPF
LNMKSLSSQQLFKLFIRHGDLLKEPVKGEFSSYGLSATATIPWF (SEQ ID NO:106)

RNA recognition sequence (short and long forms)

GUUCACUGCCGUACAGGCAGC (SEQ ID NO:113)
GUUCACUGCCGUACAGGCAGCUUAGAAA (SEQ ID NO:21)

Figure 11C

>*Dichelobacter nodosus* VCS1703A (Dn)
MNFYQEITLLPDAEVSLYFLWSKVYGQLHIALADVRNRYGIDTIGVNFPHYVYEEQNHKVVAARLGDQLR
IFALAENDLEKLQINQWLERLSDYVHIKRISKIEPNKVTGYVVVKRYRYPSLDKVALRFAQFRKINFEEA
RKHCTKYKHQAKNYPFIMLKSQSNQEYYKLSIRQENAQESVSGRFNVYGINSATGIVTVPNW  (SEQ ID
NO:79)

Dn H29A
MNFYQEITLLPDAEVSLYFLWSKVYGQLAIALADVRNRYGIDTIGVNFPHYVYEEQNHKVVAARLGDQLR
IFALAENDLEKLQINQWLERLSDYVHIKRISKIEPNKVTGYVVVKRYRYPSLDKVALRFAQFRKINFEEA
RKHCTKYKHQAKNYPFIMLKSQSNQEYYKLSIRQENAQESVSGRFNVYGINSATGIVTVPNW(SEQ ID
NO:107)

RNA recognition sequence (short and long forms)

GUUCACUGCCGUACAGGCAGC           (SEQ ID NO:114)
GUUCACCGCCGCACAGGCGGCUUAGAAA    (SEQ ID NO:65)

Figure 11D

>*Acinetobacter sp.* ADP1 Csy4 – ACIAD2483 – (AA)
MDANYYLDIRVLESSDDTDLKLGHIRNQIYTVIHGAFRKLPAHYALALEMSDKLKAKQEQFEKKHGRSAK
PNFDILRIFAEKQDELDELVEAIKGHWKIRDYTVLGVAIAVPTAKISGWKSYRKFRIPTQKAERTKLSHQ
NEPLRDRRLKTAKGMPFFQVISQSTGQGFTVIIDVQESENAGYGLPDSYGLARKESPFALPVF(SEQ ID
NO:108)

AA H34A
MDANYYLDIRVLESSDDTDLKLGHIRNQIYTVIAGAFRKLPAHYALALEMSDKLKAKQEQFEKKHGRSAK
PNFDILRIFAEKQDELDELVEAIKGHWKIRDYTVLGVAIAVPTAKISGWKSYRKFRIPTQKAERTKLSHQ
NEPLRDRRLKTAKGMPFFQVISQSTGQGFTVIIDVQESENAGYGLPDSYGLARKESPFALPVF(SEQ ID
NO:109)

RNA recognition sequence (short and long forms)

RNA1    CUUAACUGCCGCACAGGCAGC           (SEQ ID NO:115)
RNA1    CUUAACUGCCGCACAGGCAGCUUAGAAA    (SEQ ID NO:116)

RNA2    CUUCACUACCGCACAGGUAGC           (SEQ ID NO:117)
RNA2    CUUCACUACCGCACAGGUAGCUUAGAAA    (SEQ ID NO:118)

Figure 11E

>*Shewanella sp.* W3-18-1 Csy4 - YP_963568 - (SspW3)
MKYYLDITLLPDAEANLGFLWHKVYQQIHLMLVEHKVSVENSAIGLSFPKYDAKSFSDNTKFPLGDKLRL
FAGTEQQLADLKVAQWLARLADYVHIKAIKAVPDNVSEYAYFKRRHFKSPDKLRRNIDARAIVIAQKNGF
AINEVKTRLLASIDNLDTKSKLPFINLRSLSTEKDVSPADRRKFLLFIECEKVTKPSQNNGLFNCYGLSR
RAQTEQAAVPWFEG(SEQ ID NO:110)

SspW3 H29A
MKYYLDITLLPDAEANLGFLWHKVYQQIALMLVEHKVSVENSAIGLSFPKYDAKSFSDNTKFPLGDKLRL
FAGTEQQLADLKVAQWLARLADYVHIKAIKAVPDNVSEYAYFKRRHFKSPDKLRRNIDARAIVIAQKNGF
AINEVKTRLLASIDNLDTKSKLPFINLRSLSTEKDVSPADRRKFLLFIECEKVTKPSQNNGLFNCYGLSR
RAQTEQAAVPWFEG(SEQ ID NO:111)

RNA recognition sequence (short and long forms)

| | | |
|---|---|---|
| RNA1 | GUUCACCGCCACACAGGCGGC | (SEQ ID NO:119) |
| RNA1 | GUUCACCGCCACACAGGCGGCUUAGAAA | (SEQ ID NO:120) |
| RNA2 | GUUCACUGCCGCACAGGCAGC | (SEQ ID NO:121) |
| RNA2 | GUUCACUGCCGCACAGGCAGCUUAGAAA | (SEQ ID NO:122) |

Figure 11F

>*Acinetobacter baumannii* AB0057 (Ab)
MNWYQEITLIDQDEISLYFIWSKVYTQLHIAFAEHSNEQGRISFGVSFPQYRINEQKKIGFLGTKIRVFA
SSENDLQQLNLGKWLERFIDYVHITQPREVPRAKITGYAHYYRVNHRMSVEERIVHQAQRRNISLDQARQ
HFKQYVEQPVVEPYVSLKSLSAKREENVDRPYRLYIGKSLVDEARDGMFGTYGLSRMTTVPEF (SEQ ID NO:84)

Ab H29A
MNWYQEITLIDQDEISLYFIWSKVYTQLAIAFAEHSNEQGRISFGVSFPQYRINEQKKIGFLGTKIRVFA
SSENDLQQLNLGKWLERFIDYVHITQPREVPRAKITGYAHYYRVNHRMSVEERIVHQAQRRNISLDQARQ
HFKQYVEQPVVEPYVSLKSLSAKREENVDRPYRLYIGKSLVDEARDGMFGTYGLSRMTTVPEF (SEQ ID NO:112)

RNA recognition sequence (short and long forms)

| | |
|---|---|
| GUUCAUGGCGGCAUACGCCAUU | (SEQ ID NO:123) |
| GUUCAUGGCGGCAUACGCCAUUUAGAAA | (SEQ ID NO:83) |

Figure 11G

>*Marinomonas sp. MWYL1* (MM)
MKHYIDITLLPSDDIGVHFLWSKLMMQVHLALVEIQNEQKQVPVAVSFPKYQPRENEKLGFVGNKLRLFA
NDKTDLERLNFGKWLHRLEDYVHIKSIADVPNDVISYESFNRRSKSGSPDKHIKRRMQRHNETWEQAAAF
FKGYSMEKADKDLPFIRMKSLHSDNEFCMSIIRKEAAPSNKHIMFNTYGLSAEGVLPKF  (SEQ ID
NO:90)

RNA recognition sequence (long form)

GUUCGCCGCCGAGCACGCGGCUUAGAAA (SEQ ID NO:91)

| | PA14 RNA | Ec89 RNA | Dn RNA | AA RNA1 | AA RNA2 | Ab RNA | MM RNA | SspW3 RNA1 | SspW3 RNA2 |
|---|---|---|---|---|---|---|---|---|---|
| Pa14 Csy4 | 3.7 | 4.2 | 1.29 | 5.6 | 2.3 | 0.00070 | 0.0023 | 0.01260 | 3.7 |
| Ec89 Csy4 | 2.02 | 3.8 | 0.56 | 4.79 | 4.23 | 0 | 0.0024 | 0 | 5.3 |
| Dn Csy4 | 0.435 | 2.74 | 2.1 | 10.9 | 7.10 | 0.0058 | 0.0307 | 2.40 | 3.76 |
| AA Csy4 | 19 | 16 | 5.4 | 17 | 16 | 0.054 | 0.096 | 5.7 | 18 |
| Ab Csy4 | 0.024 | 1.89 | 0.78 | 1.6 | 0.77 | 4.5 | 0.026 | 1.05 | 1.52 |
| MM Csy4 | 0.46 | 16 | 2.6 | 15.3 | 9.2 | 0.0132 | 6.6 | 0.20 | 15.3 |

FIG. 13A

| | PA14 RNA | Ec89 RNA | Dn RNA | AA RNA1 | AA RNA2 | Ab RNA | MM RNA | SspW3 RNA1 | SspW3 RNA2 |
|---|---|---|---|---|---|---|---|---|---|
| Pa14 Csy4 | 66.1% | 75.0% | 23.0% | 100.0% | 41.1% | 0.0% | 0.0% | 0.2% | 66.1% |
| Ec89 Csy4 | 38.1% | 71.7% | 10.6% | 90.4% | 79.8% | 0.0% | 0.0% | 0.0% | 100.0% |
| Dn Csy4 | 4.0% | 25.1% | 19.3% | 100.0% | 65.1% | 0.1% | 0.3% | 22.0% | 34.5% |
| AA Csy4 | 100.0% | 84.2% | 28.4% | 89.5% | 84.2% | 0.3% | 0.5% | 30.0% | 94.7% |
| Ab Csy4 | 0.5% | 42.0% | 17.3% | 35.6% | 17.1% | 100.0% | 0.6% | 23.3% | 33.8% |
| MM Csy4 | 2.9% | 100.0% | 16.3% | 95.6% | 57.5% | 0.1% | 41.3% | 1.3% | 95.6% |

FIG. 13B

SEQUENCE LISTING

<160> NUMBER OF SEQ ID NOS: 123

<210> SEQ ID NO 1
<211> LENGTH: 28
<212> TYPE: RNA
<213> ORGANISM: Artificial Sequence
<220> FEATURE:
<223> OTHER INFORMATION: Synthetic sequence

<400> SEQUENCE: 1
guucacugcc guauaggcag cuaagaaa                                          28

<210> SEQ ID NO 2
<211> LENGTH: 204
<212> TYPE: PRT
<213> ORGANISM: Moritella sp. PE36

<400> SEQUENCE: 2

Met Leu Asn Arg Phe Tyr Phe Tyr Ile Lys Phe Ile Pro Gln His Thr
1               5                   10                  15

Asp Asn Ala Phe Leu Ile Gly Arg Cys Ile Lys Val Ser His Ala Phe
            20                  25                  30

```
Phe Ala Lys His Ser Ile Thr Gly Val Gly Val Ser Phe Pro Cys Trp
        35                  40                  45

Ser Glu Gln Asp Ile Gly Asn Ala Leu Ala Phe Val Ser Thr Asp Met
 50                  55                  60

Glu Ala Leu Glu Gln Leu Lys Ala Gln Pro Leu Phe Ser Val Met Ala
 65                  70                  75                  80

Asp Glu Leu Ile Phe Glu Ile Ser Asp Val Leu Ser Ile Pro Asp Lys
                 85                  90                  95

Leu Glu Glu Glu Arg Phe Thr Leu Asn Tyr Ala Ile Arg Lys Ser Phe
                100                 105                 110

Ala Gly Asp Lys Lys Arg Arg Leu Lys Arg Ala Lys Lys Arg Ala Glu
                115                 120                 125

Ala Arg Gly Glu Thr Tyr Lys Pro Val Leu His Ile Asn Thr Glu Lys
            130                 135                 140

Arg Val Phe Asn His Tyr His Thr Ile Pro Met Asn Ser Lys Glu Lys
145                 150                 155                 160

Pro Asp Gly Phe Thr Leu His Val Gln Lys Asn Pro Cys Val Glu Gln
                165                 170                 175

Tyr Ala Ala Asp Phe Leu Asp Tyr Gly Phe Ala Thr Asn Glu Gln His
                180                 185                 190

Arg Gly Thr Val Pro Lys Leu Ser Ser Leu Met Lys
            195                 200

<210> SEQ ID NO 3
<211> LENGTH: 192
<212> TYPE: PRT
<213> ORGANISM: Moritella sp. PE36

<400> SEQUENCE: 3

Met Asp Val Phe Leu Leu Ser Gly Arg Cys Ala Lys Ala Leu His Asn
 1               5                  10                  15

Phe Glu Phe Lys Lys Arg Lys His Asn Ile Gly Ile Ala Leu Pro Cys
                 20                  25                  30

Trp Ser Glu Asn Ser Val Gly Asp Met Ile Ala Phe Val Ser Glu Asp
             35                  40                  45

Lys Asn Gln Leu Leu Lys Phe His Gln Asp Ser Tyr Phe Gln Met Met
 50                  55                  60

Ala Ser Asp Glu Ile Phe Ile Ile Ser Asp Ile Thr Ala Val Asn Ser
 65                  70                  75                  80

Glu Leu Pro Glu Val Gln Phe Cys Arg Asn Asn Thr Ile Ser Lys Met
                 85                  90                  95

Phe Ile Lys Asp Thr Gln Lys Arg Leu Arg Arg Thr Gln Lys Arg Ala
                100                 105                 110

Glu Ala Arg Gly Asp Ala Phe Lys Pro Ala Leu His Glu Asn Ser Lys
            115                 120                 125

Lys Arg Val Phe Glu Asn Phe His Ser Leu Pro Ile Asp Ser Tyr Gly
130                 135                 140

Thr Glu Glu Asp Phe Met Leu His Ile Gln Lys His Asn Asp Val Ala
145                 150                 155                 160

Leu Ser Asp Cys Tyr Thr Ser Tyr Gly Phe Ala Thr Asn Asn Asp Asn
                165                 170                 175

Arg Gly Thr Val Pro Asp Met Ser Ile Leu Phe Asn Gln Met Thr Lys
            180                 185                 190
```

-continued

```
<210> SEQ ID NO 4
<211> LENGTH: 224
<212> TYPE: PRT
<213> ORGANISM: Shewanella sp. W3-18-1

<400> SEQUENCE: 4
```

Met Lys Tyr Tyr Leu Asp Ile Thr Leu Leu Pro Asp Ala Glu Ala Asn
1               5                   10                  15

Leu Gly Phe Leu Trp His Lys Val Tyr Gln Gln Ile His Leu Met Leu
            20                  25                  30

Val Glu His Lys Val Ser Val Glu Asn Ser Ala Ile Gly Leu Ser Phe
        35                  40                  45

Pro Lys Tyr Asp Ala Lys Ser Phe Ser Asp Asn Thr Lys Phe Pro Leu
    50                  55                  60

Gly Asp Lys Leu Arg Leu Phe Ala Gly Thr Glu Gln Gln Leu Ala Asp
65                  70                  75                  80

Leu Lys Val Ala Gln Trp Leu Ala Arg Leu Ala Asp Tyr Val His Ile
                85                  90                  95

Lys Ala Ile Lys Ala Val Pro Asp Asn Val Ser Glu Tyr Ala Tyr Phe
            100                 105                 110

Lys Arg Arg His Phe Lys Ser Pro Asp Lys Leu Arg Arg Asn Ile Asp
        115                 120                 125

Ala Arg Ala Ile Val Ile Ala Gln Lys Asn Gly Phe Ala Ile Asn Glu
    130                 135                 140

Val Lys Thr Arg Leu Leu Ala Ser Ile Asp Asn Leu Asp Thr Lys Ser
145                 150                 155                 160

Lys Leu Pro Phe Ile Asn Leu Arg Ser Leu Ser Thr Glu Lys Asp Val
                165                 170                 175

Ser Pro Ala Asp Arg Arg Lys Phe Leu Leu Phe Ile Glu Cys Glu Lys
            180                 185                 190

Val Thr Lys Pro Ser Gln Asn Asn Gly Leu Phe Asn Cys Tyr Gly Leu
        195                 200                 205

Ser Arg Arg Ala Gln Thr Glu Gln Ala Ala Val Pro Trp Phe Glu Gly
    210                 215                 220

```
<210> SEQ ID NO 5
<211> LENGTH: 167
<212> TYPE: PRT
<213> ORGANISM: Pseudomonas aeruginosa

<400> SEQUENCE: 5
```

Met Ser Val Leu Phe Gly Lys Leu His Gln Ala Leu Val Ala Gln Gly
1               5                   10                  15

Gly Asp Arg Ile Gly Val Ser Phe Pro Asp Leu Asp Glu Ser Arg Ser
            20                  25                  30

Arg Leu Gly Glu Arg Leu Arg Ile His Ala Ser Ala Asp Asp Leu Arg
        35                  40                  45

Ala Leu Leu Ala Arg Pro Trp Leu Glu Gly Leu Arg Asp His Leu Gln
    50                  55                  60

Phe Gly Glu Pro Ala Val Val Pro His Pro Thr Pro Tyr Arg Gln Val
65                  70                  75                  80

Ser Arg Val Gln Ala Lys Ser Asn Pro Glu Arg Leu Arg Arg Arg Leu
                85                  90                  95

Met Arg Arg His Asp Leu Ser Glu Glu Glu Ala Arg Lys Arg Ile Pro
            100                 105                 110

Asp Thr Val Ala Arg Ala Leu Asp Leu Pro Phe Val Thr Leu Arg Ser

```
            115                 120                 125
Gln Ser Thr Gly Gln His Phe Arg Leu Phe Ile Arg His Gly Pro Leu
        130                 135                 140
Gln Val Thr Ala Glu Glu Gly Gly Phe Thr Cys Tyr Gly Leu Ser Lys
145                 150                 155                 160
Gly Gly Phe Val Pro Trp Phe
                165
```

<210> SEQ ID NO 6
<211> LENGTH: 187
<212> TYPE: PRT
<213> ORGANISM: Pseudomonas aeruginosa

<400> SEQUENCE: 6

```
Met Asp His Tyr Leu Asp Ile Arg Leu Arg Pro Asp Pro Glu Phe Pro
1               5                   10                  15
Pro Ala Gln Leu Met Ser Val Leu Phe Gly Lys Leu His Gln Ala Leu
            20                  25                  30
Val Ala Gln Gly Gly Asp Arg Ile Gly Val Ser Phe Pro Asp Leu Asp
        35                  40                  45
Glu Ser Arg Ser Arg Leu Gly Glu Arg Leu Arg Ile His Ala Ser Ala
    50                  55                  60
Asp Asp Leu Arg Ala Leu Leu Ala Arg Pro Trp Leu Glu Gly Leu Arg
65                  70                  75                  80
Asp His Leu Gln Phe Gly Glu Pro Ala Val Val Pro His Pro Thr Pro
                85                  90                  95
Tyr Arg Gln Val Ser Arg Val Gln Val Lys Ser Asn Pro Glu Arg Leu
            100                 105                 110
Arg Arg Arg Leu Met Arg His Asp Leu Ser Glu Glu Glu Ala Arg
        115                 120                 125
Lys Arg Ile Pro Asp Thr Val Ala Arg Ala Leu Asp Leu Pro Phe Val
    130                 135                 140
Thr Leu Arg Ser Gln Ser Thr Gly Gln His Phe Arg Leu Phe Ile Arg
145                 150                 155                 160
His Gly Pro Leu Gln Val Thr Ala Glu Glu Gly Gly Phe Thr Cys Tyr
                165                 170                 175
Gly Leu Ser Lys Gly Gly Phe Val Pro Trp Phe
            180                 185
```

<210> SEQ ID NO 7
<211> LENGTH: 28
<212> TYPE: RNA
<213> ORGANISM: Artificial Sequence
<220> FEATURE:
<223> OTHER INFORMATION: Synthetic oligonucleotide

<400> SEQUENCE: 7
guucacugcc guguaggcag cuaagaaa                                     28

<210> SEQ ID NO 8
<211> LENGTH: 187
<212> TYPE: PRT
<213> ORGANISM: Pseudomonas aeruginosa

<400> SEQUENCE: 8

```
Met Asp His Tyr Leu Asp Ile Arg Leu Arg Pro Asp Pro Glu Phe Pro
1               5                   10                  15
Pro Ala Gln Leu Met Ser Val Leu Phe Gly Lys Leu His Gln Ala Leu
```

```
            20                  25                  30
Val Ala Gln Gly Gly Asp Arg Ile Gly Val Ser Phe Pro Asp Leu Asp
        35                  40                  45
Glu Ser Arg Ser Arg Leu Gly Glu Arg Leu Arg Ile His Ala Ser Ala
    50                  55                  60
Asp Asp Leu Arg Ala Leu Leu Ala Arg Pro Trp Leu Glu Gly Leu Arg
65                  70                  75                  80
Asp His Leu Gln Phe Gly Glu Pro Ala Val Val Pro His Pro Thr Pro
                85                  90                  95
Tyr Arg Gln Val Ser Arg Val Gln Ala Lys Ser Asn Pro Glu Arg Leu
            100                 105                 110
Arg Arg Arg Leu Met Arg Arg His Asp Leu Ser Glu Glu Glu Ala Arg
        115                 120                 125
Lys Arg Ile Pro Asp Thr Val Ala Arg Thr Leu Asp Leu Pro Phe Val
    130                 135                 140
Thr Leu Arg Ser Gln Ser Thr Gly Gln His Phe Arg Leu Phe Ile Arg
145                 150                 155                 160
His Gly Pro Leu Gln Ala Thr Ala Glu Glu Gly Gly Phe Thr Cys Tyr
                165                 170                 175
Gly Leu Ser Lys Gly Gly Phe Val Pro Trp Phe
            180                 185

<210> SEQ ID NO 9
<211> LENGTH: 187
<212> TYPE: PRT
<213> ORGANISM: Pseudomonas aeruginosa

<400> SEQUENCE: 9

Met Asp His Tyr Leu Asp Ile Arg Leu Arg Pro Asp Pro Glu Phe Pro
1               5                   10                  15
Pro Ala Gln Leu Met Ser Val Leu Phe Gly Lys Leu His Gln Ala Leu
            20                  25                  30
Val Ala Gln Gly Gly Asp Arg Ile Gly Val Ser Phe Pro Asp Leu Asp
        35                  40                  45
Glu Ser Arg Ser Arg Leu Gly Glu Arg Leu Arg Ile His Ala Ser Ala
    50                  55                  60
Asp Asp Leu His Ala Leu Leu Ala Arg Pro Trp Leu Glu Gly Leu Arg
65                  70                  75                  80
Asp His Leu Gln Phe Gly Glu Ala Ala Val Val Pro His Pro Thr Pro
                85                  90                  95
Tyr Arg Gln Val Ser Arg Val Gln Ala Lys Ser Asn Pro Glu Arg Leu
            100                 105                 110
Arg Arg Arg Leu Met Arg Arg His Asp Leu Ser Glu Glu Glu Ala Arg
        115                 120                 125
Lys Arg Ile Pro Asp Thr Val Ala Arg Thr Leu Asp Leu Pro Phe Val
    130                 135                 140
Thr Leu Arg Ser Gln Ser Thr Gly Gln His Phe Arg Leu Phe Ile Arg
145                 150                 155                 160
His Gly Pro Leu Gln Ala Thr Ala Glu Glu Gly Gly Phe Thr Cys Tyr
                165                 170                 175
Gly Leu Ser Lys Gly Gly Phe Val Pro Trp Phe
            180                 185

<210> SEQ ID NO 10
<211> LENGTH: 184
```

```
<212> TYPE: PRT
<213> ORGANISM: Dickeya dadantii

<400> SEQUENCE: 10

Met Asp His Tyr Ile Glu Ile Arg Val Leu Pro Asp Leu Glu Phe Ser
1               5                   10                  15

Ala Val Gln Leu Leu Ser Ala Leu Phe Ala Lys Leu His Arg Ala Leu
            20                  25                  30

Gly Gln Arg Ala Thr Gly Ala Ile Gly Val Ser Phe Pro Asp Val Asp
        35                  40                  45

Lys Thr Leu Gly Glu Arg Leu Arg Leu His Gly Ser Val Gln Glu Leu
    50                  55                  60

Ala Ala Leu Glu Gln Thr Gly Trp Leu Lys Gly Leu Arg Asp Tyr Thr
65                  70                  75                  80

Ala Ile Thr Glu Pro Leu Pro Val Pro Ala Gly Ala Lys His Arg Thr
                85                  90                  95

Val Arg Arg Val Gln Val Lys Ser Ser Ala Glu Arg Leu Arg Arg Arg
            100                 105                 110

Ala Val Ser Lys Gly Arg Met Thr Glu Asp Glu Ala Ala Thr Arg Ile
        115                 120                 125

Pro Tyr Ala Val Glu Lys Arg Ser Ser Leu Pro Tyr Leu Pro Leu Arg
    130                 135                 140

Ser Leu Ser Ser Gly Gln Thr Phe Leu Leu Phe Val Glu His Gly Pro
145                 150                 155                 160

Leu Gln Asp Lys Pro Val Ala Gly Ala Phe Ser Ser Tyr Gly Leu Ser
                165                 170                 175

Ala Thr Thr Thr Ile Pro Trp Phe
            180

<210> SEQ ID NO 11
<211> LENGTH: 28
<212> TYPE: RNA
<213> ORGANISM: Artificial Sequence
<220> FEATURE:
<223> OTHER INFORMATION: Synthetic oligonucleotide

<400> SEQUENCE: 11
guucacugcc gcguaggcag cuuagaaa                                              28

<210> SEQ ID NO 12
<211> LENGTH: 28
<212> TYPE: RNA
<213> ORGANISM: Artificial Sequence
<220> FEATURE:
<223> OTHER INFORMATION: Synthetic oligonucleotide

<400> SEQUENCE: 12
guucacugcc gaguaggcag cuuagaaa                                              28

<210> SEQ ID NO 13
<211> LENGTH: 184
<212> TYPE: PRT
<213> ORGANISM: Pectobacterium wasabiae

<400> SEQUENCE: 13

Met Asp His Tyr Ile Asp Ile Arg Val Gln Pro Asp Pro Glu Phe Thr
1               5                   10                  15

Ala Pro Gln Leu Leu Asn Ala Leu Phe Ala Lys Leu His Arg Ala Leu
            20                  25                  30
```

```
Gly Gln Leu Ala Asp Gly Lys Ile Gly Ile Ser Phe Pro Glu Val Gly
             35                  40                  45

Lys Thr Leu Gly Glu Cys Leu Arg Leu His Gly Thr Ala Asp Ala Leu
 50                  55                  60

Ser Thr Leu Glu Lys Thr Ser Trp Leu Lys Gly Leu Arg Asp Tyr Thr
 65                  70                  75                  80

Gln Val Ser Glu Cys Lys Ala Val Pro Asn Asn Val Lys Phe Arg Thr
                 85                  90                  95

Val Arg Arg Val Gln Leu Lys Thr Ser Ala Glu Arg Leu Arg Arg Arg
            100                 105                 110

Ser Val Asn Lys Gly Trp Leu Thr Glu Ala Glu Ala Ala Arg Ile
            115                 120                 125

Pro Asp Ala Val Glu Lys Arg Ser Thr Leu Pro Phe Val Gln Ile Lys
130                 135                 140

Ser Leu Ser Asn Gly Gln Met Phe Phe Val Phe Val Glu His Gly Pro
145                 150                 155                 160

Leu Gln Asn Ala Pro Ala Thr Gly Arg Phe Ser Ser Tyr Gly Leu Ser
                165                 170                 175

Ala Glu Ala Thr Val Pro Trp Phe
            180

<210> SEQ ID NO 14
<211> LENGTH: 28
<212> TYPE: RNA
<213> ORGANISM: Artificial Sequence
<220> FEATURE:
<223> OTHER INFORMATION: Synthetic oligonucleotide

<400> SEQUENCE: 14
guucacugcc guauaggcag cuuagaaa                                           28

<210> SEQ ID NO 15
<211> LENGTH: 184
<212> TYPE: PRT
<213> ORGANISM: Photorhabdus asymbiotica

<400> SEQUENCE: 15

Met Asp Tyr Tyr Phe Glu Ile Leu Val Leu Pro Asp Pro Glu Phe Ser
 1               5                  10                  15

Lys Gln Ser Leu Met Glu Ala Leu Phe Ala Lys Leu His Arg Ala Leu
             20                  25                  30

Gly Gln Val Gly Asn Gly Arg Ile Gly Val Ser Phe Pro Cys Ala Arg
             35                  40                  45

Lys Thr Leu Gly Asp Lys Leu Arg Ile His Gly Ala Ser Glu Ala Leu
 50                  55                  60

Asn Asp Leu Gln Ala Leu Pro Trp Leu Lys Gly Leu Arg Asp Tyr Thr
 65                  70                  75                  80

Glu Ile Met Asp Ile Gln Pro Val Pro Gln Asp Thr Gln Tyr Arg Arg
                 85                  90                  95

Val Ser Arg Val Gln Val Lys Ser Ser Ala Glu Arg Leu Arg Arg Arg
            100                 105                 110

Ser Ile Lys Lys Gly Trp Leu Thr Glu Glu Ala Arg Gln Arg Ile
            115                 120                 125

Pro Ile Ser Lys Glu Gln Arg Thr His Leu Pro Phe Leu Leu Val Lys
130                 135                 140

Ser Leu Ser Ser Arg Gln Thr Phe Pro Leu Phe Ile Glu Gln Gly Pro
145                 150                 155                 160
```

```
Ile Glu Asp Lys Pro Thr Pro Gly Val Phe Ser Ser Tyr Gly Leu Ser
            165                 170                 175

Ala Ser Ala Thr Ile Pro Trp Phe
            180

<210> SEQ ID NO 16
<211> LENGTH: 29
<212> TYPE: RNA
<213> ORGANISM: Artificial Sequence
<220> FEATURE:
<223> OTHER INFORMATION: Synthetic oligonucleotide

<400> SEQUENCE: 16
guucacuguc guacaggcag cuuagaaaa                                          29

<210> SEQ ID NO 17
<211> LENGTH: 28
<212> TYPE: RNA
<213> ORGANISM: Artificial Sequence
<220> FEATURE:
<223> OTHER INFORMATION: Synthetic oligonucleotide

<400> SEQUENCE: 17
gugcacugcc guacaggcag cuuagaaa                                           28

<210> SEQ ID NO 18
<211> LENGTH: 24
<212> TYPE: RNA
<213> ORGANISM: Artificial Sequence
<220> FEATURE:
<223> OTHER INFORMATION: Synthetic oligonucleotide

<400> SEQUENCE: 18
acugccguac aggcaguuua gaaa                                               24

<210> SEQ ID NO 19
<211> LENGTH: 28
<212> TYPE: RNA
<213> ORGANISM: Artificial Sequence
<220> FEATURE:
<223> OTHER INFORMATION: Synthetic oligonucleotide

<400> SEQUENCE: 19
guucacugcc gcacaggcag cuuagaaa                                           28

<210> SEQ ID NO 20
<211> LENGTH: 28
<212> TYPE: RNA
<213> ORGANISM: Artificial Sequence
<220> FEATURE:
<223> OTHER INFORMATION: Synthetic oligonucleotide

<400> SEQUENCE: 20
guguacugcc guacaggcag cuuagaaa                                           28

<210> SEQ ID NO 21
<211> LENGTH: 28
<212> TYPE: RNA
<213> ORGANISM: Artificial Sequence
<220> FEATURE:
<223> OTHER INFORMATION: Synthetic oligonucleotide

<400> SEQUENCE: 21
guucacugcc guacaggcag cuuagaaa                                           28
```

<210> SEQ ID NO 22
<211> LENGTH: 184
<212> TYPE: PRT
<213> ORGANISM: Dickeya dadantii

<400> SEQUENCE: 22

```
Met Asp His Tyr Ile Glu Ile Arg Val Leu Pro Asp Pro Glu Phe Ser
1               5                   10                  15

Gly Val Gln Leu Leu Ser Ala Leu Phe Ala Lys Leu His Arg Ala Leu
            20                  25                  30

Gly Gln Arg Ala Thr Gly Ala Ile Gly Val Ser Phe Pro Asp Ala Gly
        35                  40                  45

Lys Thr Leu Gly Glu Arg Leu Arg Leu His Gly Ser Val Gln Glu Leu
50                  55                  60

Ala Ala Leu Glu Gln Thr Gly Trp Leu Arg Gly Leu Arg Asp Tyr Thr
65                  70                  75                  80

Ala Ile Thr Glu Pro Leu Pro Val Pro Ala Gly Val Lys His Arg Thr
                85                  90                  95

Val Arg Arg Val Gln Val Lys Ser Ser Ala Glu Arg Leu Arg Arg Arg
            100                 105                 110

Ala Val Asn Lys Gly Arg Met Thr Val Asp Glu Ala Asp Ala Arg Ile
        115                 120                 125

Pro Tyr Thr Val Glu Lys Arg Thr Ser Leu Pro Tyr Leu Pro Leu Arg
    130                 135                 140

Ser Leu Ser Asn Gly Gln Thr Phe Leu Leu Phe Val Glu His Gly Pro
145                 150                 155                 160

Leu Gln Asp Lys Pro Val Ala Gly Ala Phe Ser Ser Tyr Gly Leu Ser
                165                 170                 175

Ala Val Ala Thr Ile Pro Trp Phe
            180
```

<210> SEQ ID NO 23
<211> LENGTH: 28
<212> TYPE: RNA
<213> ORGANISM: Artificial Sequence
<220> FEATURE:
<223> OTHER INFORMATION: Synthetic oligonucleotide

<400> SEQUENCE: 23
guucacugcc guguaggcag cuuagaaa                                            28

<210> SEQ ID NO 24
<211> LENGTH: 188
<212> TYPE: PRT
<213> ORGANISM: Xanthomonas albilineans

<400> SEQUENCE: 24

```
Met Gln His Tyr Leu Asp Leu His Leu Arg Pro Asp Pro Glu Leu Ala
1               5                   10                  15

Pro Tyr Gln Leu Leu Gly Ala Leu Tyr Ala Arg Leu His Arg Ser Leu
            20                  25                  30

Val Thr Leu Asn Thr Thr Arg Ile Gly Val Ser Phe Pro Gly His Asp
        35                  40                  45

Asn Arg Val Pro Thr Leu Gly Thr His Leu Arg Leu His Gly Asp Asp
    50                  55                  60

Ser Thr Leu His His Leu Met Ala Thr Thr Trp Leu His Gly Val Arg
65                  70                  75                  80
```

```
Asp His Val Thr Ile Thr Ser Ile Gly Ala Val Pro Ser Glu Ala Val
                85                  90                  95

His Arg Gln Val Thr Arg Val Gln Ala Lys Ser Ser Pro Glu Arg Leu
            100                 105                 110

Arg Arg Arg Ala Met Arg Arg His Gly Ile Ser Glu Asp Leu Ala Val
            115                 120                 125

Gln Arg Ile Pro Asp Ser Ala Ala Glu Gln Leu Arg Leu Pro Phe Val
        130                 135                 140

Val Leu Gly Ser Arg Ser Thr Gly Gln Thr Ala Phe Pro Val Phe Val
145                 150                 155                 160

Arg His Gly Pro Val Gln Gln Glu Pro Val Pro Gly Asp Phe Ser Ser
                165                 170                 175

Tyr Gly Leu Ser Arg Gly Ala Thr Val Pro Trp Phe
            180                 185

<210> SEQ ID NO 25
<211> LENGTH: 28
<212> TYPE: RNA
<213> ORGANISM: Artificial Sequence
<220> FEATURE:
<223> OTHER INFORMATION: Synthetic oligonucleotide

<400> SEQUENCE: 25
guucacugcc guguaggcag cucagaaa                                      28

<210> SEQ ID NO 26
<211> LENGTH: 27
<212> TYPE: RNA
<213> ORGANISM: Artificial Sequence
<220> FEATURE:
<223> OTHER INFORMATION: Synthetic oligonucleotide

<400> SEQUENCE: 26
uucacugccg uguaggcagc ucagaaa                                       27

<210> SEQ ID NO 27
<211> LENGTH: 28
<212> TYPE: RNA
<213> ORGANISM: Artificial Sequence
<220> FEATURE:
<223> OTHER INFORMATION: Synthetic oligonucleotide

<400> SEQUENCE: 27
guucacugcc guauaggcag cucagaaa                                      28

<210> SEQ ID NO 28
<211> LENGTH: 184
<212> TYPE: PRT
<213> ORGANISM: Pectobacterium atrosepticum

<400> SEQUENCE: 28

Met Asp His Tyr Ile Asp Ile Arg Val Gln Pro Asp Pro Glu Phe Thr
1               5                   10                  15

Ala Ser Gln Leu Leu Asn Ala Leu Phe Ala Lys Leu His Arg Val Leu
            20                  25                  30

Gly Gln Leu Ala Asn Gly Lys Ile Gly Ile Ser Phe Pro Glu Val Gly
        35                  40                  45

Lys Thr Leu Gly Glu Cys Leu Arg Leu His Gly Thr Glu Asp Ala Leu
    50                  55                  60

Ser Thr Leu Glu Lys Thr Ser Trp Leu Lys Gly Leu Arg Asp Tyr Thr
65                  70                  75                  80
```

```
Gln Val Ser Glu Cys Lys Val Pro Asn Gly Val Lys Phe Arg Thr
            85                  90                  95

Val Arg Arg Val Gln Leu Lys Ser Ser Ala Glu Arg Leu Arg Arg Arg
        100                 105                 110

Ser Val Ser Lys Gly Trp Leu Thr Ala Ala Glu Ala Ala Arg Ile
        115                 120                 125

Pro Asp Ala Val Glu Lys Arg Ser Ala Leu Pro Phe Val Gln Ile Lys
130                 135                 140

Ser Leu Ser Asn Gly Gln Met Phe Phe Val Phe Val Glu His Gly Pro
145                 150                 155                 160

Leu Gln Asn Ala Pro Thr Ala Gly Arg Phe Ser Tyr Gly Leu Ser
                165                 170                 175

Thr Glu Ala Thr Val Pro Trp Phe
            180

<210> SEQ ID NO 29
<211> LENGTH: 184
<212> TYPE: PRT
<213> ORGANISM: Photorhabdus luminescens

<400> SEQUENCE: 29

Met Asp Tyr Tyr Leu Glu Ile Arg Val Leu Pro Asp Leu Glu Phe Ser
1               5                   10                  15

Gln Gln Ser Leu Phe Glu Ala Leu Phe Ala Lys Leu His Arg Ala Leu
            20                  25                  30

Gly Gln Leu Ser Asn Gly Gln Val Gly Val Ser Phe Pro Cys Ala Arg
        35                  40                  45

Lys Thr Leu Gly Asp Thr Leu Arg Ile His Gly Ser Ser Glu Ala Leu
50                  55                  60

Asn Asp Leu Gln Ala Leu Pro Trp Leu Lys Gly Leu Arg Asp Tyr Thr
65                  70                  75                  80

Glu Val Ile Asp Ile Gln Pro Ile Pro Gln Glu Thr Lys Tyr Arg Cys
                85                  90                  95

Val Ser Arg Val Gln Val Lys Ser Ser Ala Glu Arg Leu Arg Arg Arg
            100                 105                 110

Ala Ile Lys Lys Gly Trp Leu Thr Gly Glu Gln Ala Arg Gln Arg Ile
        115                 120                 125

Pro Ile Ser Lys Glu Gln Arg Thr His Leu Pro Phe Leu Phe Leu Lys
130                 135                 140

Ser Leu Ser Ser Gly Gln Ser Phe Leu Leu Phe Val Lys Gln Gly Pro
145                 150                 155                 160

Ile Gln Asp Lys Pro Thr Ser Gly Ile Phe Ser Ser Tyr Gly Leu Ser
                165                 170                 175

Ser Ser Ala Thr Ile Pro Trp Phe
            180

<210> SEQ ID NO 30
<211> LENGTH: 188
<212> TYPE: PRT
<213> ORGANISM: Desulfurivibrio alkaliphilus

<400> SEQUENCE: 30

Met Val Met Ala Met Asp Cys Tyr Val Glu Ile Ser Leu Leu Pro Asp
1               5                   10                  15

Pro Glu Phe Pro Asp Ser Ile Leu Met Asn Ala Leu Phe Ala Lys Leu
            20                  25                  30
```

His Arg Ala Leu Ala Glu Asn Gly Lys Gln Glu Ile Gly Val Ser Phe
    35                  40                  45

Pro Glu Phe Gly Lys Lys Leu Asn Ser Lys Leu Arg Ile His Gly Ser
 50                  55                  60

Glu Glu Ser Leu Lys Arg Leu Met Asp Leu Asn Trp Ile Gln Gly Met
65                  70                  75                  80

Lys Asp Tyr Thr Arg Val Ser Gly Ile Ala Lys Val Pro Asp Ser Cys
                85                  90                  95

Gln Tyr Arg Thr Val Lys Arg Val Gln Ala Lys Ser Ser Val Asp Arg
            100                 105                 110

Leu Tyr Arg Arg Ser Val Lys Lys Gly Trp Leu Ser Glu Glu Asn Ala
            115                 120                 125

Glu Gln Gln Lys Glu Arg Ala Arg Glu Gly Arg Leu Lys Leu Pro Phe
        130                 135                 140

Val Gln Leu Lys Ser Gln Thr Thr Gly Gln Gln Phe Arg Leu Phe Ile
145                 150                 155                 160

Gln His Gly Ser Leu Gln Glu Lys Pro Val Thr Gly Arg Phe Ser Ser
                165                 170                 175

Tyr Gly Leu Ser Asn Glu Ala Thr Val Pro Trp Phe
            180                 185

<210> SEQ ID NO 31
<211> LENGTH: 28
<212> TYPE: RNA
<213> ORGANISM: Artificial Sequence
<220> FEATURE:
<223> OTHER INFORMATION: Synthetic oligonucleotide

<400> SEQUENCE: 31
guucacugcc gcacaggcag cucagaaa                                            28

<210> SEQ ID NO 32
<211> LENGTH: 184
<212> TYPE: PRT
<213> ORGANISM: Dickeya zeae

<400> SEQUENCE: 32

Met Asp His Tyr Ile Glu Ile Arg Val Leu Pro Asp Leu Glu Phe Ser
1               5                   10                  15

Ala Val Gln Leu Leu Ser Ala Leu Phe Ala Lys Leu His Arg Ala Leu
                20                  25                  30

Gly Gln Gln Ala Thr Gly Ala Ile Gly Val Ser Phe Pro Asp Val Gly
            35                  40                  45

Lys Thr Leu Gly Glu Arg Leu Arg Leu His Gly Ser Glu Gln Ala Leu
 50                  55                  60

Thr Ala Leu Glu Gln Thr Gly Trp Arg Thr Gly Leu Arg Asp Tyr Ser
65                  70                  75                  80

Thr Ile Thr Asp Val Leu Thr Val Pro Thr Gly Ala Gln Tyr Arg Thr
                85                  90                  95

Val Arg Arg Val Gln Val Lys Ser Ser Ala Glu Arg Leu Arg Arg Arg
            100                 105                 110

Ala Val Ser Lys Gly Trp Leu Thr Ala Asp Glu Ala Ala Arg Ile
            115                 120                 125

Pro Tyr Ala Val Glu Lys Arg Thr Ser Leu Pro Tyr Leu Pro Leu Arg
        130                 135                 140

Ser Leu Ser Ser Gly Gln Pro Phe Leu Leu Phe Val Glu His Gly Pro

```
145                 150                 155                 160
Leu Gln Asp Lys Pro Val Ala Gly Thr Phe Ser Ser Tyr Gly Leu Ser
                165                 170                 175

Ala Thr Ala Thr Ile Pro Trp Phe
            180

<210> SEQ ID NO 33
<211> LENGTH: 28
<212> TYPE: RNA
<213> ORGANISM: Artificial Sequence
<220> FEATURE:
<223> OTHER INFORMATION: Synthetic oligonucleotide

<400> SEQUENCE: 33
gugcacugcc guauaggcag cuuagaaa                                          28

<210> SEQ ID NO 34
<211> LENGTH: 184
<212> TYPE: PRT
<213> ORGANISM: Yersinia pestis

<400> SEQUENCE: 34

Met Asp His Tyr Leu Asp Ile Arg Val Leu Pro Asp Pro Glu Phe Ser
1               5                   10                  15

Ala Gln Thr Leu Leu Glu Ala Leu Phe Ala Lys Leu His Arg Ala Leu
            20                  25                  30

Val Ala Thr Ile Pro Gly Arg Val Gly Val Ser Phe Pro Thr Ala Gly
        35                  40                  45

Lys Thr Leu Gly Ser Gln Leu Arg Leu His Gly Ser Arg Gly Asp Leu
    50                  55                  60

Leu Glu Leu Gln Ser Ala Gly Trp Leu Lys Gly Leu Gln Asp Tyr Cys
65                  70                  75                  80

Glu Cys Ser Glu Ile Leu Pro Val Pro Ala Asp Val Lys His Arg Thr
                85                  90                  95

Ile Arg Arg Val Gln Val Lys Ser Ser Ala Gln Arg Leu Arg Arg Arg
            100                 105                 110

Ser Val Ser Lys Gly Trp Leu Thr Glu Glu Gln Ala Arg Leu Arg Ile
        115                 120                 125

Pro Asp Ser His Asp Lys Arg Cys Asp Leu Pro Phe Leu Arg Leu Lys
    130                 135                 140

Ser Arg Ser Ser Glu Gln Tyr Phe Leu Leu Phe Ile Glu Gln Gly Thr
145                 150                 155                 160

Leu Gln Ala Ser Ala Thr Thr Gly Glu Phe Ser Ala Tyr Gly Leu Ser
                165                 170                 175

Val Asn Ala Thr Ile Pro Trp Phe
            180

<210> SEQ ID NO 35
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 35
uguucacugc cgcacaggca gcuuagaaaa                                        30

<210> SEQ ID NO 36
<211> LENGTH: 184
```

```
<212> TYPE: PRT
<213> ORGANISM: Dickeya dadantii

<400> SEQUENCE: 36

Met Asp His Tyr Ile Glu Ile Arg Val Leu Pro Asp Pro Glu Phe Ser
1               5                   10                  15

Ala Val Gln Leu Leu Ser Ala Leu Phe Ala Lys Leu His Arg Ala Leu
            20                  25                  30

Gly Gln Arg Ala Thr Gly Asp Ile Gly Val Ser Phe Pro Asp Ala Gly
        35                  40                  45

Lys Thr Leu Gly Glu Arg Leu Arg Leu His Gly Ser Val Gln Ala Leu
    50                  55                  60

Ala Ala Leu Glu Gln Thr Gly Trp Leu Lys Gly Leu Arg Asp Tyr Ser
65                  70                  75                  80

Thr Ile Thr Asp Val Leu Thr Val Pro Thr Gly Ala Gln Tyr Arg Thr
                85                  90                  95

Val Arg Arg Val Gln Val Lys Ser Ser Ala Glu Arg Leu Arg Arg Arg
            100                 105                 110

Ala Val Ser Lys Gly Arg Met Thr Ala Asp Glu Ala Ala Ala Arg Ile
        115                 120                 125

Pro Tyr Ala Ala Glu Lys Arg Thr Ser Leu Pro Tyr Leu Pro Leu Arg
    130                 135                 140

Ser Leu Ser Ser Gly Gln Thr Phe Leu Leu Phe Val Glu His Gly Pro
145                 150                 155                 160

Leu Gln Glu Lys Pro Val Ala Gly Val Phe Ser Ser Tyr Gly Leu Ser
                165                 170                 175

Ala Ile Ala Thr Ile Pro Trp Phe
            180

<210> SEQ ID NO 37
<211> LENGTH: 28
<212> TYPE: RNA
<213> ORGANISM: Artificial Sequence
<220> FEATURE:
<223> OTHER INFORMATION: Synthetic oligonucleotide

<400> SEQUENCE: 37
gugaacugcc gcauaggcag cuuagaaa                                      28

<210> SEQ ID NO 38
<211> LENGTH: 198
<212> TYPE: PRT
<213> ORGANISM: Escherichia coli

<400> SEQUENCE: 38

Met Ala Val Ser Leu Val Arg Asn Arg Asn Lys Glu Leu Pro Met Asp
1               5                   10                  15

His Tyr Leu Glu Ile Arg Val Leu Pro Asp Pro Glu Phe Ser Ser Glu
            20                  25                  30

Met Leu Met Ala Ala Leu Phe Ala Lys Leu His Arg Val Leu Gly Ala
        35                  40                  45

Arg Gly Gln Gly Asp Ile Gly Val Ser Phe Pro Asp Val Asn Val Met
    50                  55                  60

Pro Gly Ala Arg Leu Arg Leu His Gly Ser Ala Gln Ala Leu Gln Ala
65                  70                  75                  80

Leu Glu Ala Ser Thr Trp Arg Lys Gly Leu Thr Asp Tyr Cys Gln Cys
                85                  90                  95
```

```
Ser Pro Val Thr Pro Val Pro Glu Ile Lys Gly Trp Arg Val Ser
            100                 105                 110

Arg Val Gln Val Lys Ser Asn Pro Gln Arg Leu Leu Arg Ser Val
            115                 120                 125

Lys Lys Gly Trp Leu Thr Glu Glu Gln Ala Ile Glu Arg Leu Ala Thr
            130                 135                 140

Gln Ala Glu Gln Arg Thr Asp Leu Pro Phe Leu Asn Met Lys Ser Leu
145                 150                 155                 160

Ser Ser Gln Gln Leu Phe Lys Leu Phe Ile Arg His Gly Asp Leu Leu
                    165                 170                 175

Lys Glu Pro Val Lys Gly Glu Phe Ser Ser Tyr Gly Leu Ser Ala Thr
            180                 185                 190

Ala Thr Ile Pro Trp Phe
            195

<210> SEQ ID NO 39
<211> LENGTH: 184
<212> TYPE: PRT
<213> ORGANISM: Escherichia coli

<400> SEQUENCE: 39

Met Asp His Tyr Leu Glu Ile Arg Val Leu Pro Asp Pro Glu Phe Ser
1               5                   10                  15

Ser Glu Met Leu Met Ala Ala Leu Phe Ala Lys Leu His Arg Val Leu
            20                  25                  30

Gly Ala Arg Gly Gln Gly Asp Ile Gly Val Ser Phe Pro Asp Val Asn
        35                  40                  45

Val Met Pro Gly Ala Arg Leu Arg Leu His Gly Ser Ala Gln Ala Leu
50                  55                  60

Gln Ala Leu Glu Ala Ser Thr Trp Arg Lys Gly Leu Thr Asp Tyr Cys
65                  70                  75                  80

Gln Cys Ser Pro Val Thr Pro Val Pro Glu Ile Lys Gly Trp Arg Val
            85                  90                  95

Val Ser Arg Val Gln Val Lys Ser Asn Pro Gln Arg Leu Leu Arg Arg
            100                 105                 110

Ser Val Lys Lys Gly Trp Leu Thr Glu Glu Gln Ala Ile Glu Arg Leu
            115                 120                 125

Ala Thr Gln Ala Glu Gln Arg Thr Asp Leu Pro Phe Leu Asn Met Lys
            130                 135                 140

Ser Leu Ser Ser Gln Gln Leu Phe Lys Leu Phe Ile Arg His Gly Asp
145                 150                 155                 160

Leu Leu Lys Glu Pro Val Lys Gly Glu Phe Ser Ser Tyr Gly Leu Ser
                    165                 170                 175

Ala Thr Ala Thr Ile Pro Trp Phe
            180

<210> SEQ ID NO 40
<211> LENGTH: 184
<212> TYPE: PRT
<213> ORGANISM: Tolumonas auensis

<400> SEQUENCE: 40

Met Asp His Tyr Leu Asp Ile Arg Leu Leu Pro Glu Glu Pro Glu Val
1               5                   10                  15

Ser Glu Ser Phe Leu Leu Asn Ala Leu Phe Ala Lys Leu His Val Arg
            20                  25                  30
```

Leu Gly Gln Gln Ala Gln Gly Arg Val Gly Val Ser Phe Pro Asp His
             35                  40                  45

His Lys Arg Leu Gly Asp Leu Leu Arg Leu His Gly Gln Arg Thr Asp
 50                  55                  60

Leu Gln Ala Leu Met Ala Asp Asp Trp Leu Gln Gly Leu Lys Gly Tyr
 65                  70                  75                  80

Thr Gln Cys Ser Glu Val Leu Pro Ile Pro Ala Thr Val Ser Tyr Arg
                 85                  90                  95

Ala Val Lys Arg Val Gln Ala Lys Ser Ala His Asn Lys Arg Gln Arg
                100                 105                 110

Ser Ile Ala Lys Gly Trp Leu Thr Glu Ser Glu Ala Gln Ile Arg Ile
            115                 120                 125

Pro Asp Thr Gln Gln Lys Glu Leu His Leu Pro Phe Val Gln Leu Lys
130                 135                 140

Ser Arg Ser Asn Gly Gln Met Met Arg Val Tyr Val Glu His Gly Pro
145                 150                 155                 160

Val Leu Ala Val Pro Val Ser Gly Tyr Phe Asn Ala Tyr Gly Leu Ser
                165                 170                 175

Ser Ile Ala Thr Ile Pro Trp Phe
            180

<210> SEQ ID NO 41
<211> LENGTH: 28
<212> TYPE: RNA
<213> ORGANISM: Artificial Sequence
<220> FEATURE:
<223> OTHER INFORMATION: Synthetic oligonucleotide

<400> SEQUENCE: 41
cuucacugcc gcacaggcag cuuagaaa                                          28

<210> SEQ ID NO 42
<211> LENGTH: 184
<212> TYPE: PRT
<213> ORGANISM: Erwinia pyrifoliae

<400> SEQUENCE: 42

Met Asp His Tyr Gln Asp Ile Arg Val Arg Val Asp Glu Glu Asn Gly
 1               5                  10                  15

Glu Ala Val Leu Leu Ala Gln Val Phe Met His Leu His Gln Val Leu
                 20                  25                  30

Met Arg Ala Ala Asn Gly Arg Ile Gly Ile Ser Phe Pro Asn Val Lys
             35                  40                  45

Arg Thr Leu Gly Asp Arg Ile Arg Leu His Gly Thr Leu Asp Asp Leu
 50                  55                  60

Ser Ala Leu Gln Gln Ser Gly Trp Asn Lys Cys Leu Arg Asp Tyr Ile
 65                  70                  75                  80

Ala Cys Ser Asp Ile Ala Pro Val Pro Lys Gly Ala Ala Trp Arg Thr
                 85                  90                  95

Val Arg Arg Val Gln Val Lys Ser Ser Ala Glu Arg Leu Arg Arg Arg
                100                 105                 110

Ser Val Asn Lys Gly Trp Leu Ser Glu Gln Glu Ala Ala Glu Arg Ile
            115                 120                 125

Ser Val Leu Asn Glu Gln Arg Ser Asn Leu Pro Phe Leu Gln Ile Lys
130                 135                 140

Ser Gly Ser Asn Gly Gln Ala Trp Arg Leu Phe Ile Glu His Gly Ser
145                 150                 155                 160

```
Leu Val Ser Ala Pro Ser Asp Gly Ser Phe Ser Ser Tyr Gly Leu Ser
            165                 170                 175

Ala Ala Ala Thr Ile Pro Trp Phe
        180

<210> SEQ ID NO 43
<211> LENGTH: 28
<212> TYPE: RNA
<213> ORGANISM: Artificial Sequence
<220> FEATURE:
<223> OTHER INFORMATION: Synthetic oligonucleotide

<400> SEQUENCE: 43
uucacugccg uacaggcagc uuagaaaa                                              28

<210> SEQ ID NO 44
<211> LENGTH: 198
<212> TYPE: PRT
<213> ORGANISM: Escherichia coli

<400> SEQUENCE: 44

Met Ala Val Ser Leu Val Arg Asn Arg Asn Lys Glu Leu Pro Met Asp
1               5                   10                  15

His Tyr Leu Glu Ile Arg Val Leu Pro Asp Pro Glu Phe Ser Ser Glu
            20                  25                  30

Met Leu Met Ala Ala Leu Phe Ala Lys Leu His Arg Val Leu Gly Ala
        35                  40                  45

Arg Gly Gln Gly Asp Ile Gly Val Ser Phe Pro Asp Val Asn Val Met
    50                  55                  60

Pro Gly Thr His Leu Arg Leu His Gly Ser Ala Gln Ala Leu Gln Glu
65                  70                  75                  80

Leu Glu Ala Ser Thr Trp Arg Lys Gly Leu Thr Asp Tyr Cys Gln Cys
                85                  90                  95

Ser Pro Val Thr Pro Val Pro Glu Ile Lys Gly Trp Arg Val Val Ser
            100                 105                 110

Arg Val Gln Val Lys Ser Asn Pro Gln Arg Leu Leu Arg Arg Ser Val
        115                 120                 125

Lys Lys Gly Trp Leu Thr Glu Glu Gln Ala Ile Glu Arg Leu Ala Thr
    130                 135                 140

Gln Ala Glu Gln Arg Thr Asp Leu Pro Phe Leu Asn Met Lys Ser Leu
145                 150                 155                 160

Ser Ser Gln Gln Gln Phe Lys Leu Phe Ile Arg His Gly Asp Leu Leu
                165                 170                 175

Lys Glu Pro Val Lys Gly Glu Phe Ser Ser Tyr Gly Leu Ser Ala Thr
            180                 185                 190

Ala Thr Ile Pro Trp Phe
        195

<210> SEQ ID NO 45
<211> LENGTH: 190
<212> TYPE: PRT
<213> ORGANISM: Verminephrobacter eiseniae

<400> SEQUENCE: 45

Met Ser Thr His Tyr Ile Asp Ile Thr Leu Arg Pro Asp Pro Glu Phe
1               5                   10                  15

Ser Pro Ala His Leu Leu Asn Ala Leu His Ala Gln Leu His Leu Ala
            20                  25                  30
```

Leu Val Gln Leu Gly Thr Gly Asp Val Gly Val Ser Phe Pro Gly Phe
            35                  40                  45

Ile Leu Arg Gly Glu His Ser His Leu Gly Thr Thr Leu Arg Leu His
 50                  55                  60

Gly Ala Thr Ser Ala Leu Gln Arg Leu Gln Ala Leu Ser Trp Leu Arg
 65                  70                  75                  80

Gly Met Arg Asp His Val Lys Thr Ser Glu Val Ala Pro Val Pro Thr
                 85                  90                  95

His Thr Gln His Arg Val Val Arg Arg Val Gln Ala Lys Ser Ser Pro
            100                 105                 110

Glu Arg Ser Arg Arg Arg Leu Met Arg Arg Leu Glu Ile Asp Glu Ala
        115                 120                 125

Gln Ala Leu Gln Arg Ile Pro Asp Gln Glu Gly Arg Arg Leu Ala Leu
    130                 135                 140

Pro Tyr Leu Arg Leu Gln Ser Ala Ser Lys Gly Gln Val Phe Arg Leu
145                 150                 155                 160

Phe Ile Glu His Gly Pro Leu Leu Asp Thr Pro Ser Pro Gly Ser Phe
                165                 170                 175

Gly Thr Tyr Gly Leu Ser Thr Gln Ala Thr Ile Pro Trp Phe
            180                 185                 190

<210> SEQ ID NO 46
<211> LENGTH: 28
<212> TYPE: RNA
<213> ORGANISM: Artificial Sequence
<220> FEATURE:
<223> OTHER INFORMATION: Synthetic oligonucleotide

<400> SEQUENCE: 46
guucacugcc ggauaggcag cucagaaa                                              28

<210> SEQ ID NO 47
<211> LENGTH: 195
<212> TYPE: PRT
<213> ORGANISM: Chromobacterium violaceum

<400> SEQUENCE: 47

Met Asp His Tyr Leu Asp Ile Arg Leu Leu Pro Asp Ala Asp Phe Gly
 1               5                  10                  15

Pro Pro Val Leu Met Asn Ala Leu Tyr Ala Lys Leu His Arg Ala Leu
             20                  25                  30

Ala Ala Gln Gln Arg Gln Asp Ile Gly Val Ser Phe Pro Gly Tyr Asp
         35                  40                  45

Pro Ala Pro Ser Ser His Asp Gly Lys Pro Leu Pro Pro Thr Leu Gly
     50                  55                  60

Leu Thr Leu Arg Leu His Gly Ser Ala Ala Leu Asp Gly Leu Met
 65                  70                  75                  80

Ala Arg Arg Trp Leu Ser Gly Phe Ala Asp His Ala Ile Val Gly Asp
                 85                  90                  95

Ile Arg Pro Val Pro Ala Gly Ala Ser Ala Val Ser Val Arg Arg Arg
            100                 105                 110

Gln Ala Lys Ser Ser Pro Ala Arg Ala Arg Asp Arg Leu Met Arg Arg
        115                 120                 125

Gln Gly Ile Ser Ala Glu Glu Ala Arg Arg Ile Pro Asp Glu Thr
    130                 135                 140

Ala Gln Arg Leu Asn Leu Pro Tyr Leu Thr Val Asp Ser Ala Ser Thr

```
                145                 150                 155                 160
Gly Gln Cys Phe Arg Leu Phe Val Glu Gln Gln Ala Ala Pro Ser Ile
                    165                 170                 175

Ala Ala Gly Ser Phe Asn Ala Tyr Gly Leu Ser Ala Ala Ala Ala Leu
                180                 185                 190

Pro Ala Trp
        195

<210> SEQ ID NO 48
<211> LENGTH: 28
<212> TYPE: RNA
<213> ORGANISM: Artificial Sequence
<220> FEATURE:
<223> OTHER INFORMATION: Synthetic oligonucleotide

<400> SEQUENCE: 48
guucacugcc ggauaggcag cuuagaaa                                             28

<210> SEQ ID NO 49
<211> LENGTH: 184
<212> TYPE: PRT
<213> ORGANISM: Erwinia tasmaniensis

<400> SEQUENCE: 49

Met Asp Arg Tyr Gln Asp Ile Arg Val Arg Val Asp Ala Glu Met Thr
1               5                   10                  15

Ala Pro Val Leu Leu Ala Gln Val Phe Met Arg Leu His Gln Val Leu
                20                  25                  30

Met Arg Ala Ala Asn Gly Arg Ile Gly Ile Ser Phe Pro Asp Val Lys
            35                  40                  45

Leu Thr Leu Gly Asp Arg Ile Arg Leu His Gly Thr Leu Asp Asp Leu
        50                  55                  60

Ser Ser Leu Gln Gln Ser Gly Trp Asp Lys Gly Leu Thr Asp Tyr Ile
65                  70                  75                  80

Ala Cys Ser Ala Ile Asp Pro Val Pro Pro Gly Ala Ala Trp Arg Thr
                85                  90                  95

Val Arg Arg Val Gln Val Lys Ser Ser Ala Glu Arg Leu Arg Arg Arg
            100                 105                 110

Ser Val Asn Lys Gly Trp Leu Asn Glu Ala Glu Ala Ala Glu Arg Ile
        115                 120                 125

Asn Val Leu Ser Glu Gln Arg Ser Asp Leu Pro Tyr Leu Gln Ile Lys
    130                 135                 140

Ser Gly Ser Asn Gly His Ala Trp Arg Leu Phe Ile Glu His Gly Pro
145                 150                 155                 160

Leu Val Ser Val Pro Val Asn Gly Gly Phe Ser Ser Tyr Gly Leu Ser
                165                 170                 175

Ala Thr Ala Thr Val Pro Trp Phe
            180

<210> SEQ ID NO 50
<211> LENGTH: 28
<212> TYPE: RNA
<213> ORGANISM: Artificial Sequence
<220> FEATURE:
<223> OTHER INFORMATION: Synthetic oligonucleotide

<400> SEQUENCE: 50
guucacugcc guacaggcag cuuagaag                                             28
```

<210> SEQ ID NO 51
<211> LENGTH: 190
<212> TYPE: PRT
<213> ORGANISM: Delftia acidovorans

<400> SEQUENCE: 51

```
Met Ala Met Thr Ser His Tyr Ile Asp Thr Thr Leu Leu Pro Asp Pro
1               5                   10                  15

Glu Phe Ser His Ala His Leu Leu Gly Ala Leu Val Ala Lys Leu His
            20                  25                  30

Arg Ala Leu Val Gln Leu Gly Ser Thr Asp Ile Gly Ile Ser Phe Pro
        35                  40                  45

Gly Tyr Ser Leu Arg Pro Arg Thr Leu Gly Thr Ile Leu Arg Leu His
    50                  55                  60

Gly Ser Glu Ala Ala Leu Arg Gly Leu Met Glu Gln Pro Trp Leu Gln
65                  70                  75                  80

Gly Met Arg Asp His Val His Cys Thr Pro Pro Ala Leu Val Pro Glu
                85                  90                  95

Gly Ala Val Pro Cys Leu Val Gln Arg Gln Phe Lys Thr Ser Pro
            100                 105                 110

Asp Arg Leu Arg Arg Arg Met Arg Arg Lys Gly Glu Thr Ala Glu
        115                 120                 125

Gln Ala Ala Ala Ile Pro Asp Ser Val Glu Arg Thr Pro Asp Leu
    130                 135                 140

Pro Tyr Val Gln Leu Arg Ser Ala Ser Thr Gly Gln Pro Phe Cys Leu
145                 150                 155                 160

Phe Val Glu Gln Lys Ala Val Gln Gly Thr Ala Gly Gln Glu Gly Phe
                165                 170                 175

Asn Thr Tyr Gly Leu Ser Leu Gly Thr Ala Val Pro Trp Phe
            180                 185                 190
```

<210> SEQ ID NO 52
<211> LENGTH: 28
<212> TYPE: RNA
<213> ORGANISM: Artificial Sequence
<220> FEATURE:
<223> OTHER INFORMATION: Synthetic oligonucleotide

<400> SEQUENCE: 52
guucgcugcc gcguaggcag cucagaaa                                      28

<210> SEQ ID NO 53
<211> LENGTH: 184
<212> TYPE: PRT
<213> ORGANISM: Enterobacter sp. 638

<400> SEQUENCE: 53

```
Met Asp His Tyr Leu Glu Ile Arg Val Leu Ser Asp Pro Glu Phe Ser
1               5                   10                  15

Glu Glu Thr Leu Met Ala Ala Leu Phe Ala Lys Leu His Arg Ala Leu
            20                  25                  30

Gly Ala Arg Gly Gln Gly Asp Ile Gly Val Ser Phe Pro Arg Tyr Ser
        35                  40                  45

Leu Lys Pro Gly Asp Thr Leu Arg Leu His Gly Ser Ala Gln Ser Leu
    50                  55                  60

Asp Glu Leu Glu Lys Met Ala Trp Arg Lys Gly Leu Ser Asp Tyr Cys
65                  70                  75                  80
```

```
Leu Cys Lys Gly Val Leu Pro Ala Pro Asp Val Asn Ala Trp Arg Cys
                85                  90                  95

Val Ser Arg Val Gln Val Lys Ser Ser Pro Gln Arg Leu Met Arg Arg
            100                 105                 110

Ser Val Lys Lys Gly Trp Leu Thr Glu Glu Ala Gln Gln Arg Leu
            115                 120                 125

Leu Asn Leu Gln Glu Ala Arg Thr Asp Leu Pro Trp Leu Asn Leu Gln
        130                 135                 140

Ser Leu Ser Thr Gly Gln Ser Phe Arg Leu Phe Ile Arg His Gly Asp
145                 150                 155                 160

Ile Val Asp Met Pro Met Cys Gly Glu Phe Ser Ser Tyr Gly Leu Ser
                165                 170                 175

Ala Thr Ala Thr Ile Pro Trp Phe
            180

<210> SEQ ID NO 54
<211> LENGTH: 186
<212> TYPE: PRT
<213> ORGANISM: Thioalkalivibrio sp. K90mix

<400> SEQUENCE: 54

Met Asp His Tyr Leu Asp Leu Arg Val Met Pro Asp Pro Glu Phe Lys
1               5                   10                  15

Glu Thr Thr Leu Leu Gly Ala Leu Val Ser Lys Leu His Arg Arg Leu
            20                  25                  30

Val Ser Met Ser Ala Asp Asp Ile Gly Ile Ser Leu Pro Asp His Glu
        35                  40                  45

Gln Glu Pro Pro Leu Gly Arg Arg Leu Arg Val His Gly Thr Gln Gly
    50                  55                  60

Arg Leu Asn Leu Leu Met Gln Asp Glu Trp Leu Gly Gly Met Gln Ser
65                  70                  75                  80

Leu Val Asp Ala Thr Pro Val Gln Pro Val Pro Asp Gln Val Thr Tyr
                85                  90                  95

Arg Pro Val Arg Arg Arg Gln Tyr Lys Thr Asn Ala Glu Arg Leu Arg
            100                 105                 110

Arg Arg Arg Met Arg Arg His Gly Glu Ser Tyr Glu Glu Ala Arg Gln
            115                 120                 125

His Ile Pro Asp Thr Val Glu Arg Arg Val Asn Thr Pro Phe Leu Ser
        130                 135                 140

Val Gln Ser Ala Ser Thr Gly Gln Arg Phe Ser Leu Phe Ile Glu His
145                 150                 155                 160

Gly Pro Pro Gln Gln His Ala Ser Pro Gly Arg Phe Asn Thr Tyr Gly
                165                 170                 175

Leu Ser Gln Asp Ala Thr Val Pro Trp Phe
            180                 185

<210> SEQ ID NO 55
<211> LENGTH: 28
<212> TYPE: RNA
<213> ORGANISM: Artificial Sequence
<220> FEATURE:
<223> OTHER INFORMATION: Synthetic oligonucleotide

<400> SEQUENCE: 55
guuagcugcc gcacaggcag cucagaaa                                          28

<210> SEQ ID NO 56
```

```
<211> LENGTH: 193
<212> TYPE: PRT
<213> ORGANISM: Zymomonas mobilis

<400> SEQUENCE: 56

Met Leu Ala Asn Pro Val Asp Ser Tyr Gln Asp Ile Tyr Ile Leu Pro
1               5                   10                  15

Asn Gln Glu Ile Ala Pro His Ile Ile Met Glu Lys Leu Phe Ser Leu
                20                  25                  30

Leu His Leu Glu Leu Val Arg Leu Gly Ser Gln His Ile Gly Ile Ser
            35                  40                  45

Phe Pro Glu His Asp Asn Asn Lys Pro Cys Leu Gly Ser Arg Leu Arg
50                  55                  60

Leu His Gly Thr Gly Ala Asp Leu His Glu Leu Ala Leu Ser Gly Trp
65                  70                  75                  80

Ile Thr Arg Leu Asp Asp Tyr Leu Tyr Cys Glu Asp Ile Lys Ser Val
                85                  90                  95

Pro Glu Ile Arg Gln Tyr Cys Val Val Ser Arg Val Gln Ala Lys Ser
                100                 105                 110

Ser Pro Ala Arg Leu Arg Arg Arg Ala Ile Arg Arg His Gly Phe His
            115                 120                 125

Asp Glu Glu Ala Lys Lys Val Ile Pro Asp Thr Ala Phe Glu Arg Leu
130                 135                 140

Glu Leu Pro Phe Ile Met Thr Gly Ser Cys Ser Thr Lys Gln Pro Arg
145                 150                 155                 160

Phe Pro Val Phe Ile Ser His Lys Ile Ile Gln Asn Lys Leu Met Asn
                165                 170                 175

Gly Asn Phe Asn Ser Tyr Gly Leu Ser Leu Gly Ala Ser Val Pro Trp
                180                 185                 190

Phe

<210> SEQ ID NO 57
<211> LENGTH: 193
<212> TYPE: PRT
<213> ORGANISM: Zymomonas mobilis

<400> SEQUENCE: 57

Met Leu Ala Asn Pro Val Asp Ser Tyr Gln Asp Ile Tyr Ile Leu Pro
1               5                   10                  15

Asn Gln Glu Ile Ala Pro His Ile Ile Met Glu Lys Leu Phe Ser Leu
                20                  25                  30

Leu His Leu Glu Leu Val Arg Leu Gly Ser Gln His Ile Gly Ile Ser
            35                  40                  45

Phe Pro Glu His Asp Asn Asn Lys Pro Cys Leu Gly Ser Arg Leu Arg
50                  55                  60

Leu His Gly Ala Gly Ala Asp Leu His Glu Leu Ala Leu Ser Gly Trp
65                  70                  75                  80

Ile Thr Arg Leu Asp Asp Tyr Leu Tyr Cys Glu Asp Ile Lys Ser Val
                85                  90                  95

Pro Glu Ile Arg Gln Tyr Cys Val Val Ser Arg Val Gln Ala Lys Ser
                100                 105                 110

Ser Pro Ala Arg Leu Arg Arg Arg Ala Ile Arg Arg His Gly Phe His
            115                 120                 125

Asp Glu Glu Ala Lys Lys Val Ile Pro Asp Thr Ala Phe Glu Arg Leu
130                 135                 140
```

```
Glu Leu Pro Phe Ile Met Thr Gly Ser Cys Ser Thr Lys Gln Pro Arg
145                 150                 155                 160

Phe Pro Val Phe Ile Ser His Lys Ile Ile Gln Asp Lys Leu Met Asn
                165                 170                 175

Gly Asn Phe Asn Ser Tyr Gly Leu Ser Leu Gly Ala Ser Val Pro Trp
            180                 185                 190

Phe

<210> SEQ ID NO 58
<211> LENGTH: 191
<212> TYPE: PRT
<213> ORGANISM: Acidovorax sp. JS42

<400> SEQUENCE: 58

Met Thr Thr His Tyr Ile Asn Ile Thr Leu Leu Pro Asp Pro Glu Phe
1               5                   10                  15

Ser His Ala His Leu Leu Gly Ala Leu Val Ala Lys Leu His Arg Ala
            20                  25                  30

Leu Val Gln Gly His Thr Thr Asp Ile Gly Val Ser Tyr Pro Gln His
        35                  40                  45

Val Ser Gln Pro Leu Thr Lys Arg Thr Leu Gly Ala Val Leu Arg Leu
    50                  55                  60

His Gly Thr Pro Glu Ala Leu Gln Arg Leu Met Glu Glu Asp Trp Leu
65                  70                  75                  80

Lys Gly Met Arg Asp His Thr Gln Val Gly Glu Leu Leu Pro Val Pro
                85                  90                  95

Ala Asn Ala Gln His Arg Thr Val Arg Arg Gln Phe Lys Thr Asn
            100                 105                 110

Ala Asp Arg Leu Arg Arg Arg Met Gln Arg Lys Gly Glu Thr Ala
        115                 120                 125

Glu Gln Ala Ala Ala Ile Pro Asp Thr Val Glu Arg Arg Pro Asp
    130                 135                 140

Leu Pro Phe Val Gln Leu Arg Ser Ser Ser Thr Gly Gln Ser Phe Cys
145                 150                 155                 160

Leu Cys Val Glu His Gly Pro Leu Gln Pro Leu Pro Val Ala Gly Ala
                165                 170                 175

Phe Asn Ala Tyr Gly Leu Gly His Asp Ala Thr Val Pro Trp Phe
            180                 185                 190

<210> SEQ ID NO 59
<211> LENGTH: 28
<212> TYPE: RNA
<213> ORGANISM: Artificial Sequence
<220> FEATURE:
<223> OTHER INFORMATION: Synthetic oligonucleotide

<400> SEQUENCE: 59
guucacugcc gcauaggcag cucagaaa                                  28

<210> SEQ ID NO 60
<211> LENGTH: 182
<212> TYPE: PRT
<213> ORGANISM: Desulfurispirillum indicum

<400> SEQUENCE: 60

Met Asp Ser Tyr Ile Glu Ile Arg Ile Leu Pro Asp Gln Glu Phe Glu
1               5                   10                  15

Ala Thr Thr Leu Met Ser Thr Val Phe Ala Lys Leu His Arg Ala Leu
```

```
                   20                  25                  30
Val Glu Ser Gly Arg Ser Asp Ile Gly Val Ser Phe Pro Glu Ala Gly
            35                  40                  45

Lys Thr Pro Gly Ala Leu Leu Arg Leu His Gly Ser Leu Ala Ala Leu
 50                  55                  60

Glu Ser Ile Met Thr Leu Ser Trp Leu Thr Gly Leu Gln Asp Tyr Thr
 65                  70                  75                  80

Gln Thr Ser Gly Ile Leu Gln Val Pro Ala Gln Ala Ala Tyr Val Gln
                85                  90                  95

Val Ala Arg Val Gln Ser Lys Met Thr Ala Ser Arg Ile Arg Arg Ala
            100                 105                 110

Leu Lys Arg Gly Ser Leu Ser Glu Glu Arg Ala Leu Glu Leu Leu Gln
        115                 120                 125

Ser Arg Asp Gln Leu Asn Gln Pro Phe Phe Arg Leu Leu Ser Ala Ser
    130                 135                 140

Thr Ala Gln Lys Phe Pro Leu Phe Ile Glu Gln Arg Asn Ala Glu Lys
145                 150                 155                 160

Ala Gly Lys Gln Ser Val Tyr Ser Ala Tyr Gly Leu Ser Val Gly Gly
                165                 170                 175

Ser Thr Val Pro Trp Phe
            180

<210> SEQ ID NO 61
<211> LENGTH: 184
<212> TYPE: PRT
<213> ORGANISM: Photobacterium profundum

<400> SEQUENCE: 61

Met Met Asp Ser Tyr Val Asp Ile Gln Leu Lys Pro Asp Ala Glu Met
 1               5                  10                  15

Arg Glu Ala Glu Leu Ser Ser Lys Val Phe Thr Lys Phe His Lys Ala
            20                  25                  30

Leu Ala Thr Leu Asn Thr Asn Lys Ile Gly Ile Ser Phe Pro Gln Met
        35                  40                  45

Asn Leu Lys Leu Gly Arg Leu Phe Arg Ile His Gly Asn Ala Ser Leu
    50                  55                  60

Leu Lys Asp Leu Gln Gly Ile Lys Trp Leu Gly Ala Leu Ala Gly Tyr
 65                  70                  75                  80

Cys Gln Val Gly Glu Ile Thr Val Val Pro Asp Gln Val Gln Tyr Arg
                85                  90                  95

Val Ile Ser Val Lys Arg Ser Asn Leu Ser Lys Ala Lys Leu Lys Arg
            100                 105                 110

Leu Ile Ala Arg Gly Ser Ile Asp Lys Asp Gly Glu Lys Arg Tyr Lys
        115                 120                 125

Val Lys Met Leu Ser Gln Gly Phe Asp Asn Pro Tyr Leu Asp Leu Phe
    130                 135                 140

Ser Ser Ser Thr Gly Gln Val Tyr Arg Lys Phe Glu Phe Gly Asp
145                 150                 155                 160

Ile Gln Ala Thr Ser Val Ser Asp Glu Phe Asp Ser Tyr Gly Leu Ser
                165                 170                 175

Asn Thr Ala Thr Ile Pro Trp Phe
            180

<210> SEQ ID NO 62
<211> LENGTH: 184
```

```
<212> TYPE: PRT
<213> ORGANISM: Legionella pneumophila

<400> SEQUENCE: 62

Met Asp His Tyr Leu Asp Ile Ser Ile Leu Pro Asp Ser Glu Ph

```
Phe Asn Glu Pro Ser Pro Gly Leu Phe Asp Gln Phe Gly Leu Ser Asn
                165                 170                 175

Ser Ala Thr Val Pro Trp Phe Asp
            180

<210> SEQ ID NO 64
<211> LENGTH: 183
<212> TYPE: PRT
<213> ORGANISM: Shewanella putrefaciens

<400> SEQUENCE: 64

Met Asn Ser Tyr Ile Asp Ile Arg Leu Lys Pro Asp Ala Glu Met Arg
1               5                   10                  15

Glu Ala Glu Leu Ser Ser Lys Val Phe Thr Lys Phe His Lys Ala Leu
            20                  25                  30

Val Thr Leu Asn Ser His Lys Ile Gly Ile Ser Phe Pro Gln Met Lys
        35                  40                  45

Leu Ser Leu Gly Gln Leu Phe Arg Ile His Gly Asp Ala Ser Leu Leu
    50                  55                  60

His Asp Leu Gln Gly Leu Asp Trp Leu Gly Pro Leu Ala Gly Tyr Cys
65                  70                  75                  80

Gln Val Thr Ala Val Ser Ala Val Pro Asp His Val Gln Tyr Arg Ile
                85                  90                  95

Val Ser Val Lys Arg Ser Asn Leu Ser Lys Ala Lys Leu Lys Arg Leu
            100                 105                 110

Ile Ala Arg Gly Ser Ile Asp Lys Asp Gly Glu Lys Arg Tyr Lys Val
        115                 120                 125

Lys Met Leu Gly Gln Gly Phe Asp Asn Pro Tyr Leu Asp Leu Phe Ser
    130                 135                 140

Ser Ser Thr Gly Gln Val Tyr Arg Lys Phe Phe Glu Phe Ser Asp Ile
145                 150                 155                 160

Gln Ala His Pro Leu Asp Gly Glu Phe Asp Ser Tyr Gly Leu Ser Lys
                165                 170                 175

Thr Ala Thr Val Pro Trp Phe
            180

<210> SEQ ID NO 65
<211> LENGTH: 28
<212> TYPE: RNA
<213> ORGANISM: Artificial Sequence
<220> FEATURE:
<223> OTHER INFORMATION: Synthetic oligonucleotide

<400> SEQUENCE: 65
guucaccgcc gcacaggcgg cuuagaaa                                        28

<210> SEQ ID NO 66
<211> LENGTH: 184
<212> TYPE: PRT
<213> ORGANISM: Legionella pneumophila

<400> SEQUENCE: 66

Met Asp Tyr Tyr Val Asp Ile Leu Ile Lys Pro Asp Ser Glu Lys Ser
1               5                   10                  15

Leu Asn Phe Leu Leu Ser Thr Leu Tyr Thr Lys Leu His Lys Val Leu
            20                  25                  30

His Asp Met Ala Ser Thr Asn Ile Gly Val Ser Phe Pro Lys Tyr Asn
        35                  40                  45

```
Ile Thr Leu Gly Asn Ile Leu Arg Ile His Ser Lys Lys Val Val Leu
     50                  55                  60

Asp Glu Leu Leu Gly Met Asn Phe Leu Ser Gly Ile Asn Asn Tyr Tyr
 65                  70                  75                  80

Glu Val Ser Pro Ile Lys Ser Val Pro Ala Asp Ser Lys Phe Arg Ile
                 85                  90                  95

Ile Ser Arg Lys Gln Thr Thr Met Ser Gln Ser Lys Met Arg Arg Leu
             100                 105                 110

Phe Lys Arg Gly Ser Met Thr Val Gly Asp Ile Arg Gln Tyr Lys Ala
         115                 120                 125

Lys Met Phe Ala Lys Ser Ile Asp Asn Pro Tyr Leu Glu Leu Val Ser
130                 135                 140

Gly Ser Asn Gly Tyr Arg Tyr Arg Arg Tyr Ile Glu Phe Gly Glu Leu
145                 150                 155                 160

Leu Asp Gln Pro Val Tyr Gly Glu Phe Asp Arg Phe Gly Leu Ser Lys
                 165                 170                 175

Thr Ala Thr Val Pro Trp Phe Asp
             180
```

<210> SEQ ID NO 67
<211> LENGTH: 28
<212> TYPE: RNA
<213> ORGANISM: Artificial Sequence
<220> FEATURE:
<223> OTHER INFORMATION: Synthetic oligonucleotide

<400> SEQUENCE: 67
guuaacugcc gcacaggcag cuuagaag                                       28

<210> SEQ ID NO 68
<211> LENGTH: 183
<212> TYPE: PRT
<213> ORGANISM: Vibrio metschnikovii

<400> SEQUENCE: 68

```
Met Asp Ser Tyr Ile Glu Ile Arg Leu Gln Pro Asp Ala Glu Met Pro
 1               5                  10                  15

Glu Ala Glu Leu Ser Ser Lys Val Phe Thr Lys Phe His Lys Ala Leu
             20                  25                  30

Val Ile Leu His Ser Asn Gln Ile Gly Ile Ser Phe Pro Glu Val Asn
         35                  40                  45

Val Lys Leu Gly Arg Leu Phe Arg Leu His Gly Glu Ala Ser Phe Leu
     50                  55                  60

His Asp Leu Gln Gly Leu Asn Trp Leu Gly Pro Leu Ser Gly Tyr Cys
 65                  70                  75                  80

Gln Val Ser Glu Ile Leu Ala Ile Pro Glu Gln Val Gln Tyr Arg Val
                 85                  90                  95

Ile Ser Val Lys Arg Ser Asn Leu Ser Gln Ala Lys Leu Arg Arg Leu
             100                 105                 110

Ile Ala Arg Gly Ser Ile Asp Lys Glu Gly Glu Lys Arg Tyr Lys Val
         115                 120                 125

Lys Met Leu Ser Gln Gly Phe Asp Asn Pro Tyr Leu Asp Leu Phe Ser
130                 135                 140

Ser Ser Thr Lys Gln Val His Arg Lys Phe Phe Glu Phe Gly Glu Ile
145                 150                 155                 160

Gln Pro Leu Pro Val Ser Gly Lys Phe Asp Ser Tyr Gly Leu Ser His
                 165                 170                 175
```

-continued

```
Thr Thr Thr Val Pro Trp Phe
            180

<210> SEQ ID NO 69
<211> LENGTH: 28
<212> TYPE: RNA
<213> ORGANISM: Artificial Sequence
<220> FEATURE:
<223> OTHER INFORMATION: Synthetic oligonucleotide

<400> SEQUENCE: 69
guucacugcc gcauaggcag cuuagaaa                                              28

<210> SEQ ID NO 70
<211> LENGTH: 102
<212> TYPE: PRT
<213> ORGANISM: Citrobacter koseri

<400> SEQUENCE: 70

Met Ala Ile Thr Pro Val Pro Ala Val Lys Gly Trp Arg Thr Val Ser
1               5                   10                  15

Arg Val Gln Val Lys Ser Ser Pro Gln Arg Leu Leu Arg Arg Ser Val
            20                  25                  30

Arg Lys Gly Trp Leu Thr Glu Glu Gln Ala Gln Leu Arg Leu Val Glu
        35                  40                  45

Ser Thr Glu Gln His Ser Asp Leu Pro Tyr Leu Asn Val Lys Ser Leu
    50                  55                  60

Ser Asn Gln Gln Gln Phe Arg Val Phe Ile Arg His Ser Glu Leu Arg
65                  70                  75                  80

Ser Glu Pro Val Ser Gly Thr Phe Thr Ser Tyr Gly Leu Ser Ser Thr
                85                  90                  95

Ala Thr Ile Pro Trp Phe
            100

<210> SEQ ID NO 71
<211> LENGTH: 183
<212> TYPE: PRT
<213> ORGANISM: Vibrio sp. RC586

<400> SEQUENCE: 71

Met Asp Ala Tyr Ile Asp Ile Arg Leu Met Pro Asp Ala Glu Met Arg
1               5                   10                  15

Glu Ala Glu Leu Ser Ser Lys Val Phe Ile Lys Phe His Lys Ala Leu
            20                  25                  30

Val Lys Leu Arg Ser Asn Lys Ile Gly Ile Ser Phe Pro Glu Ala Asn
        35                  40                  45

Ile Lys Leu Gly Arg Leu Phe Arg Leu His Gly Glu Met Ser Ala Leu
    50                  55                  60

His Asp Leu Gln Gly Leu Asn Trp Leu Gly Pro Leu Ala Gly Tyr Cys
65                  70                  75                  80

Lys Ile Thr Thr Val Thr His Val Pro Asp Gln Val Gln Tyr Arg Ile
                85                  90                  95

Ile Ser Val Lys Arg Ser Asn Leu Ser Lys Ala Lys Leu Thr Arg Leu
            100                 105                 110

Ile Ala Arg Gly Ser Ile Asp Lys Asp Gly Glu Lys Arg Tyr Lys Val
        115                 120                 125

Lys Met Leu Ser Gln Gly Phe Asp Asn Pro Tyr Leu Asp Leu Ser Ser
    130                 135                 140
```

```
Ser Ser Thr Gly Gln Val Tyr Arg Lys Phe Phe Glu Phe Ser Asp Ile
145                 150                 155                 160

Gln Ala Asp Pro Val Asp Gly Glu Phe Asp Ser Tyr Gly Leu Ser Lys
                165                 170                 175

Thr Ala Thr Val Pro Trp Phe
            180

<210> SEQ ID NO 72
<211> LENGTH: 28
<212> TYPE: RNA
<213> ORGANISM: Artificial Sequence
<220> FEATURE:
<223> OTHER INFORMATION: Synthetic oligonucleotide

<400> SEQUENCE: 72
aguguucugc cgaauaggca gcuaagaa                                            28

<210> SEQ ID NO 73
<211> LENGTH: 184
<212> TYPE: PRT
<213> ORGANISM: Vibrio cholerae

<400> SEQUENCE: 73

Met Met Asp Ala Tyr Ile Asp Ile Arg Leu Met Pro Asp Ala Glu Met
1               5                   10                  15

Arg Glu Ala Glu Leu Ser Ser Lys Val Phe Ile Lys Phe His Lys Ala
                20                  25                  30

Leu Val Lys Leu Gln Ser Asn Lys Ile Gly Ile Ser Phe Pro Glu Ala
            35                  40                  45

Asn Ile Lys Leu Gly Arg Leu Phe Arg Leu His Gly Glu Val Ser Ala
        50                  55                  60

Leu His Asp Leu Gln Gly Leu Asn Trp Leu Gly Pro Leu Ala Gly Tyr
65                  70                  75                  80

Cys Lys Ile Thr Thr Val Thr His Val Pro Asp Gln Val Glu Tyr Arg
                85                  90                  95

Ile Ile Ser Val Lys Arg Ser Asn Leu Ser Lys Ala Lys Leu Ala Arg
                100                 105                 110

Leu Ile Ala Arg Gly Ser Ile Asp Lys Asp Gly Glu Lys Arg Tyr Lys
            115                 120                 125

Val Lys Met Leu Arg Gln Gly Phe Asp Asn Pro Tyr Leu Asp Leu Ser
        130                 135                 140

Ser Ser Ser Thr Gly Gln Val Tyr Arg Lys Phe Phe Glu Phe Ser Asp
145                 150                 155                 160

Ile Gln Ala Glu Pro Val Asp Gly Glu Phe Asp Ser Tyr Gly Leu Ser
                165                 170                 175

Lys Thr Ala Thr Val Pro Trp Phe
            180

<210> SEQ ID NO 74
<211> LENGTH: 29
<212> TYPE: RNA
<213> ORGANISM: Artificial Sequence
<220> FEATURE:
<223> OTHER INFORMATION: Synthetic oligonucleotide

<400> SEQUENCE: 74
guucacugcc gcacaggcag cuuagaaau                                           29
```

```
<210> SEQ ID NO 75
<211> LENGTH: 197
<212> TYPE: PRT
<213> ORGANISM: Oxalobacter formigenes

<400> SEQUENCE: 75
```

Met Lys His Tyr Ile Glu Ile Thr Leu Thr Gly Ser Pro Asp Phe Pro
1               5                   10                  15

Leu Tyr His Leu Trp Ser Lys Leu Tyr Thr Gln Leu His Leu Ala Leu
            20                  25                  30

Val Glu Asn Arg Asp Ala Ser Asp Gln Val Asn Ile Gly Val Ser Phe
        35                  40                  45

Pro Glu Tyr Tyr Phe Asn Glu Glu Lys Gly Met Gly Phe Leu Gly Thr
    50                  55                  60

Lys Leu Arg Leu Phe Ala Glu Asp Glu Thr Ser Leu Gln Lys Ile Asp
65                  70                  75                  80

Ile Gln Lys Trp Phe Val Arg Leu Asn Asp Cys Ile His Ile Thr Pro
                85                  90                  95

Val Cys Arg Val Pro Leu Asn Glu Ile Thr Gly Tyr Ala Thr Phe Ser
            100                 105                 110

Arg Lys His Ile Lys Ser Asn Ala Glu Arg Leu Ala Arg Arg Gln Met
        115                 120                 125

Lys Arg His Lys Asp Leu Ser Phe His Glu Thr Val Gln Arg Tyr Gln
    130                 135                 140

Lys Asn Leu Ala Lys Ser Pro Leu Pro Phe Ile Gln Leu Glu Ser Leu
145                 150                 155                 160

Thr Asn Ser His Pro Phe Lys Leu Phe Ile Glu Lys Lys Pro Ala Ile
                165                 170                 175

Asn Ala Ser Leu Lys Val Phe Thr Thr Tyr Gly Leu Ser Ala Glu Ser
            180                 185                 190

Thr Ile Pro Glu Phe
        195

```
<210> SEQ ID NO 76
<211> LENGTH: 28
<212> TYPE: RNA
<213> ORGANISM: Artificial Sequence
<220> FEATURE:
<223> OTHER INFORMATION: Synthetic oligonucleotide

<400> SEQUENCE: 76
guucacugcc guauaggcag cuuagaag                                               28

<210> SEQ ID NO 77
<211> LENGTH: 193
<212> TYPE: PRT
<213> ORGANISM: Psychromonas ingrahamii

<400> SEQUENCE: 77
```

Met Lys Tyr Tyr Leu Asp Ile Thr Leu Leu Pro Asp Ile Glu Ile Pro
1               5                   10                  15

Leu Gly Phe Ile Trp Gln Lys Val Phe Gln Gln Val His Ile Ala Leu
            20                  25                  30

Ala Asp Asn Lys Val Gly Glu Asn Glu Ser Asp Ile Ala Leu Ser Leu
        35                  40                  45

Pro Asn Tyr Gly Asp Lys Ala Phe Pro Leu Gly Asn Lys Leu Arg Leu
    50                  55                  60

Phe Ser Val Ser Glu Gln Ala Leu Glu Arg Leu Ala Ile Thr Lys Trp

```
                65                  70                  75                  80
Leu Lys Arg Phe Thr Asp His Thr His Ile Thr Ser Val Lys Ala Val
                    85                  90                  95

Pro Glu Ser Ala Asn Glu Tyr Ala Cys Phe Thr Arg Lys Gln Phe Asn
                100                 105                 110

Thr Asn Ile Ser Arg Leu Ala Arg Arg Ala Lys Arg His Met Glu
            115                 120                 125

Thr Phe Glu Lys Ala Leu Gln Tyr Tyr Asp Asn Phe Ala Glu Glu Gln
        130                 135                 140

Thr Lys Leu Pro Phe Met Asn Ile Lys Ser Leu Thr Asn Asn Ala Gln
145                 150                 155                 160

Phe Arg Ile Phe Ile Glu Arg Ser Ile Thr Lys Ile Pro Lys Gln Gly
                165                 170                 175

Thr Phe Asn Cys Tyr Gly Leu Ser Gln Ala Ile Ala Thr Val Pro Trp
                180                 185                 190

Phe

<210> SEQ ID NO 78
<211> LENGTH: 29
<212> TYPE: RNA
<213> ORGANISM: Artificial Sequence
<220> FEATURE:
<223> OTHER INFORMATION: Synthetic oligonucleotide

<400> SEQUENCE: 78
guguuccccg ugcccacggg gaugaaccg                                           29

<210> SEQ ID NO 79
<211> LENGTH: 202
<212> TYPE: PRT
<213> ORGANISM: Dichelobacter nodosus

<400> SEQUENCE: 79

Met Asn Phe Tyr Gln Glu Ile Thr Leu Leu Pro Asp Ala Glu Val Ser
1               5                   10                  15

Leu Tyr Phe Leu Trp Ser Lys Val Tyr Gly Gln Leu His Ile Ala Leu
            20                  25                  30

Ala Asp Val Arg Asn Arg Tyr Gly Ile Asp Thr Ile Gly Val Asn Phe
        35                  40                  45

Pro His Tyr Val Tyr Glu Glu Gln Asn His Lys Val Val Ala Ala Arg
    50                  55                  60

Leu Gly Asp Gln Leu Arg Ile Phe Ala Leu Ala Glu Asn Asp Leu Glu
65                  70                  75                  80

Lys Leu Gln Ile Asn Gln Trp Leu Glu Arg Leu Ser Asp Tyr Val His
                85                  90                  95

Ile Lys Arg Ile Ser Lys Ile Glu Pro Asn Lys Val Thr Gly Tyr Val
            100                 105                 110

Val Val Lys Arg Tyr Arg Tyr Pro Ser Leu Asp Lys Val Ala Leu Arg
        115                 120                 125

Phe Ala Gln Phe Arg Lys Ile Asn Phe Glu Glu Ala Arg Lys His Cys
    130                 135                 140

Thr Lys Tyr Lys His Gln Ala Lys Asn Tyr Pro Phe Ile Met Leu Lys
145                 150                 155                 160

Ser Gln Ser Asn Gln Glu Tyr Tyr Lys Leu Ser Ile Arg Gln Glu Asn
                165                 170                 175

Ala Gln Glu Ser Val Ser Gly Arg Phe Asn Val Tyr Gly Ile Asn Ser
```

```
                   180                 185                 190

Ala Thr Gly Ile Val Thr Val Pro Asn Trp
            195                 200

<210> SEQ ID NO 80
<211> LENGTH: 194
<212> TYPE: PRT
<213> ORGANISM: Shewanella baltica

<400> SEQUENCE: 80

Met Asn His Tyr Leu Asp Ile Thr Leu Leu Pro Asn Glu Glu Val Gly
1               5                   10                  15

His Tyr Phe Leu Trp Glu Lys Leu Tyr His Gln Val His Leu Ala Leu
            20                  25                  30

Val Glu His Lys Asn Arg Val Gly Gln Phe Glu Ile Ala Ala Ala Phe
        35                  40                  45

Pro Gln Phe Asn Glu Met Asp Asn Ser Leu Gly Ser Lys Leu Arg Leu
    50                  55                  60

Leu Ala Thr Gln Pro Gln His Leu Glu Asp Leu Lys Val Ser Asn Trp
65                  70                  75                  80

Leu Arg His Phe Thr Asp Tyr Leu His Ile Ser Ser Ile Arg Pro Val
                85                  90                  95

Pro Glu Lys Ile Glu Val Tyr Val Ala Tyr Ser Arg Pro Ala Ile Arg
            100                 105                 110

Ala Asn Lys Ala Arg Glu Ile Ala Arg Arg Met Lys Arg His Asn Glu
        115                 120                 125

Thr Leu Glu Gln Ala Thr Ala His Phe Glu Gly Phe Lys Pro Lys Lys
    130                 135                 140

Thr Lys Ala Pro Phe Val Tyr Met Gln Ser Tyr Thr Lys Asp Ser Arg
145                 150                 155                 160

Phe Pro Leu Phe Ile Gln Gln Thr His Ser Ala Val Val Lys Glu Gly
                165                 170                 175

Ser Val Ser Phe Asp Ser Tyr Gly Leu Ser Ser Arg Gly Tyr Leu Pro
            180                 185                 190

Lys Phe

<210> SEQ ID NO 81
<211> LENGTH: 194
<212> TYPE: PRT
<213> ORGANISM: Shewanella baltica

<400> SEQUENCE: 81

Met Asn His Tyr Leu Asp Ile Thr Leu Leu Pro Asn Glu Glu Val Gly
1               5                   10                  15

His Tyr Phe Leu Trp Glu Lys Leu Tyr His Gln Met His Leu Ala Leu
            20                  25                  30

Val Glu His Lys Asn Arg Val Gly Gln Phe Glu Ile Ala Ala Ala Phe
        35                  40                  45

Pro Gln Phe Asn Glu Met Asp Asn Leu Gly Ser Lys Leu Arg Leu
    50                  55                  60

Leu Ala Thr Gln Pro Gln His Leu Glu Asp Leu Lys Val Ser Asn Trp
65                  70                  75                  80

Leu Arg His Phe Thr Asp Tyr Leu His Ile Ser Ser Ile Arg Pro Val
                85                  90                  95

Pro Asp Lys Ile Glu Val Tyr Val Ala Tyr Ser Arg Pro Ala Ile Arg
            100                 105                 110
```

```
Ala Asn Lys Ala Arg Glu Ile Ala Arg Arg Met Lys Arg His Asn Glu
        115                 120                 125

Thr Leu Val Gln Ala Thr Ala His Phe Glu Gly Phe Lys Pro Lys Lys
    130                 135                 140

Thr Lys Ala Pro Phe Val Tyr Met Gln Ser Tyr Thr Lys Asp Ser Arg
145                 150                 155                 160

Phe Pro Leu Phe Ile Gln Gln Thr His Ser Ala Val Val Lys Glu Gly
                165                 170                 175

Asn Val Ser Phe Asp Ser Tyr Gly Leu Ser Ser Arg Gly Tyr Leu Pro
                180                 185                 190

Lys Phe

<210> SEQ ID NO 82
<211> LENGTH: 204
<212> TYPE: PRT
<213> ORGANISM: Acinetobacter baumannii

<400> SEQUENCE: 82

Met Met Asn Trp Tyr Gln Glu Ile Thr Leu Ile Asp Gln Asp Glu Ile
1               5                   10                  15

Ser Leu Tyr Phe Ile Trp Ser Lys Val Tyr Thr Gln Leu His Ile Ala
                20                  25                  30

Phe Ala Glu His Ser Asn Glu Gln Gly Arg Ile Ser Phe Gly Val Ser
            35                  40                  45

Phe Pro Gln Tyr Arg Ile Asn Glu Gln Lys Lys Ile Gly Phe Leu Gly
        50                  55                  60

Thr Lys Ile Arg Val Phe Ala Ser Ser Glu Asn Asp Leu Gln Gln Leu
65                  70                  75                  80

Asn Leu Gly Lys Trp Leu Glu Arg Phe Ile Asp Tyr Val His Ile Thr
                85                  90                  95

Gln Pro Arg Glu Val Pro Arg Ala Lys Ile Thr Gly Tyr Ala His Tyr
            100                 105                 110

Tyr Arg Val Asn His Arg Met Ser Val Glu Glu Arg Ile Val His Gln
        115                 120                 125

Ala Gln Arg Arg Asn Ile Ser Leu Asp Gln Ala Arg Gln His Phe Lys
    130                 135                 140

Gln Tyr Val Glu Gln Pro Val Val Glu Pro Tyr Val Ser Leu Lys Ser
145                 150                 155                 160

Leu Ser Ala Lys Arg Glu Glu Asn Val Asp Arg Pro Tyr Arg Leu Tyr
                165                 170                 175

Ile Gly Lys Ser Leu Val Asp Glu Ala Arg Asp Gly Met Phe Gly Thr
                180                 185                 190

Tyr Gly Leu Ser Arg Met Thr Thr Val Pro Glu Phe
        195                 200

<210> SEQ ID NO 83
<211> LENGTH: 28
<212> TYPE: RNA
<213> ORGANISM: Artificial Sequence
<220> FEATURE:
<223> OTHER INFORMATION: Synthetic oligonucleotide

<400> SEQUENCE: 83
guucauggcg gcauacgcca uuuagaaa                                          28

<210> SEQ ID NO 84
```

```
<211> LENGTH: 203
<212> TYPE: PRT
<213> ORGANISM: Acinetobacter baumannii

<400> SEQUENCE: 84
```

Met Asn Trp Tyr Gln Glu Ile Thr Leu Ile Asp Gln Asp Glu Ile Ser
1               5                   10                  15

Leu Tyr Phe Ile Trp Ser Lys Val Tyr Thr Gln Leu His Ile Ala Phe
            20                  25                  30

Ala Glu His Ser Asn Glu Gln Gly Arg Ile Ser Phe Gly Val Ser Phe
        35                  40                  45

Pro Gln Tyr Arg Ile Asn Glu Gln Lys Lys Ile Gly Phe Leu Gly Thr
    50                  55                  60

Lys Ile Arg Val Phe Ala Ser Ser Glu Asn Asp Leu Gln Gln Leu Asn
65                  70                  75                  80

Leu Gly Lys Trp Leu Glu Arg Phe Ile Asp Tyr Val His Ile Thr Gln
                85                  90                  95

Pro Arg Glu Val Pro Arg Ala Lys Ile Thr Gly Tyr Ala His Tyr Tyr
            100                 105                 110

Arg Val Asn His Arg Met Ser Val Glu Glu Arg Ile Val His Gln Ala
        115                 120                 125

Gln Arg Arg Asn Ile Ser Leu Asp Gln Ala Arg Gln His Phe Lys Gln
    130                 135                 140

Tyr Val Glu Gln Pro Val Val Glu Pro Tyr Val Ser Leu Lys Ser Leu
145                 150                 155                 160

Ser Ala Lys Arg Glu Glu Asn Val Asp Arg Pro Tyr Arg Leu Tyr Ile
                165                 170                 175

Gly Lys Ser Leu Val Asp Glu Ala Arg Asp Gly Met Phe Gly Thr Tyr
            180                 185                 190

Gly Leu Ser Arg Met Thr Thr Val Pro Glu Phe
        195                 200

```
<210> SEQ ID NO 85
<211> LENGTH: 186
<212> TYPE: PRT
<213> ORGANISM: Pasteurella multocida

<400> SEQUENCE: 85
```

Met Thr Thr His Tyr Ile Glu Leu Lys Ala Ile Pro Gln Met Asp Met
1               5                   10                  15

Leu Gln Ser Glu Val Ile Gly His Cys Met Gln Ile Leu His Gln Phe
            20                  25                  30

Leu Pro His Phe Glu Gly Arg Val Gly Val Ala Phe Pro Ala Tyr Gly
        35                  40                  45

Leu Gly Arg Thr Leu Gly Gly Ile Val Arg Leu Phe Ala Asn Gln Glu
    50                  55                  60

Asp Cys Asn Gln Leu His Gln Gln Leu Leu Arg Ser Gly Leu Ser Asp
65                  70                  75                  80

Tyr Ala Leu Ile Ser Glu Val Ser Lys Thr Pro Leu Pro Thr Glu His
                85                  90                  95

Arg Ser Tyr Ser Arg Val His Arg Lys Gly Gln Ser Ala Ile Arg Arg
            100                 105                 110

Thr Glu Lys Arg Leu Lys Ser Gln Gly Arg Trp Asp Glu Ser Ile Arg
        115                 120                 125

Ala Asp Met Gln Gln Arg Gln Gln Asn Val Ala Phe Phe Pro His Cys
    130                 135                 140

His Leu Lys Ser Ala Ser Thr Gly Gln Arg Phe Ile Leu Ala Val Lys
145                 150                 155                 160

Glu Asn Arg Met Pro Gln Ser Cys Val Gly Val Phe Asn Ala Tyr Gly
                165                 170                 175

Leu Ser Asn Ser Ala Thr Val Pro His Phe
            180                 185

<210> SEQ ID NO 86
<211> LENGTH: 28
<212> TYPE: RNA
<213> ORGANISM: Artificial Sequence
<220> FEATURE:
<223> OTHER INFORMATION: Synthetic oligonucleotide

<400> SEQUENCE: 86
guucaccauc guguagaugg cuuagaaa                                              28

<210> SEQ ID NO 87
<211> LENGTH: 28
<212> TYPE: RNA
<213> ORGANISM: Artificial Sequence
<220> FEATURE:
<223> OTHER INFORMATION: Synthetic oligonucleotide

<400> SEQUENCE: 87
guuaacugcc guauaggcag cuuagaaa                                              28

<210> SEQ ID NO 88
<211> LENGTH: 187
<212> TYPE: PRT
<213> ORGANISM: Aggregatibacter actinomycetemcomitans

<400> SEQUENCE: 88

Met Thr Val Gln Thr His Tyr Ile Glu Ile Lys Ala Ile Pro Gln Val
1               5                   10                  15

Asp Met Leu Gln Thr Glu Val Ile Gly Phe Cys Leu Gln Lys Leu His
            20                  25                  30

Gln Ile Leu Pro His Phe Glu Gly Arg Ile Gly Leu Ala Phe Pro Ala
        35                  40                  45

Tyr Gly Asn Asp Lys Thr Leu Gly Gly Ile Ile Arg Leu Phe Gly Thr
    50                  55                  60

Glu Asn Asp Cys Gly Phe Ile His Phe Lys Leu Gln Ser Leu Arg Asp
65                  70                  75                  80

Tyr Ala Leu Ile Ser Glu Val Met Pro Ile Pro Glu Lys Val Arg Ser
                85                  90                  95

Tyr Arg Ile Tyr Gln Arg Ile Gln Pro Lys Gly Gln Ser Ser Ile Arg
            100                 105                 110

Arg Ala Glu Lys Arg Leu Thr Ala Gln Gly Lys Trp Asn Glu Glu Val
        115                 120                 125

Leu Gln Asn Met Leu Gln Lys Gln Ala Thr Gln Arg Ile Tyr Pro His
    130                 135                 140

Ala His Leu Lys Ser Ser Ser Thr Lys Gln Gln Phe Ile Leu Ala Ile
145                 150                 155                 160

Lys Ser Val His Gln Thr Lys Ala Val Glu Gly Val Phe Ser Ala Tyr
                165                 170                 175

Gly Leu Ser Gln Thr Thr Thr Val Pro His Phe
            180                 185

<210> SEQ ID NO 89
<211> LENGTH: 28
<212> TYPE: RNA
<213> ORGANISM: Artificial Sequence
<220> FEATURE:
<223> OTHER INFORMATION: Synthetic oligonucleotide

<400> SEQUENCE: 89
cuucacugcc gaauaggcag cuuagaaa					28

<210> SEQ ID NO 90
<211> LENGTH: 199
<212> TYPE: PRT
<213> ORGANISM: Marinomonas sp. MWYL1

<400> SEQUENCE: 90

Met Lys His Tyr Ile Asp Ile Thr Leu Leu Pro Ser Asp Ile Gly
1               5                   10                  15

Val His Phe Leu Trp Ser Lys Leu Met Met Gln Val His Leu Ala Leu
                20                  25                  30

Val Glu Ile Gln Asn Glu Gln Lys Gln Val Pro Val Ala Val Ser Phe
            35                  40                  45

Pro Lys Tyr Gln Pro Arg Glu Asn Glu Lys Leu Gly Phe Val Gly Asn
    50                  55                  60

Lys Leu Arg Leu Phe Ala Asn Asp Lys Thr Asp Leu Glu Arg Leu Asn
65                  70                  75                  80

Phe Gly Lys Trp Leu His Arg Leu Glu Asp Tyr Val His Ile Lys Ser
                85                  90                  95

Ile Ala Asp Val Pro Asn Asp Val Ile Ser Tyr Glu Ser Phe Asn Arg
            100                 105                 110

Arg Ser Lys Ser Gly Ser Pro Asp Lys His Ile Lys Arg Met Gln
    115                 120                 125

Arg His Asn Glu Thr Trp Glu Gln Ala Ala Ala Phe Phe Lys Gly Tyr
130                 135                 140

Ser Met Glu Lys Ala Asp Lys Asp Leu Pro Phe Ile Arg Met Lys Ser
145                 150                 155                 160

Leu His Ser Asp Asn Glu Phe Cys Met Ser Ile Ile Arg Lys Glu Ala
                165                 170                 175

Ala Pro Ser Asn Lys His Ile Met Phe Asn Thr Tyr Gly Leu Ser Ala
            180                 185                 190

Glu Gly Val Leu Pro Lys Phe
        195

<210> SEQ ID NO 91
<211> LENGTH: 28
<212> TYPE: RNA
<213> ORGANISM: Artificial Sequence
<220> FEATURE:
<223> OTHER INFORMATION: Synthetic oligonucleotide

<400> SEQUENCE: 91
guucgccgcc gagcacgcgg cuuagaaa					28

<210> SEQ ID NO 92
<211> LENGTH: 190
<212> TYPE: PRT
<213> ORGANISM: Dialister invisus

<400> SEQUENCE: 92

Met Glu Tyr Tyr Gln Glu Ile Thr Leu Leu Pro Cys Ala Glu Val Ser

```
            1               5                  10                 15
Leu Ala Phe Leu Trp Thr Lys Val Phe Thr Gln Leu His Ile Ala Phe
                    20                  25                  30

Ala Asp Glu Lys Asn Lys Ser Gly His Asn Leu Tyr Ala Val Ser Phe
                    35                  40                  45

Pro Glu Tyr Arg Glu Thr Gly Leu Gly Glu Lys Ile Arg Val Phe Ala
                    50                  55                  60

Glu Ala Gln Glu Leu Glu Arg Leu Asn Leu Ser Lys Val Leu Gly Arg
 65                      70                  75                  80

Leu Leu Asp Tyr Val His Cys Thr Ser Ile Arg Lys Val Pro Glu Arg
                        85                  90                  95

Lys Leu Arg Gly Tyr Ala Val Tyr Ser Arg Tyr Gln Pro Glu Gly Ser
                    100                 105                 110

Ile Trp Val Lys Ala Arg Arg Tyr Ala Lys Arg His Pro Gly Val Thr
                    115                 120                 125

Ile Glu Glu Ala Ala Arg Leu Leu Gln Gly Lys Arg Lys Ser Val Arg
                    130                 135                 140

Leu Pro Tyr Ile Gln Met Lys Ser Leu Ser Arg Gly Gly Thr Phe Ser
145                     150                 155                 160

Leu Phe Ile Lys Lys Arg Val Glu Lys Glu Ser Ala Leu Thr Glu Cys
                    165                 170                 175

Gly Thr Tyr Gly Leu Ser Asn Asn Arg Thr Val Pro Glu Phe
                    180                 185                 190

<210> SEQ ID NO 93
<211> LENGTH: 28
<212> TYPE: RNA
<213> ORGANISM: Artificial Sequence
<220> FEATURE:
<223> OTHER INFORMATION: Synthetic oligonucleotide

<400> SEQUENCE: 93
guuaacugcc gcauagguag uuuagaaa                                          28

<210> SEQ ID NO 94
<211> LENGTH: 28
<212> TYPE: RNA
<213> ORGANISM: Artificial Sequence
<220> FEATURE:
<223> OTHER INFORMATION: Synthetic oligonucleotide

<400> SEQUENCE: 94
guuaucugcc guauaggcag cuuagaaa                                          28

<210> SEQ ID NO 95
<211> LENGTH: 189
<212> TYPE: PRT
<213> ORGANISM: Actinobacillus pleuropneumoniae

<400> SEQUENCE: 95

Met Ser Glu Leu Thr His Tyr Ile Glu Leu Lys Ala Ile Pro Gln Val
 1               5                  10                  15

Asp Ile Leu Gln Thr Asp Val Ile Ala His Gly Leu Gln Ile Leu His
                    20                  25                  30

Lys Phe Leu Pro Leu Tyr Gln Gly Glu Ile Gly Leu Ser Phe Pro Ala
                    35                  40                  45

Tyr Gly Leu Gly Arg Thr Leu Gly Gly Ile Ile Arg Val Phe Gly Asn
                 50                  55                  60
```

```
Glu Gln His Cys Thr Gln Ile Lys Thr Gln Leu Ile Gly Glu Gly Leu
65                  70                  75                  80

Gln Asp Tyr Val Leu Ile Thr Ser Val Thr Pro Val Pro Glu Glu Ile
                85                  90                  95

Val Glu Tyr His Arg Tyr Gln Arg Val His Arg Lys Gly Gln Ser Ala
            100                 105                 110

Ile Arg Arg Thr Glu Gln Phe Leu Val Gln Gln Gly Lys Trp Thr Glu
        115                 120                 125

Glu Ile Arg Gln Glu Met Leu Ile His Gln Gln Asn Gln Lys Val Phe
130                 135                 140

Pro Tyr Val Lys Leu Lys Ser Gly Ser Thr Lys Gln His Phe Val Leu
145                 150                 155                 160

Ala Ile Arg Gln Leu Arg Leu Ala Glu Pro Ala Ser Gly Leu Phe Asn
                165                 170                 175

Ala Tyr Gly Leu Ser Gln Ala Ala Thr Val Pro His Phe
            180                 185

<210> SEQ ID NO 96
<211> LENGTH: 28
<212> TYPE: RNA
<213> ORGANISM: Artificial Sequence
<220> FEATURE:
<223> OTHER INFORMATION: Synthetic oligonucleotide

<400> SEQUENCE: 96
cuucacugcc guauaggcag cuuagaaa                                              28

<210> SEQ ID NO 97
<211> LENGTH: 189
<212> TYPE: PRT
<213> ORGANISM: Actinobacillus pleuropneumoniae

<400> SEQUENCE: 97

Met Ser Glu Leu Thr His Tyr Ile Glu Leu Lys Ala Ile Pro Gln Val
1               5                   10                  15

Asp Ile Leu Gln Thr Asp Val Ile Ala His Gly Leu Gln Ile Leu His
                20                  25                  30

Lys Phe Leu Pro Leu Tyr Gln Gly Glu Ile Gly Leu Ser Phe Pro Ala
            35                  40                  45

Tyr Gly Leu Gly Arg Thr Leu Gly Gly Ile Ile Arg Val Phe Gly Asn
        50                  55                  60

Glu Gln His Cys Thr Gln Ile Lys Thr Gln Leu Ile Gly Glu Gly Leu
65                  70                  75                  80

Gln Asp Tyr Val Leu Ile Thr Ser Val Thr Pro Val Pro Glu Glu Ile
                85                  90                  95

Val Glu Tyr His Arg Tyr Gln Arg Val His Arg Lys Gly Gln Ser Ala
            100                 105                 110

Ile Arg Arg Thr Glu Gln Phe Leu Val Gln Gln Gly Lys Trp Thr Glu
        115                 120                 125

Glu Ile Arg Gln Glu Met Leu Ile His Gln Gln Asn Gln Lys Val Phe
130                 135                 140

Pro Tyr Val Lys Leu Lys Ser Gly Ser Thr Lys Gln His Phe Val Leu
145                 150                 155                 160

Ala Ile Arg Gln Leu Arg Leu Ala Glu Pro Val Ser Gly Leu Phe Asn
                165                 170                 175

Ala Tyr Gly Leu Ser Lys Ile Ala Thr Val Pro His Phe
            180                 185
```

<210> SEQ ID NO 98
<211> LENGTH: 189
<212> TYPE: PRT
<213> ORGANISM: Actinobacillus pleuropneumoniae

<400> SEQUENCE: 98

Met Ser Glu Leu Thr His Tyr Ile Glu Leu Lys Ala Ile Pro Gln Val
1               5                   10                  15

Asp Ile Leu Gln Thr Asp Val Ile Ala His Gly Leu Gln Ile Leu His
            20                  25                  30

Lys Phe Leu Pro Leu Tyr Gln Gly Glu Ile Gly Leu Ser Phe Pro Ala
        35                  40                  45

Tyr Gly Leu Gly Arg Thr Leu Gly Gly Ile Ile Arg Val Phe Gly Asn
    50                  55                  60

Glu Gln His Cys Thr Gln Ile Lys Thr Gln Leu Ile Gly Glu Gly Leu
65                  70                  75                  80

Gln Asp Tyr Val Leu Ile Thr Ser Val Thr Pro Val Pro Glu Glu Ile
                85                  90                  95

Val Glu Tyr His Arg Tyr Gln Arg Val His Arg Lys Gly Gln Ser Ala
            100                 105                 110

Ile Arg Arg Thr Glu Gln Phe Leu Val Gln Gln Gly Lys Trp Thr Glu
        115                 120                 125

Glu Ile Arg Gln Glu Met Leu Ile His Gln Gln Asn Gln Lys Val Phe
    130                 135                 140

Pro His Val Lys Leu Lys Ser Gly Ser Thr Lys Gln His Phe Val Leu
145                 150                 155                 160

Ala Ile Arg Gln Leu Arg Leu Ala Glu Pro Ser Phe Gly Leu Phe Asn
                165                 170                 175

Thr Tyr Gly Leu Ser Lys Ile Ala Thr Val Pro His Phe
            180                 185

<210> SEQ ID NO 99
<211> LENGTH: 189
<212> TYPE: PRT
<213> ORGANISM: Actinobacillus pleuropneumoniae

<400> SEQUENCE: 99

Met Ser Glu Leu Thr His Tyr Ile Glu Leu Lys Ala Ile Pro Gln Val
1               5                   10                  15

Asp Ile Leu Gln Thr Asp Val Ile Ala His Gly Leu Gln Ile Leu His
            20                  25                  30

Lys Phe Leu Pro Leu Tyr Gln Gly Glu Ile Gly Leu Ser Phe Pro Ala
        35                  40                  45

Tyr Gly Leu Gly Arg Thr Leu Gly Gly Ile Ile Arg Val Leu Gly Asn
    50                  55                  60

Glu Gln His Cys Thr Gln Ile Lys Thr Gln Leu Ile Gly Glu Gly Leu
65                  70                  75                  80

Gln Asp Tyr Val Leu Ile Thr Ser Val Thr Pro Val Pro Glu Glu Ile
                85                  90                  95

Val Glu Tyr His Arg Tyr Gln Arg Val His Arg Lys Gly Gln Ser Ala
            100                 105                 110

Ile Arg Arg Thr Glu Gln Phe Leu Val Gln Gln Gly Lys Trp Thr Glu
        115                 120                 125

Glu Ile Arg Gln Glu Met Leu Ile His Gln Gln Asn Gln Lys Val Phe
    130                 135                 140

Pro His Val Lys Leu Lys Ser Gly Ser Thr Lys Gln His Phe Val Leu
145                 150                 155                 160

Ala Ile Arg Gln Leu Arg Leu Ala Glu Pro Ser Phe Gly Leu Phe Asn
                165                 170                 175

Thr Tyr Gly Leu Ser Lys Ile Ala Thr Val Pro His Phe
            180                 185

<210> SEQ ID NO 100
<211> LENGTH: 201
<212> TYPE: PRT
<213> ORGANISM: Streptococcus thermophilus

<400> SEQUENCE: 100

Met Ser Lys Thr Met Ile Ile Gly Leu Thr Gly Gly Ile Ala Ser Gly
1               5                   10                  15

Lys Ser Thr Val Val Glu Ile Ile Lys Asp Ala Gly Tyr Lys Val Ile
                20                  25                  30

Asp Ala Asp Gln Leu Val His Asp Met Gln Val Lys Gly Gly Arg Leu
            35                  40                  45

Tyr Gln Ala Leu Leu Asp Trp Leu Gly Asp Gly Ile Leu Leu Pro Asn
50                  55                  60

Gly Glu Leu Asn Arg Pro Lys Leu Gly Gln Leu Ile Phe Ser Ser Glu
65                  70                  75                  80

Glu Met Arg Tyr Gln Ser Ala Glu Ile Gln Gly Lys Ile Ile Arg Glu
                85                  90                  95

Glu Leu Ala Ala Lys Arg Asp Cys Leu Ala Lys Glu Glu Asp Val Phe
            100                 105                 110

Phe Met Asp Ile Pro Leu Leu Phe Glu Asn Asp Tyr Gln Asp Trp Phe
        115                 120                 125

Asp Gln Ile Trp Leu Val Ala Val Ser Pro Gln Val Gln Gly Gln Arg
130                 135                 140

Leu Met Lys Arg Asn His Leu Ser Ala Glu Glu Ala Gly Met Arg Ile
145                 150                 155                 160

Ala Ser Gln Met Pro Leu Ala Glu Lys Leu Pro Tyr Ala Ser Leu Val
                165                 170                 175

Ile Asp Asn Asn Gly Asn Ile Asp Asp Leu Lys Lys Lys Val Lys Gly
            180                 185                 190

Ala Ile Lys Asp Leu Ala Asn Leu Val
        195                 200

<210> SEQ ID NO 101
<211> LENGTH: 187
<212> TYPE: PRT
<213> ORGANISM: Pseudomonas aeruginosa

<400> SEQUENCE: 101

Met Asp His Tyr Leu Asp Ile Arg Leu Arg Pro Asp Pro Glu Phe Pro
1               5                   10                  15

Pro Ala Gln Leu Met Ser Val Leu Phe Gly Lys Leu Ala Gln Ala Leu
                20                  25                  30

Val Ala Gln Gly Gly Asp Arg Ile Gly Val Ser Phe Pro Asp Leu Asp
            35                  40                  45

Glu Ser Arg Ser Arg Leu Gly Glu Arg Leu Arg Ile His Ala Ser Ala
        50                  55                  60

Asp Asp Leu Arg Ala Leu Leu Ala Arg Pro Trp Leu Glu Gly Leu Arg
65                  70                  75                  80

Asp His Leu Gln Phe Gly Glu Pro Ala Val Val Pro His Pro Thr Pro
                85                  90                  95

Tyr Arg Gln Val Ser Arg Val Gln Val Lys Ser Asn Pro Glu Arg Leu
                100                 105                 110

Arg Arg Arg Leu Met Arg Arg His Asp Leu Ser Glu Glu Glu Ala Arg
                115                 120                 125

Lys Arg Ile Pro Asp Thr Val Ala Arg Ala Leu Asp Leu Pro Phe Val
130                 135                 140

Thr Leu Arg Ser Gln Ser Thr Gly Gln His Phe Arg Leu Phe Ile Arg
145                 150                 155                 160

His Gly Pro Leu Gln Ala Thr Ala Glu Glu Gly Gly Phe Thr Cys Tyr
                165                 170                 175

Gly Leu Ser Lys Gly Gly Phe Val Pro Trp Phe
                180                 185

<210> SEQ ID NO 102
<211> LENGTH: 187
<212> TYPE: PRT
<213> ORGANISM: Pseudomonas aeruginosa

<400> SEQUENCE: 102

Met Asp His Tyr Leu Asp Ile Arg Leu Arg Pro Asp Pro Glu Phe Pro
1               5                   10                  15

Pro Ala Gln Leu Met Ser Val Leu Phe Gly Lys Leu Ala Gln Ala Leu
                20                  25                  30

Val Ala Gln Gly Gly Asp Arg Ile Gly Val Ser Phe Pro Asp Leu Asp
                35                  40                  45

Glu Cys Arg Ser Arg Leu Gly Glu Arg Leu Arg Ile His Ala Ser Ala
        50                  55                  60

Asp Asp Leu Arg Ala Leu Leu Ala Arg Pro Trp Leu Glu Gly Leu Arg
65                  70                  75                  80

Asp His Leu Gln Phe Gly Glu Pro Ala Val Val Pro His Pro Thr Pro
                85                  90                  95

Tyr Arg Gln Val Ser Arg Val Gln Val Lys Ser Asn Pro Glu Arg Leu
                100                 105                 110

Arg Arg Arg Leu Met Arg Arg His Asp Leu Ser Glu Glu Glu Ala Arg
                115                 120                 125

Lys Arg Ile Pro Asp Thr Val Ala Arg Ala Leu Asp Leu Pro Phe Val
130                 135                 140

Thr Leu Arg Ser Gln Ser Thr Gly Gln His Phe Arg Leu Phe Ile Arg
145                 150                 155                 160

His Gly Pro Leu Gln Ala Thr Ala Glu Glu Gly Gly Phe Thr Cys Tyr
                165                 170                 175

Gly Leu Ser Lys Gly Gly Phe Val Pro Trp Phe
                180                 185

<210> SEQ ID NO 103
<211> LENGTH: 20
<212> TYPE: RNA
<213> ORGANISM: Artificial Sequence
<220> FEATURE:
<223> OTHER INFORMATION: Synthetic oligonucleotide

<400> SEQUENCE: 103
guucacugcc guauaggcag                                            20

<210> SEQ ID NO 104
<211> LENGTH: 187
<212> TYPE: PRT
<213> ORGANISM: Pseudomonas aeruginosa

<400> SEQUENCE: 104

```
Met Asp His Tyr Leu Asp Ile Arg Leu Arg Pro Asp Pro Glu Phe Pro
1               5                   10                  15

Pro Ala Gln Leu Met Ser Val Leu Phe Gly Lys Leu His Gln Ala Leu
            20                  25                  30

Val Ala Gln Gly Gly Asp Arg Ile Gly Val Ser Phe Pro Asp Leu Asp
        35                  40                  45

Glu Ser Arg Ser Arg Leu Gly Glu Arg Leu Arg Ile His Ala Ser Ala
    50                  55                  60

Asp Asp Leu Arg Ala Leu Leu Ala Arg Pro Trp Leu Glu Gly Leu Arg
65                  70                  75                  80

Asp His Leu Gln Phe Gly Glu Pro Ala Val Val Pro His Pro Thr Pro
                85                  90                  95

Tyr Arg Gln Val Ser Arg Val Gln Ala Lys Ser Asn Pro Glu Arg Leu
            100                 105                 110

Arg Arg Arg Leu Met Arg Arg His Asp Leu Ser Glu Glu Glu Ala Arg
        115                 120                 125

Lys Arg Ile Pro Asp Thr Val Ala Arg Ala Leu Asp Leu Pro Phe Val
    130                 135                 140

Thr Leu Arg Ser Gln Ser Thr Gly Gln His Phe Arg Leu Phe Ile Arg
145                 150                 155                 160

His Gly Pro Leu Gln Val Thr Ala Glu Glu Gly Gly Phe Thr Cys Tyr
                165                 170                 175

Gly Leu Ser Lys Gly Gly Phe Val Pro Trp Phe
            180                 185
```

<210> SEQ ID NO 105
<211> LENGTH: 187
<212> TYPE: PRT
<213> ORGANISM: Artificial sequence
<220> FEATURE:
<223> OTHER INFORMATION: Synthetic sequence

<400> SEQUENCE: 105

```
Met Asp His Tyr Leu Asp Ile Arg Leu Arg Pro Asp Pro Glu Phe Pro
1               5                   10                  15

Pro Ala Gln Leu Met Ser Val Leu Phe Gly Lys Leu Ala Gln Ala Leu
            20                  25                  30

Val Ala Gln Gly Gly Asp Arg Ile Gly Val Ser Phe Pro Asp Leu Asp
        35                  40                  45

Glu Ser Arg Ser Arg Leu Gly Glu Arg Leu Arg Ile His Ala Ser Ala
    50                  55                  60

Asp Asp Leu Arg Ala Leu Leu Ala Arg Pro Trp Leu Glu Gly Leu Arg
65                  70                  75                  80

Asp His Leu Gln Phe Gly Glu Pro Ala Val Val Pro His Pro Thr Pro
                85                  90                  95

Tyr Arg Gln Val Ser Arg Val Gln Ala Lys Ser Asn Pro Glu Arg Leu
            100                 105                 110

Arg Arg Arg Leu Met Arg Arg His Asp Leu Ser Glu Glu Glu Ala Arg
        115                 120                 125

Lys Arg Ile Pro Asp Thr Val Ala Arg Ala Leu Asp Leu Pro Phe Val
    130                 135                 140
```

```
Thr Leu Arg Ser Gln Ser Thr Gly Gln His Phe Arg Leu Phe Ile Arg
145                 150                 155                 160

His Gly Pro Leu Gln Val Thr Ala Glu Glu Gly Gly Phe Thr Cys Tyr
                165                 170                 175

Gly Leu Ser Lys Gly Gly Phe Val Pro Trp Phe
            180                 185

<210> SEQ ID NO 106
<211> LENGTH: 184
<212> TYPE: PRT
<213> ORGANISM: Artificial sequence
<220> FEATURE:
<223> OTHER INFORMATION: Synthetic sequence

<400> SEQUENCE: 106

Met Asp His Tyr Leu Glu Ile Arg Val Leu Pro Asp Pro Glu Phe Ser
1               5                   10                  15

Ser Glu Met Leu Met Ala Ala Leu Phe Ala Lys Leu Ala Arg Val Leu
            20                  25                  30

Gly Ala Arg Gly Gln Gly Asp Ile Gly Val Ser Phe Pro Asp Val Asn
        35                  40                  45

Val Met Pro Gly Ala Arg Leu Arg Leu His Gly Ser Ala Gln Ala Leu
50                  55                  60

Gln Ala Leu Glu Ala Ser Thr Trp Arg Lys Gly Leu Thr Asp Tyr Cys
65                  70                  75                  80

Gln Cys Ser Pro Val Thr Pro Val Pro Glu Ile Lys Gly Trp Arg Val
                85                  90                  95

Val Ser Arg Val Gln Val Lys Ser Asn Pro Gln Arg Leu Leu Arg Arg
            100                 105                 110

Ser Val Lys Lys Gly Trp Leu Thr Glu Glu Gln Ala Ile Glu Arg Leu
        115                 120                 125

Ala Thr Gln Ala Glu Gln Arg Thr Asp Leu Pro Phe Leu Asn Met Lys
130                 135                 140

Ser Leu Ser Ser Gln Gln Leu Phe Lys Leu Phe Ile Arg His Gly Asp
145                 150                 155                 160

Leu Leu Lys Glu Pro Val Lys Gly Glu Phe Ser Ser Tyr Gly Leu Ser
                165                 170                 175

Ala Thr Ala Thr Ile Pro Trp Phe
            180

<210> SEQ ID NO 107
<211> LENGTH: 202
<212> TYPE: PRT
<213> ORGANISM: Artificial sequence
<220> FEATURE:
<223> OTHER INFORMATION: Synthetic sequence

<400> SEQUENCE: 107

Met Asn Phe Tyr Gln Glu Ile Thr Leu Leu Pro Asp Ala Glu Val Ser
1               5                   10                  15

Leu Tyr Phe Leu Trp Ser Lys Val Tyr Gly Gln Leu Ala Ile Ala Leu
            20                  25                  30

Ala Asp Val Arg Asn Arg Tyr Gly Ile Asp Thr Ile Gly Val Asn Phe
        35                  40                  45

Pro His Tyr Val Tyr Glu Glu Gln Asn His Lys Val Val Ala Ala Arg
50                  55                  60

Leu Gly Asp Gln Leu Arg Ile Phe Ala Leu Ala Glu Asn Asp Leu Glu
```

```
                65                  70                  75                  80
Lys Leu Gln Ile Asn Gln Trp Leu Glu Arg Leu Ser Asp Tyr Val His
                    85                  90                  95

Ile Lys Arg Ile Ser Lys Ile Glu Pro Asn Lys Val Thr Gly Tyr Val
                100                 105                 110

Val Val Lys Arg Tyr Arg Tyr Pro Ser Leu Asp Lys Val Ala Leu Arg
                115                 120                 125

Phe Ala Gln Phe Arg Lys Ile Asn Phe Glu Glu Ala Arg Lys His Cys
130                 135                 140

Thr Lys Tyr Lys His Gln Ala Lys Asn Tyr Pro Phe Ile Met Leu Lys
145                 150                 155                 160

Ser Gln Ser Asn Gln Glu Tyr Tyr Lys Leu Ser Ile Arg Gln Glu Asn
                165                 170                 175

Ala Gln Glu Ser Val Ser Gly Arg Phe Asn Val Tyr Gly Ile Asn Ser
                180                 185                 190

Ala Thr Gly Ile Val Thr Val Pro Asn Trp
                195                 200

<210> SEQ ID NO 108
<211> LENGTH: 203
<212> TYPE: PRT
<213> ORGANISM: Acinetobacter sp. ADP1

<400> SEQUENCE: 108

Met Asp Ala Asn Tyr Tyr Leu Asp Ile Arg Val Leu Glu Ser Ser Asp
1               5                   10                  15

Asp Thr Asp Leu Lys Leu Gly His Ile Arg Asn Gln Ile Tyr Thr Val
                20                  25                  30

Ile His Gly Ala Phe Arg Lys Leu Pro Ala His Tyr Ala Leu Ala Leu
            35                  40                  45

Glu Met Ser Asp Lys Leu Lys Ala Lys Gln Glu Gln Phe Glu Lys Lys
        50                  55                  60

His Gly Arg Ser Ala Lys Pro Asn Phe Asp Ile Leu Arg Ile Phe Ala
65                  70                  75                  80

Glu Lys Gln Asp Glu Leu Asp Glu Leu Val Glu Ala Ile Lys Gly His
                85                  90                  95

Trp Lys Ile Arg Asp Tyr Thr Val Leu Gly Val Ala Ile Ala Val Pro
                100                 105                 110

Thr Ala Lys Ile Ser Gly Trp Lys Ser Tyr Arg Lys Phe Arg Ile Pro
            115                 120                 125

Thr Gln Lys Ala Glu Arg Thr Lys Leu Ser His Gln Asn Glu Pro Leu
        130                 135                 140

Arg Asp Arg Arg Leu Lys Thr Ala Lys Gly Met Pro Phe Phe Gln Val
145                 150                 155                 160

Ile Ser Gln Ser Thr Gly Gln Gly Phe Thr Val Ile Ile Asp Val Gln
                165                 170                 175

Glu Ser Glu Asn Ala Gly Tyr Gly Leu Pro Asp Ser Tyr Gly Leu Ala
                180                 185                 190

Arg Lys Glu Ser Pro Phe Ala Leu Pro Val Phe
            195                 200

<210> SEQ ID NO 109
<211> LENGTH: 203
<212> TYPE: PRT
<213> ORGANISM: Artificial sequence
<220> FEATURE:
```

<223> OTHER INFORMATION: Synthetic sequence

<400> SEQUENCE: 109

Met Asp Ala Asn Tyr Tyr Leu Asp Ile Arg Val Leu Glu Ser Ser Asp
1               5                   10                  15

Asp Thr Asp Leu Lys Leu Gly His Ile Arg Asn Gln Ile Tyr Thr Val
                20                  25                  30

Ile Ala Gly Ala Phe Arg Lys Leu Pro Ala His Tyr Ala Leu Ala Leu
            35                  40                  45

Glu Met Ser Asp Lys Leu Lys Ala Lys Gln Glu Gln Phe Glu Lys Lys
        50                  55                  60

His Gly Arg Ser Ala Lys Pro Asn Phe Asp Ile Leu Arg Ile Phe Ala
65                  70                  75                  80

Glu Lys Gln Asp Glu Leu Asp Glu Leu Val Glu Ala Ile Lys Gly His
                85                  90                  95

Trp Lys Ile Arg Asp Tyr Thr Val Leu Gly Val Ala Ile Ala Val Pro
            100                 105                 110

Thr Ala Lys Ile Ser Gly Trp Lys Ser Tyr Arg Lys Phe Arg Ile Pro
        115                 120                 125

Thr Gln Lys Ala Glu Arg Thr Lys Leu Ser His Gln Asn Glu Pro Leu
    130                 135                 140

Arg Asp Arg Arg Leu Lys Thr Ala Lys Gly Met Pro Phe Phe Gln Val
145                 150                 155                 160

Ile Ser Gln Ser Thr Gly Gln Gly Phe Thr Val Ile Ile Asp Val Gln
                165                 170                 175

Glu Ser Glu Asn Ala Gly Tyr Gly Leu Pro Asp Ser Tyr Gly Leu Ala
            180                 185                 190

Arg Lys Glu Ser Pro Phe Ala Leu Pro Val Phe
        195                 200

<210> SEQ ID NO 110
<211> LENGTH: 224
<212> TYPE: PRT
<213> ORGANISM: Shewanella sp. W3-18-1

<400> SEQUENCE: 110

Met Lys Tyr Tyr Leu Asp Ile Thr Leu Leu Pro Asp Ala Glu Ala Asn
1               5                   10                  15

Leu Gly Phe Leu Trp His Lys Val Tyr Gln Gln Ile His Leu Met Leu
                20                  25                  30

Val Glu His Lys Val Ser Val Glu Asn Ser Ala Ile Gly Leu Ser Phe
            35                  40                  45

Pro Lys Tyr Asp Ala Lys Ser Phe Ser Asp Asn Thr Lys Phe Pro Leu
        50                  55                  60

Gly Asp Lys Leu Arg Leu Phe Ala Gly Thr Glu Gln Gln Leu Ala Asp
65                  70                  75                  80

Leu Lys Val Ala Gln Trp Leu Ala Arg Leu Ala Asp Tyr Val His Ile
                85                  90                  95

Lys Ala Ile Lys Ala Val Pro Asp Asn Val Ser Glu Tyr Ala Tyr Phe
            100                 105                 110

Lys Arg Arg His Phe Lys Ser Pro Asp Lys Leu Arg Asn Ile Asp
        115                 120                 125

Ala Arg Ala Ile Val Ile Ala Gln Lys Asn Gly Phe Ala Ile Asn Glu
    130                 135                 140

Val Lys Thr Arg Leu Leu Ala Ser Ile Asp Asn Leu Asp Thr Lys Ser

```
                145                 150                 155                 160
Lys Leu Pro Phe Ile Asn Leu Arg Ser Leu Ser Thr Glu Lys Asp Val
                    165                 170                 175

Ser Pro Ala Asp Arg Arg Lys Phe Leu Leu Phe Ile Glu Cys Glu Lys
                    180                 185                 190

Val Thr Lys Pro Ser Gln Asn Asn Gly Leu Phe Asn Cys Tyr Gly Leu
                    195                 200                 205

Ser Arg Arg Ala Gln Thr Glu Gln Ala Ala Val Pro Trp Phe Glu Gly
                    210                 215                 220
```

<210> SEQ ID NO 111
<211> LENGTH: 224
<212> TYPE: PRT
<213> ORGANISM: Artificial sequence
<220> FEATURE:
<223> OTHER INFORMATION: Synthetic sequence

<400> SEQUENCE: 111

```
Met Lys Tyr Tyr Leu Asp Ile Thr Leu Leu Pro Asp Ala Glu Ala Asn
1               5                   10                  15

Leu Gly Phe Leu Trp His Lys Val Tyr Gln Gln Ile Ala Leu Met Leu
                20                  25                  30

Val Glu His Lys Val Ser Val Glu Asn Ser Ala Ile Gly Leu Ser Phe
                35                  40                  45

Pro Lys Tyr Asp Ala Lys Ser Phe Ser Asp Asn Thr Lys Phe Pro Leu
    50                  55                  60

Gly Asp Lys Leu Arg Leu Phe Ala Gly Thr Glu Gln Gln Leu Ala Asp
65                  70                  75                  80

Leu Lys Val Ala Gln Trp Leu Ala Arg Leu Ala Asp Tyr Val His Ile
                85                  90                  95

Lys Ala Ile Lys Ala Val Pro Asp Asn Val Ser Glu Tyr Ala Tyr Phe
                100                 105                 110

Lys Arg Arg His Phe Lys Ser Pro Asp Lys Leu Arg Asn Ile Asp
                115                 120                 125

Ala Arg Ala Ile Val Ile Ala Gln Lys Asn Gly Phe Ala Ile Asn Glu
            130                 135                 140

Val Lys Thr Arg Leu Leu Ala Ser Ile Asp Asn Leu Asp Thr Lys Ser
145                 150                 155                 160

Lys Leu Pro Phe Ile Asn Leu Arg Ser Leu Ser Thr Glu Lys Asp Val
                    165                 170                 175

Ser Pro Ala Asp Arg Arg Lys Phe Leu Leu Phe Ile Glu Cys Glu Lys
                    180                 185                 190

Val Thr Lys Pro Ser Gln Asn Asn Gly Leu Phe Asn Cys Tyr Gly Leu
                    195                 200                 205

Ser Arg Arg Ala Gln Thr Glu Gln Ala Ala Val Pro Trp Phe Glu Gly
                    210                 215                 220
```

<210> SEQ ID NO 112
<211> LENGTH: 203
<212> TYPE: PRT
<213> ORGANISM: Artificial sequence
<220> FEATURE:
<223> OTHER INFORMATION: Synthetic sequence

<400> SEQUENCE: 112

```
Met Asn Trp Tyr Gln Glu Ile Thr Leu Ile Asp Gln Asp Glu Ile Ser
1               5                   10                  15
```

```
Leu Tyr Phe Ile Trp Ser Lys Val Tyr Thr Gln Leu Ala Ile Ala Phe
                20                  25                  30

Ala Glu His Ser Asn Glu Gln Gly Arg Ile Ser Phe Gly Val Ser Phe
            35                  40                  45

Pro Gln Tyr Arg Ile Asn Glu Gln Lys Lys Ile Gly Phe Leu Gly Thr
        50                  55                  60

Lys Ile Arg Val Phe Ala Ser Ser Glu Asn Asp Leu Gln Gln Leu Asn
65                  70                  75                  80

Leu Gly Lys Trp Leu Glu Arg Phe Ile Asp Tyr Val His Ile Thr Gln
                85                  90                  95

Pro Arg Glu Val Pro Arg Ala Lys Ile Thr Gly Tyr Ala His Tyr Tyr
            100                 105                 110

Arg Val Asn His Arg Met Ser Val Glu Glu Arg Ile Val His Gln Ala
        115                 120                 125

Gln Arg Arg Asn Ile Ser Leu Asp Gln Ala Arg Gln His Phe Lys Gln
130                 135                 140

Tyr Val Glu Gln Pro Val Val Glu Pro Tyr Val Ser Leu Lys Ser Leu
145                 150                 155                 160

Ser Ala Lys Arg Glu Glu Asn Val Asp Arg Pro Tyr Arg Leu Tyr Ile
                165                 170                 175

Gly Lys Ser Leu Val Asp Glu Ala Arg Asp Gly Met Phe Gly Thr Tyr
            180                 185                 190

Gly Leu Ser Arg Met Thr Thr Val Pro Glu Phe
        195                 200

<210> SEQ ID NO 113
<211> LENGTH: 21
<212> TYPE: RNA
<213> ORGANISM: Escherichia coli

<400> SEQUENCE: 113
guucacugcc guacaggcag c                                      21

<210> SEQ ID NO 114
<211> LENGTH: 21
<212> TYPE: RNA
<213> ORGANISM: Dichelobacter nodosus

<400> SEQUENCE: 114
guucacugcc guacaggcag c                                      21

<210> SEQ ID NO 115
<211> LENGTH: 21
<212> TYPE: RNA
<213> ORGANISM: Acinetobacter sp. ADP1

<400> SEQUENCE: 115
cuuaacugcc gcacaggcag c                                      21

<210> SEQ ID NO 116
<211> LENGTH: 28
<212> TYPE: RNA
<213> ORGANISM: Acinetobacter sp. ADP1

<400> SEQUENCE: 116
cuuaacugcc gcacaggcag cuuagaaa                               28

<210> SEQ ID NO 117
<211> LENGTH: 21
```

```
<212> TYPE: RNA
<213> ORGANISM: Acinetobacter sp. ADP1

<400> SEQUENCE: 117
cuucacuacc gcacagguag c                                              21

<210> SEQ ID NO 118
<211> LENGTH: 28
<212> TYPE: RNA
<213> ORGANISM: Acinetobacter sp. ADP1

<400> SEQUENCE: 118
cuucacuacc gcacagguag cuuagaaa                                       28

<210> SEQ ID NO 119
<211> LENGTH: 21
<212> TYPE: RNA
<213> ORGANISM: Shewanella sp. W3-18-1

<400> SEQUENCE: 119
guucaccgcc acacaggcgg c                                              21

<210> SEQ ID NO 120
<211> LENGTH: 28
<212> TYPE: RNA
<213> ORGANISM: Shewanella sp. W3-18-1

<400> SEQUENCE: 120
guucaccgcc acacaggcgg cuuagaaa                                       28

<210> SEQ ID NO 121
<211> LENGTH: 21
<212> TYPE: RNA
<213> ORGANISM: Shewanella sp. W3-18-1

<400> SEQUENCE: 121
guucacugcc gcacaggcag c                                              21

<210> SEQ ID NO 122
<211> LENGTH: 28
<212> TYPE: RNA
<213> ORGANISM: Shewanella sp. W3-18-1

<400> SEQUENCE: 122
guucacugcc gcacaggcag cuuagaaa                                       28

<210> SEQ ID NO 123
<211> LENGTH: 22
<212> TYPE: RNA
<213> ORGANISM: Acinetobacter baumannii

<400> SEQUENCE: 123
guucauggcg gcauacgcca uu                                             22
```

ENDORIBONUCLEASE COMPOSITIONS AND METHODS OF USE THEREOF

CROSS-REFERENCE

This application is a divisional of U.S. patent application Ser. No. 13/671,120, and claims the benefit of International Application No. PCT/US2011/035775, filed May 9, 2011, U.S. Provisional Patent Application No. 61/333,163, filed May 10, 2010, U.S. Provisional Patent Application No. 61/365,627, filed Jul. 19, 2010, and U.S. Provisional Patent Application No. 61/413,287, filed Nov. 12, 2010, each of which applications is incorporated herein by reference in its entirety.

STATEMENT REGARDING FEDERALLY SPONSORED RESEARCH

This invention was made with government support under Grant No. T32 GM07232 awarded by the National Institutes of Health and Grant No. MCB-0950971 awarded by the National Science Foundation. The government has certain rights in the invention.

INCORPORATION BY REFERENCE OF SEQUENCE LISTING PROVIDED AS A TEXT FILE

A Sequence Listing is provided herewith as a text file, "BERK-118CIP_Sequence_Listing" created on Jun. 9, 2015 and having a size of 124 KB. The contents of the text file are incorporated by reference herein in their entirety.

BACKGROUND

DNA restriction enzymes transformed molecular biology in the 1970s by making it possible to cleave specific DNA sequences at will. Sequencing of RNA molecules currently entails copying the RNA into a DNA strand that is then sequenced by conventional methods. This approach, also known as RNASeq, is robust and can yield many millions of sequence reads. However, the necessity of generating cDNA introduces inherent bias due to sequence-dependent efficiencies of individual steps.

LITERATURE

Carte et al. (2008) *Genes Dev.* 22:3489; U.S. Patent Publication No. 2010/0093026.

SUMMARY OF THE INVENTION

The present disclosure provides variant Csy4 endoribonucleases, nucleic acids encoding the variant Csy4 endoribonucleases, and host cells genetically modified with the nucleic acids. The variant Csy4 endoribonucleases find use in a variety of applications, which are also provided. The present disclosure also provides methods of detecting a specific sequence in a target polyribonucleotide; and methods of regulating production of a target RNA in a eukaryotic cell.

BRIEF DESCRIPTION OF THE DRAWINGS

FIGS. 1A-1C depict specific recognition of a pre-crRNA substrate by Pa14Csy4. The nucleotide sequence depicted is 5'-GUUCACUGCCGUAUAGGCAGCUAAGAAA-3' (SEQ ID NO:1).

FIGS. 5A-5BD present an amino acid sequence alignment of various Csy4 polypeptides, as well as the nucleotide sequences of RNA sequences recognized by each Csy4 polypeptide.

FIG. 6 depicts examples of amino acid sequences of enzymatically inactive, sequence-specific endoribonucleases.

FIG. 11A-11G depicts sequence-specific Csy4 endoribonucleases and mutant, inactive versions of these endoribonucleases that can be reactivated in the presence of imidazole. The mutated residue is inferred from the conserved histidine (starred) of the alignment depicted in FIG. 4. This figure also depicts the cognate RNA substrates for the Csy4 variants.

FIGS. 13A-13B depict cleavage rate constants (before and after normalization) for six Csy4 variants paired with nine possible RNA substrates.

DEFINITIONS

Figure 2A:
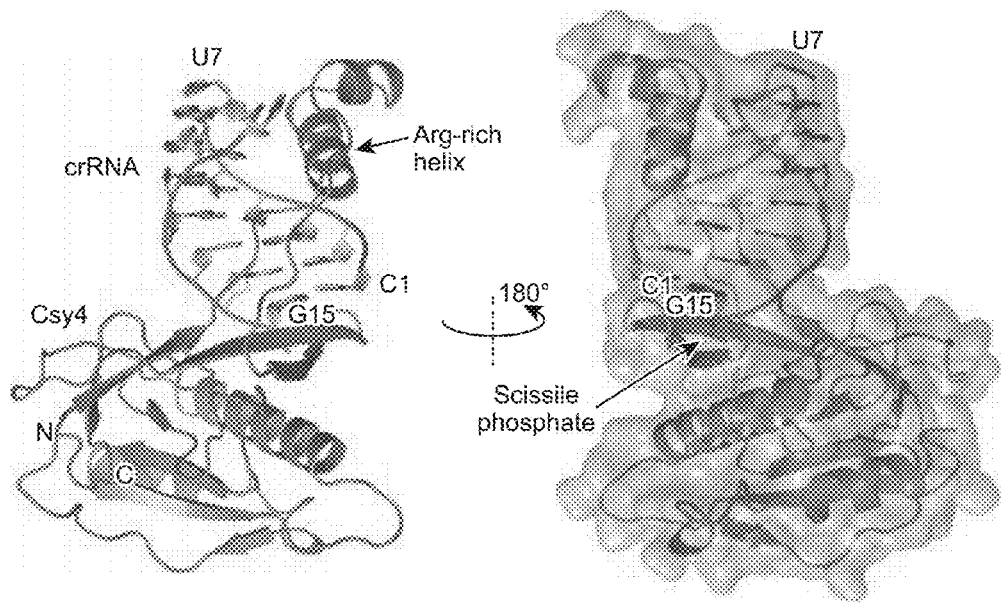
FIGS. 2A-2C depict crystal structures of Csy4 bound to RNA substrate.

As used herein, "polyribonucleotide" refers to a polymeric form of ribonucleotides, and includes RNA, RNA containing deoxyribonucleotide(s), and DNA containing ribonucleotide(s). A polyribonucleotide can in some cases include one or more modified nucleotides (e.g., deoxyinosine, deoxyuridine or hydroxymethyldeoxyuridine). In some cases, a polyribonucleotide consists of a ribonucleotides only (i.e., does not include any deoxyribonucleotides). In some cases, a polyribonucleotide comprises ribonucleotides, and one or more modified ribonucleotides, but does not include any deoxyribonucleotides. In other cases, a polyribonucleotide comprises ribonucleotides, and may comprise one or more modified ribonucleotides, and one or more deoxyribonucleotides (including modified deoxyribonucleotides). In some cases, where a polyribonucleotide comprises one or more deoxyribonucleotides, the deoxyribonucleotides comprise from about 50% to about 40%, from about 40% to about 30%, from about 30% to about 20%, from about 20% to about 10%, from about 10% to about 1%, or less than 1%, of the total nucleotides in the polyribonucleotide.

The terms "nucleic acid" and "polynucleotide" are used interchangeably and refer to a polymeric form of nucleotides of any length, either deoxyribonucleotides or ribonucleotides, or analogs thereof. Non-limiting examples of polynucleotides include linear and circular nucleic acids, messenger RNA (mRNA), cDNA, recombinant polynucleotides, vectors, probes, and primers.

A "biological sample" encompasses a variety of sample types obtained from a cell, extracellular matter, a tissue, or a multicellular organism. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides. The term "biological sample" encompasses a clinical sample, and also includes cells in culture, cell supernatants, cell lysates, serum, plasma, biological fluid (e.g., cerebrospinal fluid, bronchoalveolar lavage fluid, urine, blood, a blood fraction (e.g., plasma; serum), sputum, and the like), and tissue samples. In some cases, a biological sample comprises cells. In other cases, a biological sample is cell free.

The term "operably linked" refers to functional linkage between molecules to provide a desired function. For example, "operably linked" in the context of nucleic acids refers to a functional linkage between nucleic acids to provide a desired function such as transcription, translation, and the like, e.g., a functional linkage between a nucleic acid expression control sequence (such as a promoter, signal sequence, or array of transcription factor binding sites) and a second polynucleotide, wherein the expression control sequence affects transcription and/or translation of the second polynucleotide. "Operably linked" in the context of a polypeptide refers to a functional linkage between amino acid sequences (e.g., of different domains) to provide for a described activity of the polypeptide.

"Isolated" refers to a protein or nucleic acid that, if naturally occurring, is in an environment different from that in which it may naturally occur. "Isolated" is meant to include proteins or nucleic acids that are within samples that are substantially enriched for the protein or nucleic acid of interest and/or in which the protein or nucleic acid of interest is partially or substantially purified. Where the protein or nucleic acid is not naturally occurring, "isolated" indicates the protein or nucleic acid has been separated from an environment in which it was made by either synthetic or recombinant means.

"Substantially pure" indicates that an entity (e.g., polypeptide or a nucleic acid) makes up greater than about 50% of the total content of the composition (e.g., total protein of the composition) and typically, greater than about 60% of the total protein content. In some embodiments, "substantially pure" refers to compositions in which at least 75%, at least 85%, at least 90% or more of the total composition is the entity of interest (e.g. 95%, of the total protein). In some embodiments, the protein or nucleic acid of interest will make up greater than about 90%, greater than about 95%, greater than about 98%, or greater than about 99%, of the total protein or nucleic acid in the composition.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a site-specific endoribonuclease" includes a plurality of such site-specific endoribonucleases and reference to "the target polyribonucleotide" includes reference to one or more target polyribonucleotides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides variant Csy4 endoribonucleases, nucleic acids encoding the variant Csy4 endoribonucleases, and host cells genetically modified with the nucleic acids. The variant Csy4 endoribonucleases find use in a variety of applications, which are also provided. The present disclosure also provides methods of detecting a specific sequence in a target polyribonucleotide; and methods of regulating production of a target RNA in a eukaryotic cell.

Methods of Detecting a Sequence in a Target Polyribonucleotide

The present disclosure provides a method of detecting a sequence in a target polyribonucleotide. The methods are useful for detecting the presence of a particular sequence in a polyribonucleotide, and can therefore be used to detect a polyribonucleotide comprising a particular sequence. For example, the method can be used to detect the presence of a polyribonucleotide of a pathogen in a sample (e.g., in a biological sample).

A subject method can detect as few as 100 copies, down to a single copy, of a target polyribonucleotide. Thus, e.g., a subject method can detect from 1 to about 5, from about 5 to about 10, from about 10 to about 50, or from about 50 to about 100, or more than 100, copies of a target polyribonucleotide in a sample (e.g., in a single cell, in a single embryo, or other biological sample). A subject method is thus useful for various forensic, research, and diagnostic applications.

In some embodiments, a subject method of detecting a specific sequence in a target polyribonucleotide comprises: a) contacting the target polyribonucleotide with a oligonucleotide probe comprising the specific sequence and an enzymatically active sequence-specific Csy4 endoribonuclease under conditions that favor duplex formation between the oligonucleotide probe and the target polyribonucleotide, wherein the duplex is cleaved by the Csy4 endoribonuclease; and b) detecting specific binding between the oligonucleotide probe and the target polyribonucleotide, wherein detection of duplex formation between the oligonucleotide probe and the target polyribonucleotide indicates the presence of the specific sequence in the target polyribonucleotide.

In some cases, the oligonucleotide probe is linked to a peptide, and the peptide is released upon cleavage of the duplex by the Csy4 endoribonuclease; in these cases, the detection step involves detection of the released peptide. For example, the released peptide is detected by binding to an antibody specific for the peptide, e.g., where the antibody is immobilized. In some embodiments, the target polyribonucleotide is immobilized on a solid support. Target polyribonucleotides include any of a variety of polynucleotides, e.g., the target polyribonucleotide can be a polyribonucleotide of a pathogen.

As noted above, in some embodiments, the antibody or the target polynucleotide is immobilized on a solid support (insoluble support). Suitable insoluble supports include, but are not limited to agarose beads, magnetic beads, a test strip, a multi-well dish, and the like. The insoluble support can comprise a variety of substances (glass, polystyrene, polyvinyl chloride, polypropylene, polyethylene, polycarbonate, dextran, nylon, amylose, natural and modified celluloses, polyacrylamides, agaroses, and magnetite) and can be provided in a variety of forms, including, e.g., agarose beads, polystyrene beads, latex beads, magnetic beads, colloid metal particles, glass and/or silicon chips and surfaces, nitrocellulose strips, nylon membranes, sheets, wells of reaction trays (e.g., multi-well plates), plastic tubes, etc.

In some embodiments, the method generally involves: a) contacting a target polyribonucleotide with a sequence-specific endoribonuclease; and b) detecting cleavage fragments produced by site-specific cleavage of the target polyribonucleotide, where production of cleavage fragments expected upon cleavage at a specific sequence in the polyribonucleotide indicates the presence of the specific sequence.

In other embodiments, a subject method of detecting a sequence in a target polyribonucleotide involves: a) contacting a target polyribonucleotide with: i) a sequence-specific endoribonuclease; and ii) an oligonucleotide probe comprising a linked detection moiety, where the oligonucleotide probe comprises a specific, known nucleotide sequence; wherein the oligonucleotide probe forms a duplex with a complementary sequence in the target polyribonucleotide based on binding of the known nucleotide sequence present in the oligonucleotide probe to a complementary sequence in the target polyribonucleotide, and where the sequence-specific endoribonuclease cleaves the duplex in a sequence-specific manner, thereby releasing the detection moiety from the oligonucleotide probe; and b) detecting the released detection moiety, where release of the detection moiety indicates the presence of the specific sequence. In some embodiments, two or more different oligonucleotide probes are used, each comprising a different specific, known nucleotide sequence.

In some embodiments, the detection moiety is a polypeptide. The polypeptide can be detected using an immunological assay (e.g., an enzyme-linked immunosorbent assay (ELISA); a radioimmunoassay (RIA); etc.), using an antibody specific for the polypeptide detection moiety. The antibody specific for the polypeptide detection moiety can comprise a detectable label. The immunological assay can be carried out on a test strip (e.g., in a lateral flow assay) or other suitable medium such as a multi-well plate.

In some embodiments, the detection moiety is a fluorescent protein, where suitable fluorescent proteins are as described herein. In other embodiments, the detection moiety is luciferin or other substrate for luciferase. Suitable luciferins or other luciferase substrates include, e.g., luciferin (e.g., a firefly luciferin); an aminoluciferin; coelenterazine; a modified coelenterazine as described in U.S. Pat. No. 7,537,912; a coelenterazine analog as described in U.S. Patent Publication No. 2009/0081129 (e.g., a membrane permeant coelenterazine analog as described in U.S. Patent Publication No. 2009/0081129, e.g., one of Structures II, III, IV, V, and VI of U.S. Patent Publication No. 2009/0081129); aminoluciferin; dihydroluciferin; luciferin 6' methylether; or luciferin 6' chloroethylether. See, e.g., Branchini, B. R. et al. *Anal. Biochem.* 2010, 396, 290-296; and Mezzanotte, L. et al., In vivo bioluminescence imaging of murine xenograft cancer models with a red-shifted thermostable luciferase. *Mol. Imaging Biol.* (2009, Nov. 9, online; PubMed ID: 19937390).

Figure 7:
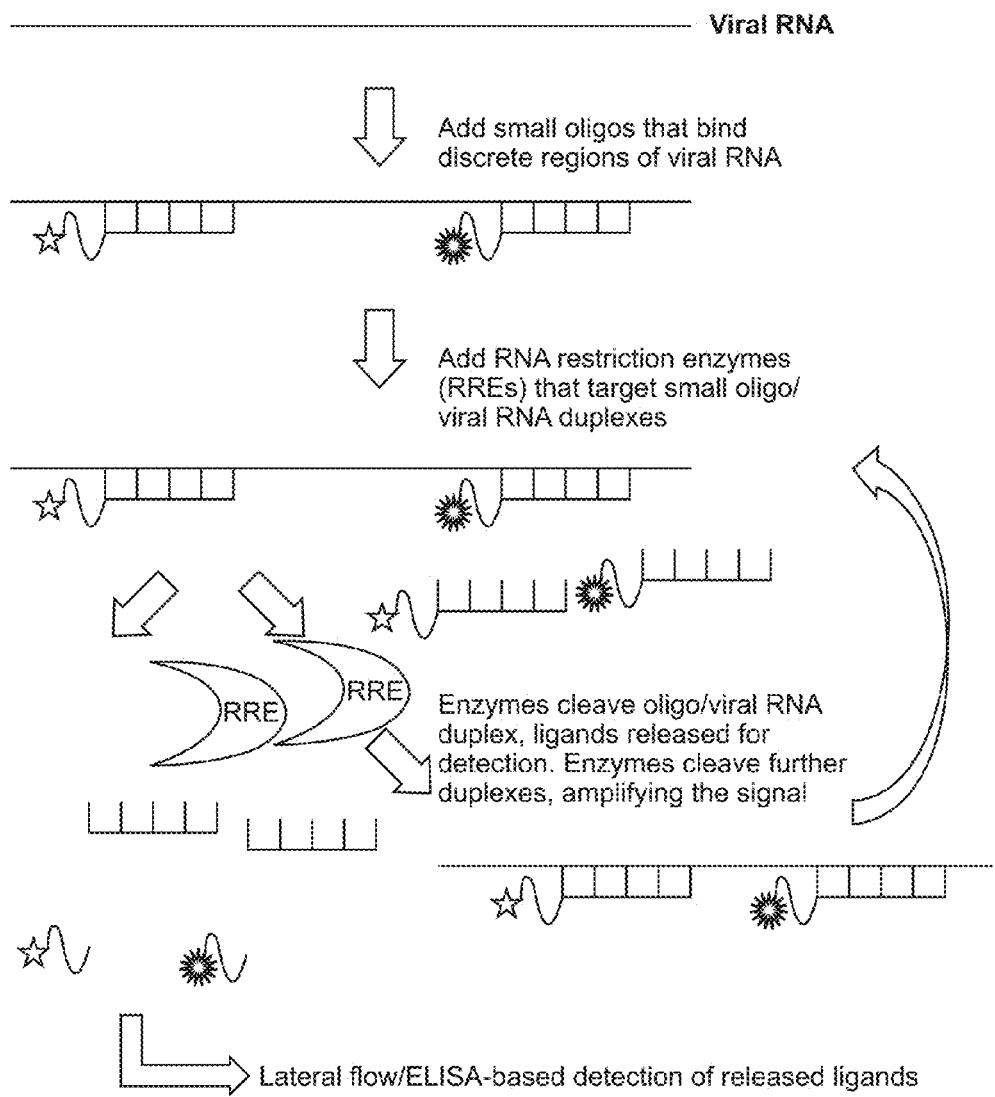
FIG. 7 depicts an example of a method for detecting a specific sequence in a target polyribonucleotide.

A non-limiting example of a subject detection method is illustrated schematically in FIG. 7. In the example depicted in FIG. 7, small oligonucleotides that bind discrete regions of a target polynucleotide (e.g., a viral RNA) are contacted with the target polynucleotide, where the oligonucleotides comprise detectable moieties (e.g., ligands; peptides; etc.). An enzymatically active, sequence-specific restriction endonuclease (RRE) that targets the oligonucleotide/viral RNA duplex is added. The enzyme cleaves the oligonucleotide/viral RNA duplex; and ligands are released for detection. The enzyme cleaves further duplexes, thereby amplifying the signal. Released ligands are detected using a lateral flow (e.g., test strip) or an immunological based assay (e.g., ELISA).

A suitable sequence-specific endoribonuclease is an enzymatically active, sequence-specific endoribonuclease. Endoribonucleases that are suitable for use in a subject detection method include endoribonucleases that bind to and cleave a substrate polyribonucleotide in a sequence-specific manner include enzymatically active polypeptides and that have at least about 85%, at least about 90%, at least about 95%, at least about 98%, at least about 99%, or 100%, amino acid sequence identity to an amino acid sequence set forth in FIG. 4 (Csy4 amino acid sequences).

Endoribonucleases that are suitable for use in a subject detection method include endoribonucleases that bind to and cleave a substrate polyribonucleotide in a sequence-specific manner include enzymatically active polypeptides and that have at least about 85%, at least about 90%, at least about 95%, at least about 98%, at least about 99%, or 100%, amino acid sequence identity to an amino acid sequence set forth in FIG. 5 or FIG. 11 (SEQ ID NO: 39, 79, 84, 90, 104, 108, or 110) (Csy4 amino acid sequences). FIG. 5 provides sequences specifically bound by the various endoribonucleases. In some cases, a suitable enzymatically active sequence-specific Csy4 endoribonuclease can comprise an amino acid sequence of a Csy4 amino acid sequence depicted in FIG. 5 or FIG. 11 (SEQ ID NO: 39, 79, 84, 90, 104, 108, or 110).

Figure 4:
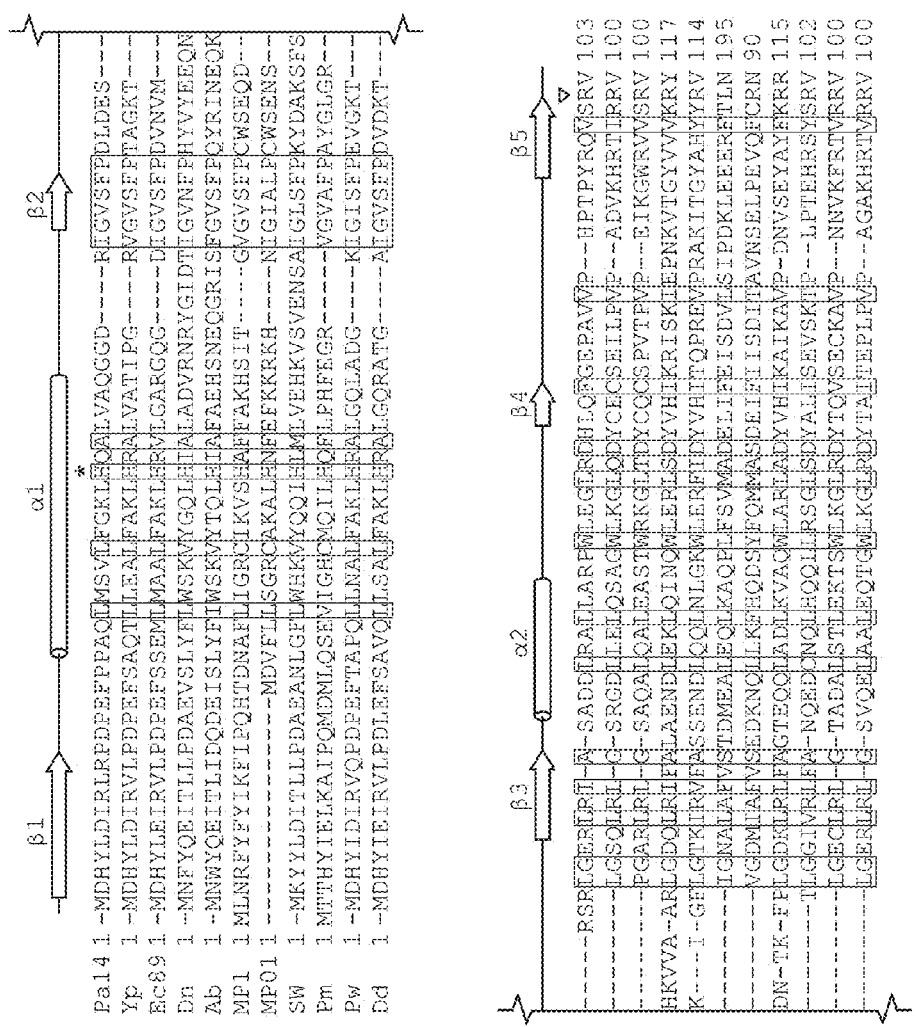
FIG. 4 depicts invariant amino acids among 12 Csy4 sequences. Pa (SEQ ID NO:8); Yp (SEQ ID NO:34); Ec89 (SEQ ID NO:39); Dn (SEQ ID NO:79); Ab (SEQ ID NO:84); MP1 (SEQ ID NO:2); MP01 (SEQ ID NO:3); SW (SEQ ID NO:4); Pm (SEQ ID NO:85); Pw (SEQ ID NO:13); and Dd (SEQ ID NO:10).
Figure 4:
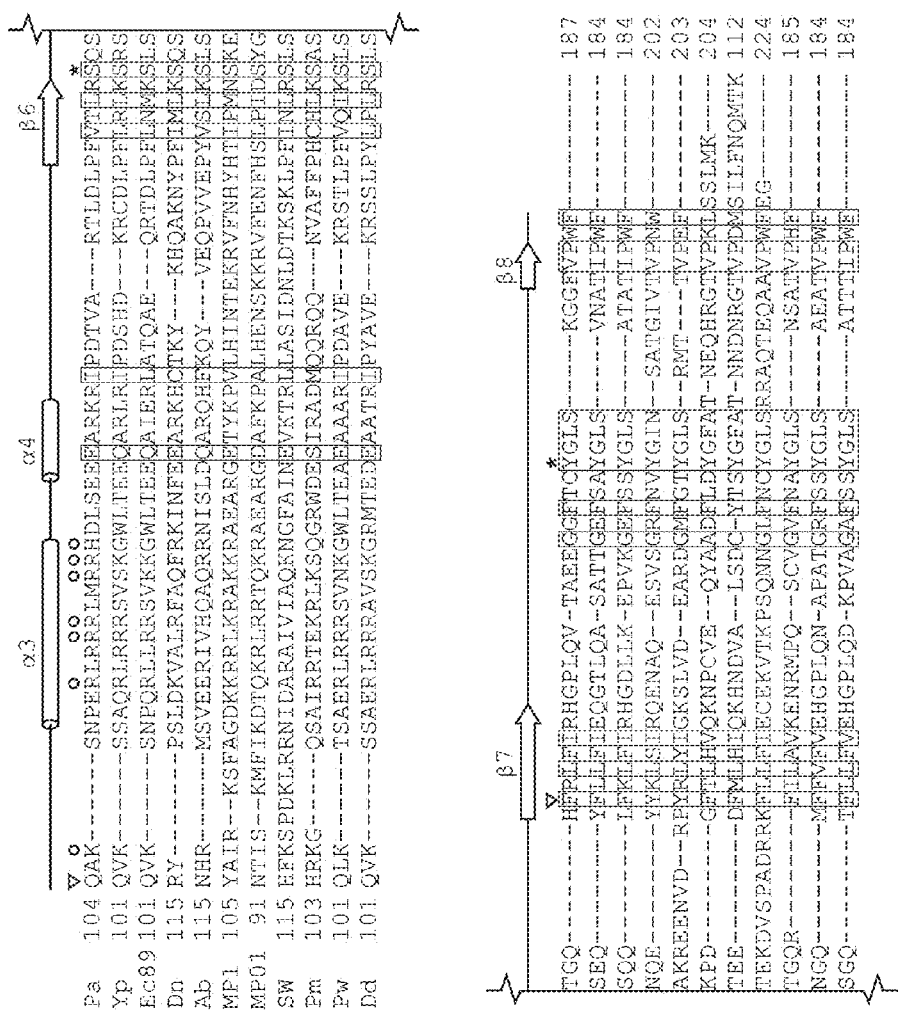

Endoribonucleases that are suitable for use in a subject detection method include endoribonucleases that bind to and cleave a substrate polyribonucleotide in a sequence-specific manner include enzymatically active polypeptides and that differ from an amino acid sequence set forth in any one of FIGS. 4, 5, and/or 11 by from 1 to 20 (e.g., 1, 2, 3, 4, 5, 6, 7, 8, 9, 10, 11, 12, 13, 14, 15, 16, 17, 18, 19, or 20) amino acid substitutions and/or insertions and/or deletions.

The target polyribonucleotide to be detected can be present in a sample, e.g., a biological sample such as blood, a blood product (e.g., plasma), urine, cerebrospinal fluid, bronchoalveolar lavage fluid, saliva, a tissue, cells, etc. The target polyribonucleotide can be isolated or purified. The target polyribonucleotide can be a messenger RNA (mRNA), a viral RNA, bacterial RNA, parasite RNA, or other RNA species. Viral RNAs include, but are not limited to, any member of the Flaviviridae, e.g., hepatitis C virus, Dengue virus, Yellow Fever Virus, West Nile Virus, etc.; any member of Retroviridae; an immunodeficiency virus (e.g., human immunodeficiency virus); etc.

The target polyribonucleotide to be detected can be present in a cell of a multicellular organism (or can be obtained from a cell of a multicellular organism).

The target polyribonucleotide to be detected can be present in or obtained from a cell or organism of any of the six kingdoms, e.g., Bacteria (e.g., Eubacteria); Archaebacteria; Protista; Fungi; Plantae; and Animalia. Suitable sources of target polyribonucleotides include plant-like members of the kingdom Protista, including, but not limited to, algae (e.g., green algae, red algae, glaucophytes, cyanobacteria); fungus-like members of Protista, e.g., slime molds, water molds, etc.; animal-like members of Protista, e.g., flagellates (e.g., Euglena), amoeboids (e.g., amoeba), sporozoans (e.g, Apicomplexa, Myxozoa, Microsporidia), and ciliates (e.g., Paramecium). Suitable sources of target polyribonucleotides include members of the kingdom Fungi, including, but not limited to, members of any of the phyla: Basidiomycota (club fungi; e.g., members of *Agaricus, Amanita, Boletus, Cantherellus*, etc.); Ascomycota (sac fungi, including, e.g., *Saccharomyces*); Mycophycophyta (lichens); Zygomycota (conjugation fungi); and Deuteromycota. Suitable sources of target polyribonucleotides include members of the kingdom Plantae, including, but not limited to, members of any of the following divisions: Bryophyta (e.g., mosses), Anthocerotophyta (e.g., hornworts), Hepaticophyta (e.g., liverworts), Lycophyta (e.g., club mosses), Sphenophyta (e.g., horsetails), Psilophyta (e.g., whisk ferns), Ophioglossophyta, Pterophyta (e.g., ferns), Cycadophyta, Gingkophyta, Pinophyta, Gnetophyta, and Magnoliophyta (e.g., flowering plants). Suitable sources of target polyribonucleotides include members of the kingdom Animalia, including, but not limited to, members of any of the following phyla: Porifera (sponges); Placozoa; Orthonectida (parasites of marine invertebrates); Rhombozoa; Cnidaria (corals, anemones, jellyfish, sea pens, sea pansies, sea wasps); Ctenophora (comb jellies); Platyhelminthes (flatworms); Nemertina (ribbon worms); Ngathostomulida (jawed worms); Gastrotricha; Rotifera; Priapulida; Kinorhyncha; Loricifera; Acanthocephala; Entoprocta; Nemotoda; Nematomorpha; Cycliophora; Mollusca (mollusks); Sipuncula (peanut worms); Annelida (segmented worms); Tardigrada (water bears); Onychophora (velvet worms); Arthropoda (including the subphyla: Chelicerata, Myriapoda, Hexapoda, and Crustacea, where the Chelicerata include, e.g., arachnids, Merostomata, and Pycnogonida, where the Myriapoda include, e.g., Chilopoda (centipedes), Diplopoda (millipedes), Paropoda, and Symphyla, where the Hexapoda include insects, and where the Crustacea include shrimp, hill, barnacles, etc.; Phoronida; Ectoprocta (moss animals); Brachiopoda; Echinodermata (e.g. starfish, sea daisies, feather stars, sea urchins, sea cucumbers, brittle stars, brittle baskets, etc.); Chaetognatha (arrow worms); Hemichordata (acorn worms); and Chordata. Suitable members of Chordata include any member of the following subphyla: Urochordata (sea squirts; including Ascidiacea, Thaliacea, and Larvacea); Cephalochordata (lancelets); Myxini (hagfish); and Vertebrata, where members of Vertebrata include, e.g., members of Petromyzontida (lampreys), Chondrichthyces (cartilaginous fish), Actinopterygii (ray-finned fish), Actinista (coelocanths), Dipnoi (lungfish), Reptilia (reptiles, e.g., snakes, alligators, crocodiles, lizards, etc.), Aves (birds); and Mammalian (mammals). Suitable plants include any monocotyledon and any dicotyledon.

Thus, e.g., a target polyribonucleotide can be present in or obtained from cells from organisms that include, but are not limited to, a protozoan, a plant, a fungus, an algal cell, a yeast, a reptile, an amphibian, a mammal, a marine microorganism, a marine invertebrate, an arthropod, an isopod, an insect, an arachnid, an archaebacterium, and a eubacterium.

A target polyribonucleotide can be present in or obtained from a non-human embryo, e.g., a *Drosophila* embryo; a zebrafish embryo; a mouse embryo; etc.

A target polyribonucleotide can be present in or obtained from a stem cell, e.g., an in vitro stem cell; a non-human stem cell; etc. Suitable stem cells include embryonic stem cells, adult stem cells, and induced pluripotent stem (iPS) cells.

In some embodiments, target polyribonucleotide will be isolated from a tissue taken from an organism; from a particular cell or group of cells isolated from an organism; etc. For example, where the organism is a plant, the target polyribonucleotide will in some embodiments be isolated from the xylem, the phloem, the cambium layer, leaves, roots, etc. Where the organism is an animal, the target polyribonucleotide will in some embodiments be isolated from a particular tissue (e.g., lung, liver, heart, kidney, brain, spleen, skin, fetal tissue, etc.), or a particular cell type (e.g., neuronal cells, epithelial cells, endothelial cells, astrocytes, macrophages, glial cells, islet cells, T lymphocytes, B lymphocytes, etc.).

Methods of Regulating Production of a Target RNA

The present disclosure provides a method of regulating production of a target RNA in a cell. The method generally involves contacting a genetically modified host cell with an agent that activates an inducible promoter, where the genetically modified host cell is genetically modified with a recombinant expression vector comprising a nucleotide sequence encoding an enzyme that catalyzes cleavage at a sequence-specific cleavage site in a substrate polyribonucleotide, where the enzyme-encoding nucleotide sequence is operably linked to the inducible promoter, and where, upon activation of the inducible promoter, the enzyme is produced in the cell and cleaves said target RNA from a precursor RNA.

Figure 10:
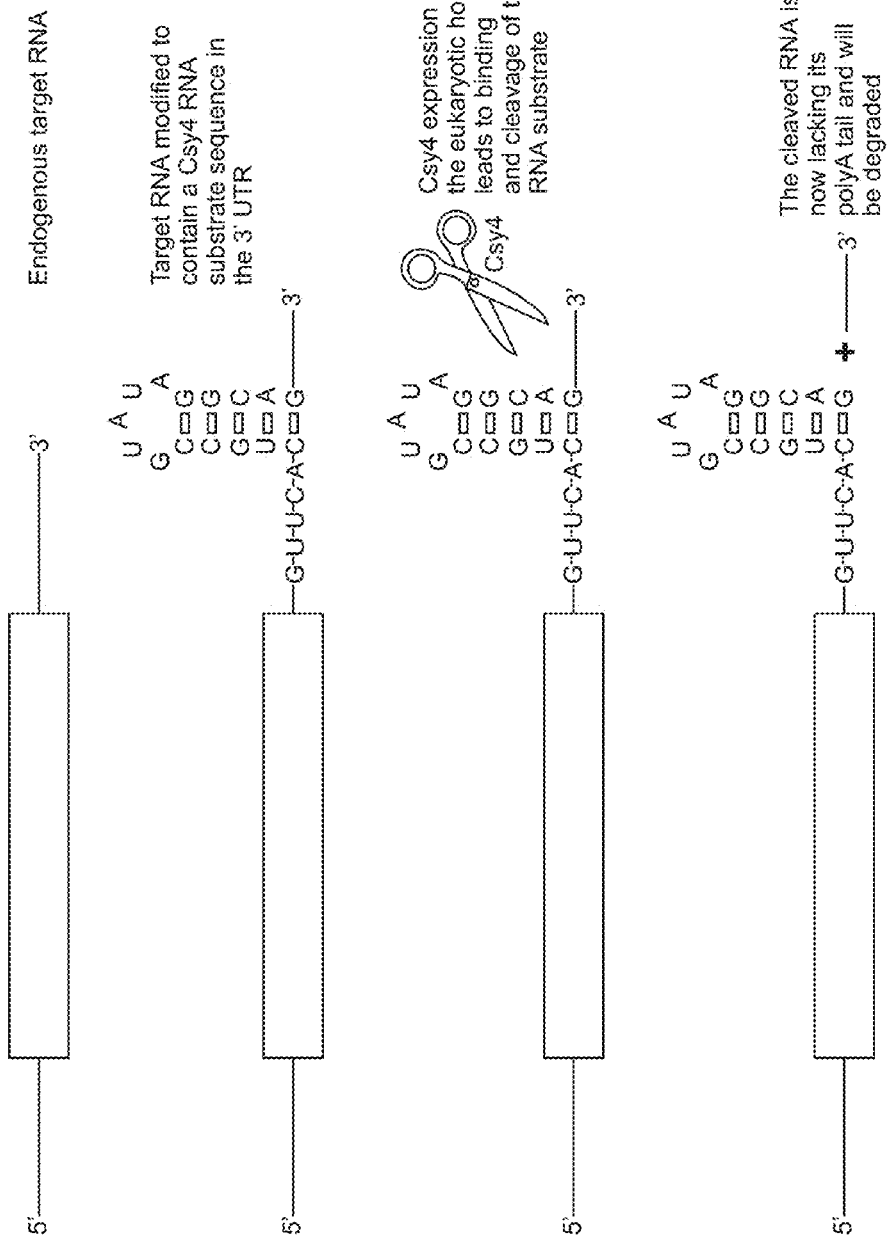
FIG. 10 depicts an exemplary method of regulating expression of a target RNA in a eukaryotic cell. A Csy4 RNA substrate sequence (SEQ ID NO:103) is shown.
Figure 12A:
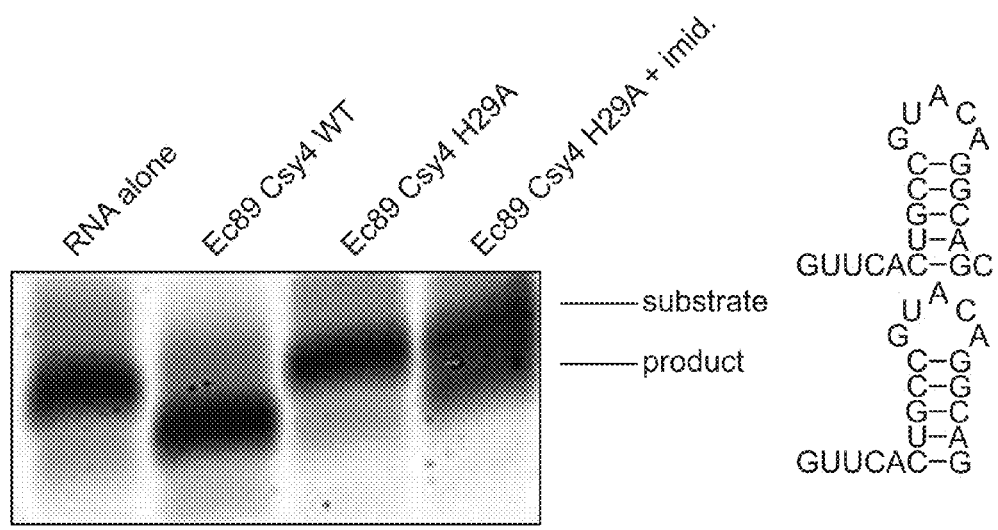
FIGS. 12A-12E illustrate that imidazole can restore cleavage activity to a variety of Csy4 enzymes comprising histidine to alanine active site mutations.
Figure 12B:
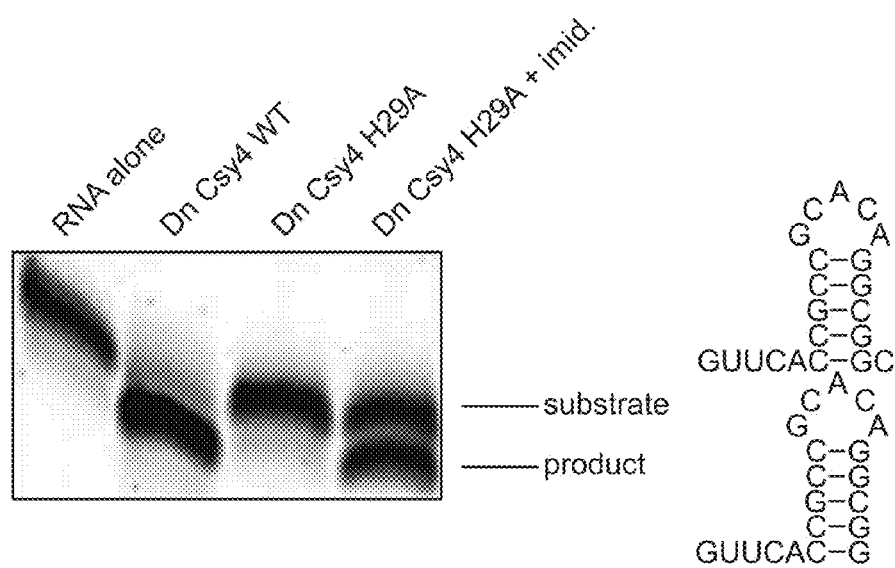
Figure 12C:
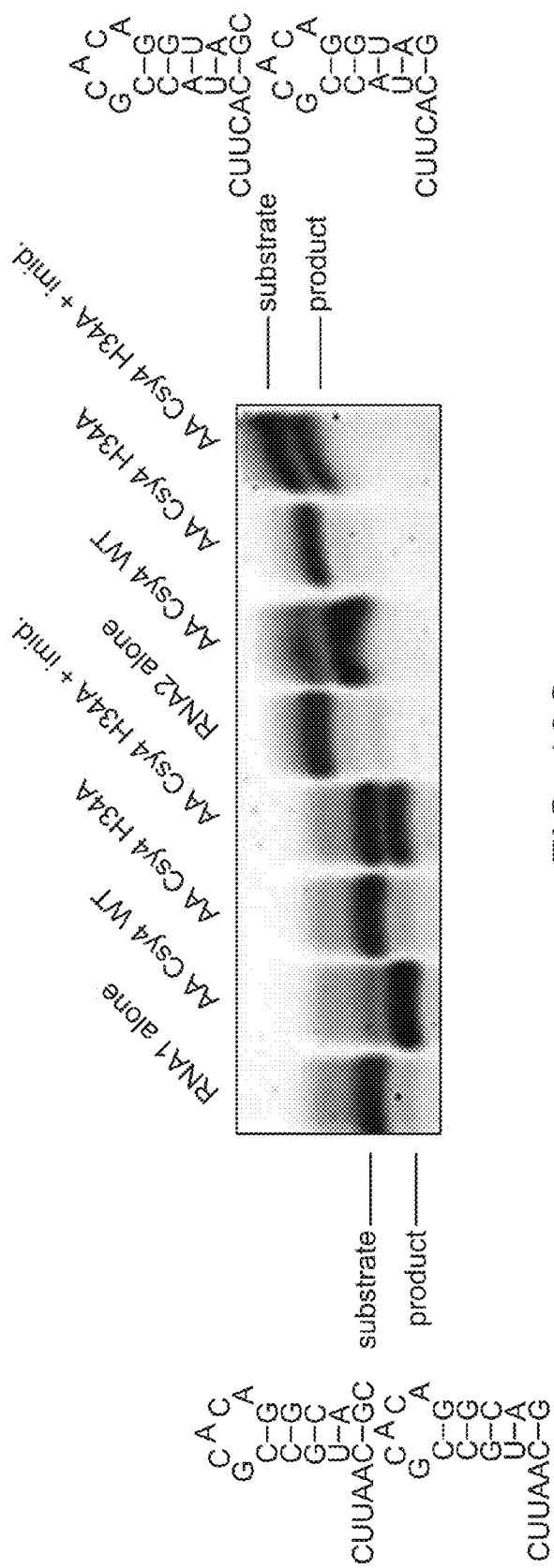
Figure 12D:
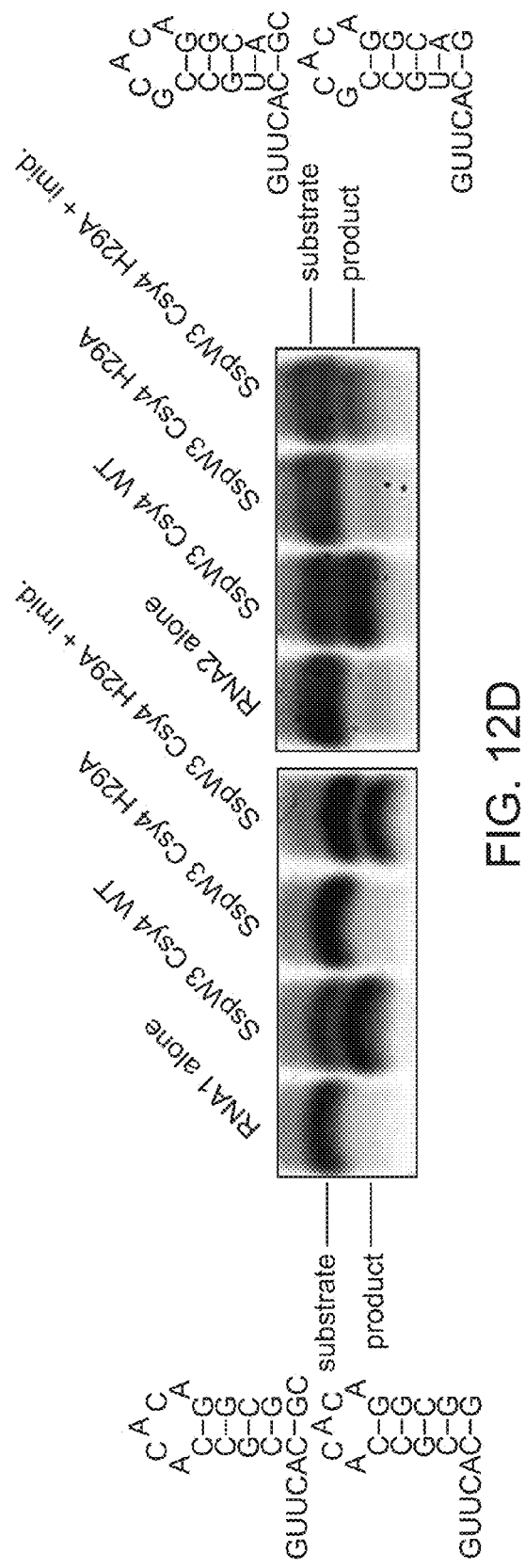
Figure 12E:
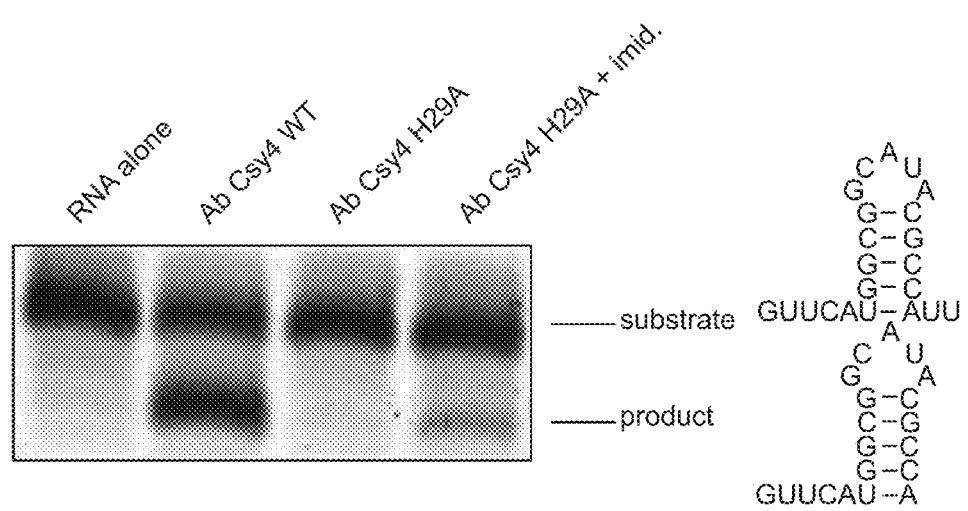

FIG. 10 provides a schematic depiction of an exemplary method of regulating production of a target RNA. In FIG. 10, an endogenous target RNA is modified to include a Csy4 RNA substrate (e.g., GUUCACUGCCGUAUAGGCAG (SEQ ID NO:103); or SEQ ID NO:1) in the 3' untranslated region (3' UTR). Cys4 expression in the host cell leads to binding and cleavage of the RNA substrate. The cleaved RNA now lacks its polyA tail and will be degraded.

For example, in some embodiments, the present disclosure provides a method of regulating production of a target RNA in a eukaryotic cell, where the method involves contacting a genetically modified host cell with an agent that activates an inducible promoter, where the genetically modified host cell is genetically modified with a recombinant expression vector comprising a nucleotide sequence encoding an enzymatically active sequence-specific Csy4 endoribonuclease that catalyzes cleavage at a sequence-specific cleavage site in a substrate polyribonucleotide, where the enzyme-encoding nucleotide sequence is operably linked to the inducible promoter, and where, upon activation of the inducible promoter, the enzyme is produced in the cell and cleaves said target RNA from a precursor RNA. In some cases, the target RNA species is a regulatory RNA. In some cases, cleavage of said target RNA from a precursor RNA inactivates the precursor RNA.

A suitable sequence-specific endoribonuclease is an enzymatically active, sequence-specific endoribonuclease. Endoribonucleases that are suitable for use in a subject method of regulating production of a target RNA include endoribonucleases that bind to and cleave a substrate polyribonucleotide in a sequence-specific manner include enzymatically active polypeptides and that have at least about 85%, at least about 90%, at least about 95%, at least about 98%, at least about 99%, or 100%, amino acid sequence identity to an amino acid sequence set forth in FIG. 4 (Csy4 amino acid sequences).

Endoribonucleases that are suitable for use in a subject method of regulating production of a target RNA include endoribonucleases that bind to and cleave a substrate polyribonucleotide in a sequence-specific manner include enzymatically active polypeptides and that have at least about 85%, at least about 90%, at least about 95%, at least about 98%, at least about 99%, or 100%, amino acid sequence identity to an amino acid sequence set forth in FIG. 5 or FIG. 11 (SEQ ID NO: 39, 79, 84, 90, 104, 108, or 110) (Csy4 amino acid sequences). FIG. 5 and FIG. 11 provide sequences specifically bound by the various endoribonucleases.

Endoribonucleases that are suitable for use in a subject method of regulating production of a target RNA include endoribonucleases that bind to and cleave a substrate polyribonucleotide in a sequence-specific manner include enzymatically active polypeptides and that differ from an amino acid sequence set forth in any one of FIGS. 4, 5, and/or 11 by from 1 to 20 (e.g., 1, 2, 3, 4, 5, 6, 7, 8, 9, 10, 11, 12, 13, 14, 15, 16, 17, 18, 19, or 20) amino acid substitutions and/or insertions and/or deletions.

A suitable inducible promoter can include a promoter that is functional in a eukaryotic cell. Suitable inducible promoters are known in the art. For example, suitable inducible promoters include, but are not limited to, a GAL1 promoter, a GAL10 promoter, an ADH2 promoter, a PHO5 promoter, a CUP1 promoter, a GAL7 promoter, a MET25 promoter, a MET3 promoter, a CYC1 promoter, a HIS3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1. Suitable inducible promoters include tetracycline-inducible promoters; a metallothionein promoter; tetracycline-inducible promoters, methionine-inducible promoters; and galactose-inducible promoters, which promoters are all well known in the art. Other suitable promoters include the ADH2 alcohol dehydrogenase promoter (repressed in glucose, induced when glucose is exhausted and ethanol is made) and the CUP1 metallothionein promoter (induced in the presence of $Cu^{2+}$, $Zn^{2+}$).

Agents that induce any given inducible promoter are known in art. For example, tetracycline-regulatable promoters can be regulated by tetracycline or doxycycline; carbohydrates can be used to induce a carbohydrate-inducible promoter (e.g., galactose for a galactose-inducible promoter); methionine can be used to induce a methionine-inducible promoter; metals can be used to induce a metallothionein promoter.

The target RNA can be a regulatory RNA. Regulator RNAs are well known in the art and include, e.g., microRNAs, short hairpin RNAs (shRNAs), and the like.

In some embodiments, cleavage of the target RNA from a precursor RNA inactivates the precursor RNA.

The genetically modified host cell can be an in vitro cell, e.g., a prokaryotic cell, or a eukaryotic cell (e.g., a mammalian cell, including primary cells, transformed cell lines, and the like). The genetically modified host cell can be an in vivo cell. In some embodiments, the in vivo cell is a non-human cell.

The genetically modified host cell can be a cell of a multicellular organism (or can be obtained from a cell of a multicellular organism).

The genetically modified host cell can be a cell obtained from or present in an organism of any of the six kingdoms, e.g., Bacteria (e.g., Eubacteria); Archaebacteria; Protista; Fungi; Plantae; and Animalia. Suitable organisms include plant-like members of the kingdom Protista, including, but not limited to, algae (e.g., green algae, red algae, glaucophytes, cyanobacteria); fungus-like members of Protista, e.g., slime molds, water molds, etc.; animal-like members of Protista, e.g., flagellates (e.g., Euglena), amoeboids (e.g., amoeba), sporozoans (e.g, Apicomplexa, Myxozoa, Microsporidia), and ciliates (e.g., Paramecium). Suitable organisms include members of the kingdom Fungi, including, but not limited to, members of any of the phyla: Basidiomycota (club fungi; e.g., members of *Agaricus, Amanita, Boletus, Cantherellus*, etc.); Ascomycota (sac fungi, including, e.g., *Saccharomyces*); Mycophycophyta (lichens); Zygomycota (conjugation fungi); and Deuteromycota. Suitable organisms include members of the kingdom Plantae, including, but not limited to, members of any of the following divisions: Bryophyta (e.g., mosses), Anthocerotophyta (e.g., hornworts), Hepaticophyta (e.g., liverworts), Lycophyta (e.g., club mosses), Sphenophyta (e.g., horsetails), Psilophyta (e.g., whisk ferns), Ophioglossophyta, Pterophyta (e.g., ferns), Cycadophyta, Gingkophyta, Pinophyta, Gnetophyta, and Magnoliophyta (e.g., flowering plants). Suitable organisms include members of the kingdom Animalia, including, but not limited to, members of any of the following phyla: Porifera (sponges); Placozoa; Orthonectida (parasites of marine invertebrates); Rhombozoa; Cnidaria (corals, anemones, jellyfish, sea pens, sea pansies, sea wasps); Ctenophora (comb jellies); Platyhelminthes (flatworms); Nemertina (ribbon worms); Ngathostomulida (jawed worms); Gastrotricha; Rotifera; Priapulida; Kinorhyncha; Loricifera; Acanthocephala; Entoprocta; Nemotoda; Nematomorpha; Cyclophora; Mollusca (mollusks); Sipuncula (peanut worms); Annelida (segmented worms); Tardigrada (water bears); Onychophora (velvet worms); Arthropoda (including the subphyla: Chelicerata, Myriapoda, Hexapoda, and Crustacea, where the Chelicerata include, e.g., arachnids, Merostomata, and Pycnogonida, where the Myriapoda include, e.g., Chilopoda (centipedes), Diplopoda (millipedes), Paropoda, and Symphyla, where the Hexapoda include insects, and where the Crustacea include shrimp, krill, barnacles, etc.; Phoronida; Ectoprocta (moss animals); Brachiopoda; Echinodermata (e.g. starfish, sea daisies, feather stars, sea urchins, sea cucumbers, brittle stars, brittle baskets, etc.); Chaetognatha (arrow worms); Hemichordata (acorn worms); and Chordata. Suitable members of Chordata include any member of the following subphyla: Urochordata (sea squirts; including Ascidiacea, Thaliacea, and Larvacea); Cephalochordata (lancelets); Myxini (hagfish); and Vertebrata, where members of Vertebrata include, e.g., members of Petromyzontida (lampreys), Chondrichthyces (cartilaginous fish), Actinopterygii (ray-finned fish), Actinista (coelocanths), Dipnoi (lungfish), Reptilia (reptiles, e.g., snakes, alligators, crocodiles, lizards, etc.), Aves (birds); and Mammalian (mammals). Suitable plants include any monocotyledon and any dicotyledon.

Thus, e.g., a genetically modified host cell can be a cell obtained from or present in a protozoan, a plant, a fungus, an algal cell, a yeast, a reptile, an amphibian, a mammal, a marine microorganism, a marine invertebrate, an arthropod, an isopod, an insect, an arachnid, an archaebacterium, and a eubacterium.

Suitable mammalian cells include primary cells and immortalized cell lines. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like.

The genetically modified host cell can be a cell obtained from or present in a non-human embryo, e.g., a *Drosophila* embryo; a zebrafish embryo; a mouse embryo; etc.

The genetically modified host cell can be a stem cell, e.g., an in vitro stem cell; a non-human stem cell; etc. Suitable stem cells include embryonic stem cells, adult stem cells, and induced pluripotent stem (iPS) cells.

Methods of Isolating a Target Nucleic Acid

Figure 9:
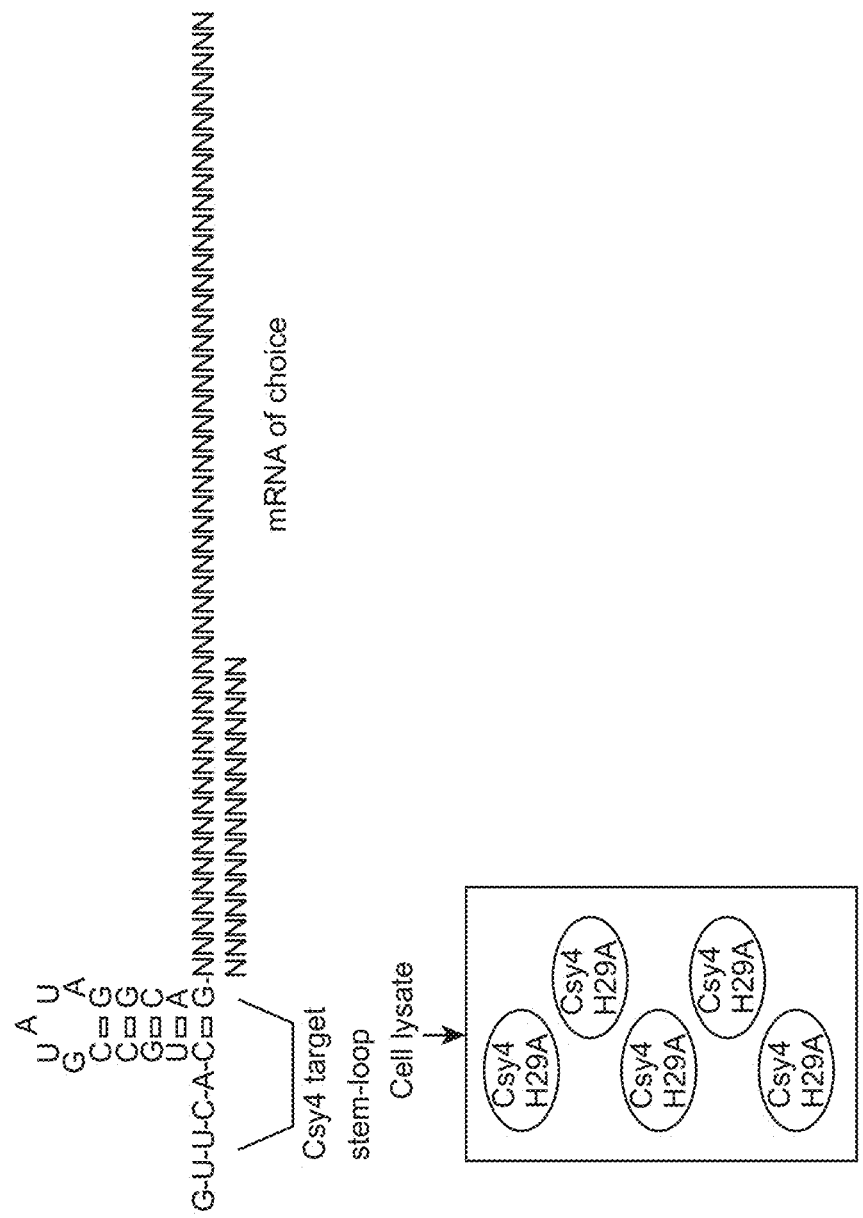
FIG. 9 depicts an exemplary method of isolating a target RNA. A Csy4 target stem-loop (SEQ ID NO:103) is shown.
Figure 9:
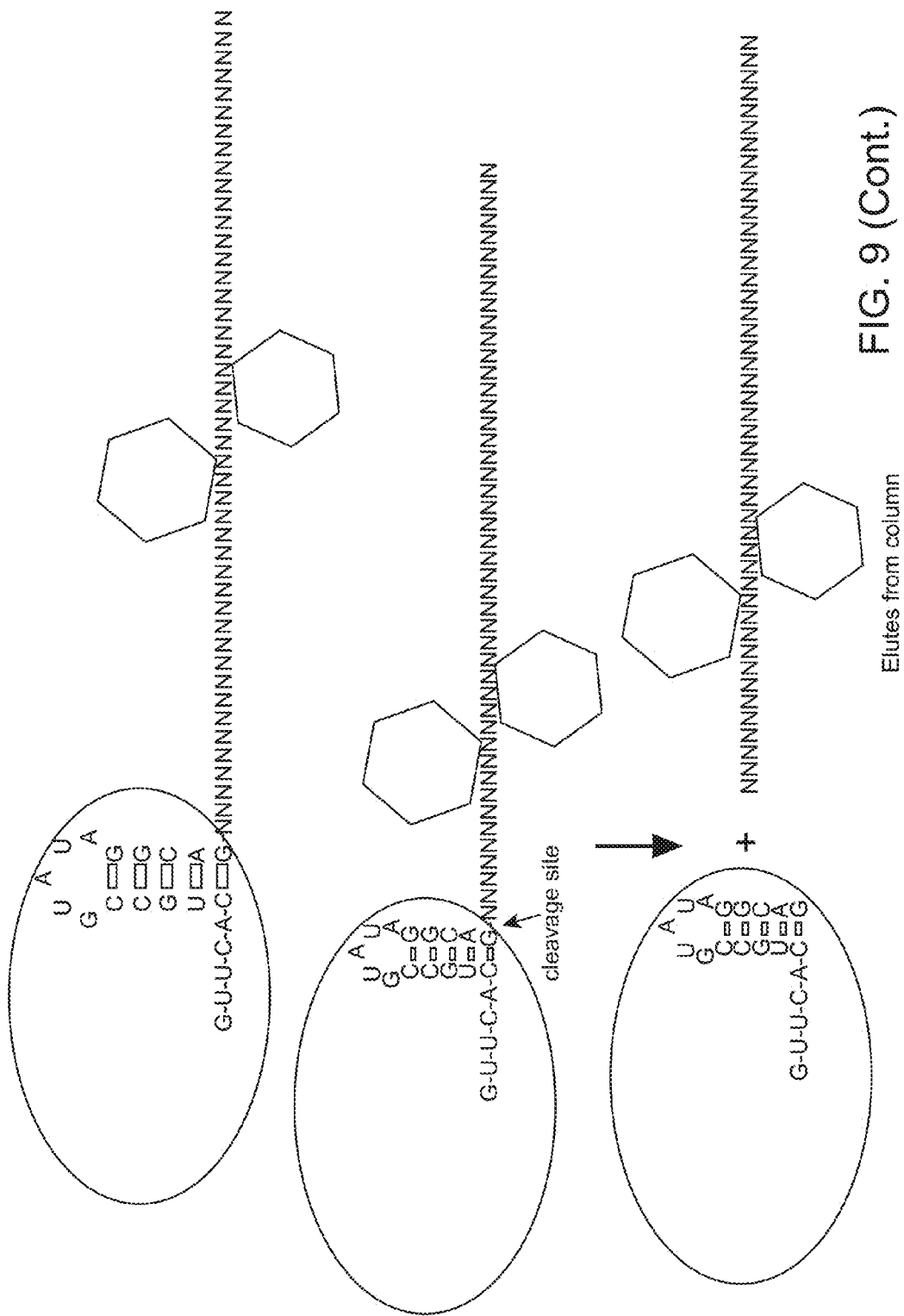

The present disclosure provides methods of isolating a target nucleic acid from a mixed population of nucleic acids. The methods generally involve: a) contacting a mixed population of nucleic acids with an immobilized sequence-specific, enzymatically inactive endoribonuclease, wherein the mixed population of nucleic acids includes a target nucleic acid comprising a "tag" (or "recognition") nucleotide sequence that is specifically bound by the immobilized sequence-specific, enzymatically inactive endoribonuclease, such that the target nucleic acid comprising the tag nucleotide sequence ("tagged target nucleic acid") binds to the immobilized sequence-specific, enzymatically inactive endoribonuclease, forming a tagged target nucleic acid/immobilized sequence-specific enzymatically active endoribonuclease complex, wherein the contacting step takes place in a liquid solution (a "binding solution"); and b) adding imidazole to the liquid solution to a final concentration of from about 100 mM to about 500 mM (e.g., from about 100 mM to about 150 mM, from about 150 mM to about 200 mM, from about 200 mM to about 250 mM, from about 250 mM to about 300 mM, from about 300 mM to about 350 mM, from about 350 mM to about 400 mM, from about 400 mM to about 450 mM, or from about 450 mM to about 500 mM), thereby forming a reactivation solution that enzymatically reactivates the enzymatically inactive endoribonuclease such that the endoribonuclease becomes enzymatically active and cleaves the target nucleic acid from the "tag" nucleotide sequence, thereby releasing the target nucleic acid. FIG. 9 is a schematic representation of an exemplary embodiment of a subject method for isolating a target RNA.

The method can further include one or more washing steps. For example, after step (a) and before step (b), the immobilized sequence-specific, enzymatically inactive endoribonuclease that comprises a bound target nucleic acid comprising a "tag" nucleotide sequence can be washed one or more times with the binding solution, such that the target nucleic acid remains bound to the sequence-specific, enzymatically inactive endoribonuclease, and any unbound nucleic acids are washed away.

The mixed population of nucleic acids can include RNA and DNA. The target nucleic acid is an RNA that comprises a "tag" or "recognition" nucleotide sequence that is specifically bound by the sequence-specific endoribonuclease. In its enzymatically inactive state ("uninduced" state), the endoribonuclease can bind, but cannot cleave, the tagged target RNA. In its enzymatically active state ("induced" state) (e.g., in the presence of imidazole in a concentration of from about 100 mM to about 500 mM), the endoribonuclease can both bind and cleave the recognition nucleotide sequence in the tagged target nucleic acid, thereby releasing the target nucleic acid from the tag.

The binding solution can include a buffer and a salt; and lacks imidazole. The reactivation solution can include imidazole in a final concentration of from about 100 mM to about 500 mM, e.g., from about 100 mM to about 150 mM, from about 150 mM to about 200 mM, from about 250 mM to about 350 mM, from about 350 mM to about 400 mM, or from about 400 mM to about 500 mM. The presence of imidazole reactivates the sequence-specific, enzymatically inactive endoribonuclease such that the endoribonuclease becomes enzymatically active, e.g., the endoribonuclease exhibits at least about 50%, at least about 60%, at least about 70%, at least about 80%, at least about 90%, at least about 95%, or more than 95%, of wild-type sequence-specific endoribonuclease (e.g., an amino acid sequence as depicted in FIG. 5 (e.g., SEQ ID NO:6, 8, 9, etc.)). As one non-limiting example, the sequence-specific, enzymatically inactive endoribonuclease is an H29A mutant (or corresponding variant: see FIG. 4 and FIG. 11) of Csy4 (as described below; and as depicted in FIG. 6 and FIG. 11 (e.g., SEQ ID NO: 105, 106, 107, 109, 111, 112)). Contacting the Csy4 (H29A) mutant with imidazole, as described above, reactivates the endoribonuclease such that it is capable of cleaving, in a sequence-specific manner, a recognition sequence in a target ribonucleic acid. Also suitable for use is an H29A, S50C double mutant of Csy4 (as described below). In some embodiments, the "tag" or recognition sequence comprises the nucleotide sequence 5'-GUUCACUGCCGUAUAGGCAGCUAAGAAA-3' (SEQ ID NO:1) or any of the recognition sequences depicted in FIG. 5 or FIG. 11.

The "tag" or "recognition" nucleotide sequence can be introduced into a nucleic acid using standard recombinant methods. Thus, the tagged target nucleic acid will include a tag that is enzymatically cleaved, thereby releasing the target nucleic acid.

In some embodiments, the tagged target nucleic acid (RNA) will have one or more polypeptides bound thereto. A tagged target RNA that has one or more polypeptides bound thereto is referred to herein as a RNA protein complex. Thus, in some embodiments, the target RNA that is isolated using a subject method is an RNA protein complex. In some embodiments, a subject method can further comprise analyzing the polypeptide(s) bound to the isolated target RNA.

A subject method provides for isolation of a target RNA (or RNA protein complex). In some embodiments, a subject method provides for purification of a target RNA (or RNA protein complex) such that the target RNA (or RNA protein complex) is at least about 50% pure, at least about 60% pure, at least about 70% pure, at least about 80% pure, at least about 90% pure, at least about 95% pure, at least about 98% pure, or greater than 98% pure.

In some embodiments, a protein bound to a target RNA in a target RNA/protein complex can be eluted from the RNA/protein complex. The eluted protein can be further characterized, e.g., by sequencing, enzymatic digestion, a functional assay, etc.

The mixed population of nucleic acids can be present in a cell lysate. For example, an expression vector comprising a nucleotide sequence encoding a tagged target RNA is introduced into a cell (e.g., in vitro or in vivo), such that the cell synthesizes the tagged target RNA. A lysate is made from the cell and the lysate (optionally subjected to one or more steps to enrich for nucleic acids) is applied to the immobilized sequence-specific enzymatically-inactive endoribonuclease.

The sequence-specific enzymatically-inactive endoribonuclease can be immobilized on any of a variety of insoluble support. Suitable insoluble supports include, but are not limited to agarose beads, magnetic beads, a test strip, a multi-well dish, and the like. The insoluble support can comprise a variety of substances (glass, polystyrene, polyvinyl chloride, polyvinyl chloride, polypropylene, polyethylene, polycarbonate, dextran, nylon, amylose, natural and modified celluloses, polyacrylamides, agaroses, and magnetite) and can be provided in a variety of forms, including, e.g., agarose beads, polystyrene beads, latex beads, magnetic beads, colloid metal particles, glass and/or silicon chips and surfaces, nitrocellulose strips, nylon membranes, sheets, wells of reaction trays (e.g., multi-well plates), plastic tubes, etc.

The present disclosure also provides a method of isolating a polypeptide that binds a target RNA, where the method comprises: a) contacting an immobilized complex with a liquid solution comprising a polypeptide that binds the target RNA, where the immobilized complex comprises the variant Csy4 endoribonuclease and a tagged target RNA comprising a recognition nucleotide sequence that is specifically bound by the variant Csy4 endoribonuclease, where said contacting results in binding of the polypeptide to the target RNA, where said contacting is carried out in a binding solution lacking imidazole; and b) eluting the bound polypeptide.

Endoribonucleases

The present disclosure provides a sequence-specific endoribonuclease. In some embodiments, the present disclosure provides a sequence-specific endoribonuclease that binds to a recognition sequence in a target polyribonucleotide, but that does not cleave the target polyribonucleotide, i.e., the sequence-specific endoribonuclease is enzymatically inactive in hydrolyzing the target polyribonucleotide. In some embodiments, the present disclosure provides a sequence-specific endoribonuclease that binds to a recognition sequence in a target polyribonucleotide, and cleaves the target polyribonucleotide within or near the recognition sequence, i.e., the sequence-specific endoribonuclease is enzymatically active in hydrolyzing the target polyribonucleotide.

In some embodiments, a subject sequence-specific endoribonuclease is immobilized on an insoluble substrate. Suitable insoluble substrates include, but are not limited to agarose beads, magnetic beads, a test strip, a multi-well dish, and the like. The insoluble substrate can comprise a variety of substances (glass, polystyrene, polyvinyl chloride, polypropylene, polyethylene, polycarbonate, dextran, nylon, amylose, natural and modified celluloses, polyacrylamides, agaroses, and magnetite) and can be provided in a variety of forms, including, e.g., agarose beads, polystyrene beads, latex beads, magnetic beads, colloid metal particles, glass and/or silicon chips and surfaces, nitrocellulose strips, nylon membranes, sheets, wells of reaction trays (e.g., multi-well plates), plastic tubes, etc.

Enzymatically Inactive Sequence-Specific Endoribonuclease

The present disclosure provides an enzymatically inactive, sequence-specific endoribonuclease, wherein the enzymatically inactive sequence-specific endoribonuclease binds to a target sequence in a polyribonucleotide in a sequence-specific manner. A subject enzymatically inactive, sequence-specific endoribonuclease binds a target polyribonucleotide in a sequence-specific manner, but does not cleave the target polyribonucleotide. A subject enzymatically inactive, sequence-specific endoribonuclease is useful for isolating a target RNA from a mixed population of nucleic acids, as described above.

In some embodiments, a subject enzymatically inactive, sequence-specific endoribonuclease comprises one or more amino acid substitutions compared to a naturally-occurring, enzymatically active, Csy4, CasE, or Cas6 polypeptide.

In some embodiments, a subject enzymatically inactive, sequence-specific endoribonuclease comprises an amino acid substitution at His-29 of a Csy4 polypeptide, or at an equivalent position in a CasE or a Cas6 polypeptide. In some embodiments, a subject enzymatically inactive, sequence-specific endoribonuclease comprises an amino acid substitution at Ser-148 of a Csy4 polypeptide, or at an equivalent position in a CasE or a Cas6 polypeptide.

FIG. 6 (SEQ ID NO: 101, 102) and FIG. 11 (SEQ ID NO: 105, 106, 107, 109, 111, 112) depict non-limiting examples of suitable enzymatically inactive, sequence-specific endoribonuclease amino acid sequences. In some embodiments, a subject enzymatically inactive, sequence-specific endoribonuclease comprises an amino acid sequence having at least about 75%, at least about 80%, at least about 85%, at least about 90%, at least about 95%, at least about 98%, at least about 99%, or 100%, amino acid sequence identity with an amino acid sequence depicted in FIG. 6 (SEQ ID NO: 101, 102) or FIG. 11 (SEQ ID NO: 105, 106, 107, 109, 111, 112), where the amino acid sequence includes a substitution at His-29, Ser-50, or both His-29 and Ser-50. For example, the variant Csy4 endoribonuclease can include a H29A (His-29 to Ala-29) substitution (or a corresponding His to Ala variant according to sequence alignment, e.g., FIG. 4, such as H34A, His-34 to Ala-34, in SEQ ID NO: 108, 109 (see FIG. 11D)), a S50C (Ser-50 to Cys-50) substitution, or both a H29A and a S50C substitution.

In some embodiments, a subject enzymatically inactive, sequence-specific endoribonuclease is a variant Csy4 endoribonuclease. In some cases, a subject variant Csy4 endoribonuclease comprises an amino acid sequence having at least about 95% amino acid sequence identity to the amino acid sequence set forth in FIG. 6, where the endoribonuclease comprises an amino acid substitution at His-29, where the variant Csy4 endoribonuclease is enzymatically inactive in the absence of imidazole, and where the variant Csy4 endoribonuclease is activatable in the presence of imidazole. In some instances, the amino acid substitution is a His29 to Ala29 substitution. In some cases, variant Csy4 endoribonuclease also includes a Ser-50 substitution. In some instances, a subject variant Csy4 endoribonuclease binds an RNA substrate that comprises the nucleotide sequence 5'-GUUCACUGCCGUAUAGGCAGC-UAAGAAA-3' (SEQ ID NO:1) or any of the recognition sequences depicted in FIG. 5 or FIG. 11.

A subject enzymatically inactive, sequence-specific endoribonuclease is "conditionally" enzymatically inactive, e.g., a subject enzymatically inactive, sequence-specific endoribonuclease (e.g., a subject variant Csy4 endoribonuclease) is enzymatically inactive in the absence of imidazole; and the enzymatically inactive, sequence-specific endoribonuclease (e.g., subject variant Csy4 endoribonuclease) is activatable by imidazole. For example, the enzymatically inactive, sequence-specific endoribonuclease (e.g., subject variant Csy4 endoribonuclease) can be enzymatically activated by contacting the endoribonuclease with imidazole at a concentration of from about 100 mM to about 500 mM.

The presence of imidazole (e.g., in a concentration range of from about 100 mM to about 500 mM) reactivates the sequence-specific, enzymatically inactive endoribonuclease such that the endoribonuclease becomes enzymatically active, e.g., the endoribonuclease exhibits at least about 50%, at least about 60%, at least about 70%, at least about 80%, at least about 90%, at least about 95%, or more than 95%, of wild-type sequence-specific endoribonuclease (e.g., an amino acid sequence as depicted in FIG. 5 (e.g., SEQ ID NO:6, 8, or 9) or FIG. 11 (SEQ ID NO: 39, 79, 84, 90, 104, 108, or 110)).

In some embodiments, a subject enzymatically inactive, sequence-specific endoribonuclease (e.g., a subject variant Csy4 endoribonuclease) comprises a detectable label, including a moiety that provides a detectable signal. Suitable detectable labels and/or moieties that provide a detectable signal include, but are not limited to, an enzyme, a radioisotope, a member of a FRET pair, a member of a specific binding pair; a fluorophore; a fluorescent protein; a quantum dot; and the like.

FRET pairs (donor/acceptor) suitable for use include, but are not limited to, EDANS/fluorescein, IAEDANS/fluorescein, fluorescein/tetramethylrhodamine, fluorescein/Cy 5, IEDANS/DABCYL, fluorescein/QSY-7, fluorescein/LC Red 640, fluorescein/Cy 5.5 and fluorescein/LC Red 705. In addition, a fluorophore/quantum dot donor/acceptor pair can be used.

Suitable fluorophores ("fluorescent label") include any molecule that may be detected via its inherent fluorescent properties, which include fluorescence detectable upon excitation. Suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, Texas Red, IAEDANS, EDANS, BODIPY FL, LC Red 640, Cy 5, Cy 5.5, LC Red 705 and Oregon green. Suitable optical dyes are described in the 2002 Molecular Probes Handbook, 9th Ed., by Richard P. Haugland, hereby expressly incorporated by reference.

Suitable enzymes include, but are not limited to, horse radish peroxidase, luciferase, β-galactosidase, and the like.

Suitable fluorescent proteins include, but are not limited to, a green fluorescent protein (GFP), e.g., a GFP from *Aequoria victoria* or a mutant or derivative thereof e.g., as described in U.S. Pat. Nos. 6,066,476; 6,020,192; 5,985, 577; 5,976,796; 5,968,750; 5,968,738; 5,958,713; 5,919, 445; 5,874,304; a red fluorescent protein; a yellow fluorescent protein; any of a variety of fluorescent and colored proteins from *Anthozoan* species, as described in, e.g., Matz et al. (1999) *Nature Biotechnol.* 17:969-973; and the like.

Suitable nanoparticles include, e.g., quantum dots (QDs), fluorescent or luminescent nanoparticles, and magnetic nanoparticles. Any optical or magnetic property or characteristic of the nanoparticle(s) can be detected.

QDs and methods for their synthesis are well known in the art (see, e.g., U.S. Pat. Nos. 6,322,901; 6,576,291; and 6,815,064). QDs can be rendered water soluble by applying coating layers comprising a variety of different materials (see, e.g., U.S. Pat. Nos. 6,423,551; 6,251,303; 6,319,426; 6,426,513; 6,444,143; and 6,649,138). For example, QDs can be solubilized using amphiphilic polymers. Exemplary polymers that have been employed include octylamine-modified low molecular weight polyacrylic acid, polyethylene-glycol (PEG)-derivatized phospholipids, polyanhydrides, block copolymers, etc. QDs can be conjugated to a polypeptide via any of a number of different functional groups or linking agents that can be directly or indirectly linked to a coating layer (see, e.g., U.S. Pat. Nos. 5,990,479; 6,207,392; 6,251,303; 6,306,610; 6,325,144; and 6,423, 551).

QDs with a wide variety of absorption and emission spectra are commercially available, e.g., from Quantum Dot Corp. (Hayward Calif.; now owned by Invitrogen) or from Evident Technologies (Troy, N.Y.). For example, QDs having peak emission wavelengths of approximately 525, 535, 545, 565, 585, 605, 655, 705, and 800 nm are available. Thus the QDs can have a range of different colors across the visible portion of the spectrum and in some cases even beyond.

Suitable radioisotopes include, but are not limited to $^{14}C$, $^{3}H$, $^{32}P$, $^{33}P$, $^{35}S$, $^{125}I$, and $^{131}I$. The use of radioisotopes as labels is well known in the art.

In some embodiments, a subject enzymatically inactive, sequence-specific endoribonuclease (e.g., a subject variant Csy4 endoribonuclease) is immobilized on an insoluble substrate. Suitable insoluble substrates include, but are not limited to agarose beads, magnetic beads, a test strip, a multi-well dish, and the like. The insoluble substrate can comprise a variety of substances (glass, polystyrene, polyvinyl chloride, polypropylene, polyethylene, polycarbonate, dextran, nylon, amylose, natural and modified celluloses, polyacrylamides, agaroses, and magnetite) and can be provided in a variety of forms, including, e.g., agarose beads, polystyrene beads, latex beads, magnetic beads, colloid metal particles, glass and/or silicon chips and surfaces, nitrocellulose strips, nylon membranes, sheets, wells of reaction trays (e.g., multi-well plates), plastic tubes, etc.

In some embodiments, a subject enzymatically inactive, sequence-specific endoribonuclease (e.g., a subject variant Csy4 endoribonuclease) is purified, e.g., is at least 80% pure, at least 85% pure, at least 90% pure, at least 95% pure, at least 98% pure, at least 99% pure, or greater than 99% pure.

Compositions

The present disclosure provides compositions comprising a subject sequence-specific, enzymatically inactive, endoribonuclease. A subject composition can comprise, in addition to a subject sequence-specific, enzymatically inactive, endoribonuclease, one or more of: a salt, e.g., NaCl, MgCl, KCl, MgSO$_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a protease inhibitor; and the like.

Enzymatically Active Sequence-Specific Endoribonuclease

In some embodiments, a subject enzymatically active sequence-specific endoribonuclease comprises a moiety that provides for detection. For example, a subject enzymatically active sequence-specific endoribonuclease can comprise a covalently or non-covalently linked moiety that provides for detection.

Suitable detectable labels include any composition detectable by spectroscopic, photochemical, biochemical, immunochemical, electrical, optical or chemical means. Moieties that provide for detection include, but are not limited to, a fluorescent molecule; a quantum dot; an enzyme (other than the endoribonuclease), where the enzyme catalyzes conversion of a substrate to a detectable product, where the product is directly detectable; a nanoparticle; and the like.

Suitable fluorescent proteins that can be linked to a subject enzymatically active sequence-specific endoribonuclease include, but are not limited to, a green fluorescent protein (GFP), e.g., a GFP from *Aequoria victoria* or a mutant or derivative thereof e.g., as described in U.S. Pat. Nos. 6,066,476; 6,020,192; 5,985,577; 5,976,796; 5,968,750; 5,968,738; 5,958,713; 5,919,445; 5,874,304; a red fluorescent protein; a yellow fluorescent protein; any of a variety of fluorescent and colored proteins from *Anthozoan* species, as described in, e.g., Matz et al. (1999) *Nature Biotechnol.* 17:969-973; and the like.

Suitable nanoparticles include, e.g., quantum dots (QDs), fluorescent or luminescent nanoparticles, and magnetic nanoparticles. Any optical or magnetic property or characteristic of the nanoparticle(s) can be detected.

QDs and methods for their synthesis are well known in the art (see, e.g., U.S. Pat. Nos. 6,322,901; 6,576,291; and 6,815,064). QDs can be rendered water soluble by applying coating layers comprising a variety of different materials (see, e.g., U.S. Pat. Nos. 6,423,551; 6,251,303; 6,319,426; 6,426,513; 6,444,143; and 6,649,138). For example, QDs can be solubilized using amphiphilic polymers. Exemplary polymers that have been employed include octylamine-modified low molecular weight polyacrylic acid, polyethylene-glycol (PEG)-derivatized phospholipids, polyanhydrides, block copolymers, etc. QDs can be conjugated to a polypeptide via any of a number of different functional groups or linking agents that can be directly or indirectly linked to a coating layer (see, e.g., U.S. Pat. Nos. 5,990,479; 6,207,392; 6,251,303; 6,306,610; 6,325,144; and 6,423,551).

QDs with a wide variety of absorption and emission spectra are commercially available, e.g., from Quantum Dot Corp. (Hayward Calif.; now owned by Invitrogen) or from Evident Technologies (Troy, N.Y.). For example, QDs having peak emission wavelengths of approximately 525, 535, 545, 565, 585, 605, 655, 705, and 800 nm are available. Thus the QDs can have a range of different colors across the visible portion of the spectrum and in some cases even beyond.

In some embodiments, a subject enzymatically active, sequence-specific endoribonuclease is purified, e.g., is at least 80% pure, at least 85% pure, at least 90% pure, at least 95% pure, at least 98% pure, at least 99% pure, or greater than 99% pure.

Compositions

The present disclosure provides compositions comprising a subject sequence-specific, enzymatically active endoribonuclease. A subject composition can comprise, in addition to a subject sequence-specific enzymatically active, endoribonuclease, one or more of: a salt, e.g., NaCl, MgCl, KCl, MgSO$_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a protease inhibitor; and the like.

The present disclosure provides compositions comprising a subject sequence-specific, enzymatically inactive endoribonuclease (e.g., a subject variant Csy4 endoribonuclease). A subject composition can comprise, in addition to a subject sequence-specific enzymatically inactive endoribonuclease (e.g., a subject variant Csy4 endoribonuclease), one or more of: a salt, e.g., NaCl, MgCl, KCl, MgSO$_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a protease inhibitor; and the like. In some embodiments, the composition lacks imidazole. In some embodiments, the composition comprises imidazole in a concentration of from about 100 mM to about 500 mM.

Methods of Producing a Subject Sequence-Specific Endoribonuclease

A subject sequence-specific endoribonuclease (e.g., a subject sequence-specific enzymatically active, endoribonuclease; a subject sequence-specific enzymatically inactive, endoribonuclease) can be produced by any known method, e.g., conventional synthetic methods for protein synthesis; recombinant DNA methods; etc.

Where a subject sequence-specific endoribonuclease is chemically synthesized, the synthesis may proceed via liquid-phase or solid-phase. Solid phase polypeptide synthesis (SPPS), in which the C-terminal amino acid of the sequence is attached to an insoluble support followed by sequential addition of the remaining amino acids in the sequence, is an example of a suitable method for the chemical synthesis of a subject sequence-specific endoribonuclease. Various forms of SPPS, such as Fmoc and Boc, are available for synthesizing a subject sequence-specific endoribonuclease. Techniques for solid phase synthesis are described by Barany and Merrifield, Solid-Phase Peptide Synthesis; pp. 3-284 in The Peptides: Analysis, Synthesis, Biology. Vol. 2: Special Methods in Peptide Synthesis, Part A., Merrifield, et al. J. Am. Chem. Soc., 85: 2149-2156 (1963); Stewart et al., Solid Phase Peptide Synthesis, 2nd ed. Pierce Chem. Co., Rockford, Ill. (1984); and Ganesan A. 2006 *Mini Rev. Med Chem.* 6:3-10 and Camarero J A et al. 2005 *Protein Pept Lett.* 12:723-8.

Standard recombinant methods can be used for production of a subject sequence-specific endoribonuclease. For example, nucleic acids encoding a subject sequence-specific endoribonuclease are inserted into expression vectors. The DNA segments encoding a subject sequence-specific endoribonuclease are operably linked to control sequences in the expression vector(s) that ensure the expression of the encoded polypeptides. Expression control sequences include, but are not limited to, promoters (e.g., naturally-associated or heterologous promoters), signal sequences, enhancer elements, and transcription termination sequences. The expression control sequences can be eukaryotic promoter systems in vectors capable of transforming or transfecting eukaryotic host cells (e.g., COS or CHO cells). Once the vector has been incorporated into the appropriate host, the host is maintained under conditions suitable for high level expression of the nucleotide sequences, and the collection and purification of the endoribonuclease.

Nucleic Acids and Host Cells

The present disclosure provides a nucleic acid comprising a nucleotide sequence encoding a subject sequence-specific endoribonuclease (e.g., a subject sequence-specific, enzymatically active endoribonuclease; a subject sequence-specific, enzymatically inactive endoribonuclease). In some embodiments, the nucleic acid is an expression vector, where the expression vector can provide for production of the sequence-specific endoribonuclease, e.g., in a cell.

A nucleotide sequence encoding a subject sequence-specific endoribonuclease (e.g., a subject sequence-specific, enzymatically active endoribonuclease; a subject sequence-specific, enzymatically inactive endoribonuclease) can be operably linked to one or more regulatory elements, such as a promoter and enhancer, that allow expression of the nucleotide sequence in the intended target cells (e.g., a cell that is genetically modified to synthesize the encoded endoribonuclease).

In some embodiments, a subject nucleic acid comprises a nucleotide sequence encoding a polypeptide having at least about 75%, at least about 80%, at least about 85%, at least about 90%, at least about 95%, at least about 98%, at least about 99%, or 100%, with an amino acid sequence set forth in FIG. 4, FIG. 5, and/or FIG. 11. In some embodiments, a subject nucleic acid comprises a nucleotide sequence encoding a variant Csy4 polypeptide, as described above.

A nucleotide sequence encoding a subject sequence-specific endoribonuclease (e.g., a subject sequence-specific, enzymatically active endoribonuclease; a subject sequence-specific, enzymatically inactive endoribonuclease) can be operably linked to a transcription control element (e.g., a promoter, an enhancer, etc.). Suitable promoter and enhancer elements are known in the art. For expression in a bacterial cell, suitable promoters include, but are not limited to, lacI, lacZ, T3, T7, gpt, lambda P and trc. For expression in a eukaryotic cell, suitable promoters include, but are not limited to, cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters.

In some embodiments, e.g., for expression in a yeast cell, a suitable promoter is a constitutive promoter such as an ADH1 promoter, a PGK1 promoter, an ENO promoter, a PYK1 promoter and the like; or a regulatable promoter such as a GAL1 promoter, a GAL10 promoter, an ADH2 promoter, a PHO5 promoter, a CUP1 promoter, a GAL7 promoter, a MET25 promoter, a MET3 promoter, a CYC1 promoter, a HIS3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1 (e.g., for use in *Pichia*). Selection of the appropriate vector and promoter is well within the level of ordinary skill in the art.

Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), a pagC promoter (Pulkkinen and Miller, *J. Bacteriol.*, 1991: 173(1): 86-93; Alpuche-Aranda et al., PNAS, 1992; 89(21): 10079-83), a nirB promoter (Harborne et al. (1992) *Mol. Micro.* 6:2805-2813), and the like (see, e.g., Dunstan et al. (1999) *Infect. Immun.* 67:5133-5141; McKelvie et al. (2004) *Vaccine* 22:3243-3255; and Chatfield et al. (1992) *Biotechnol.* 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spy promoter, and the like; a promoter derived from the pathogenicity island SPI-2 (see, e.g., WO96/17951); an actA promoter (see, e.g., Shetron-Rama et al. (2002) *Infect. Immun.* 70:1087-1096); an rpsM promoter (see, e.g., Valdivia and Falkow (1996). *Mol. Microbiol.* 22:367); a tet promoter (see, e.g., Hillen, W. and Wissmann, A. (1989) In Saenger, W. and Heinemann, U. (eds), *Topics in Molecular and Structural Biology, Protein-Nucleic Acid Interaction*. Macmillan, London, UK, Vol. 10, pp. 143-162); an SP6 promoter (see, e.g., Melton et al. (1984) *Nucl. Acids Res.* 12:7035); and the like. Suitable strong promoters for use in prokaryotes such as *Escherichia coli* include, but are not limited to Trc, Tac, T5, T7, and $P_{Lambda}$. Non-limiting examples of operators for use in bacterial host cells include a lactose promoter operator (LacI repressor protein changes conformation when contacted with lactose, thereby preventing the LacI repressor protein from binding to the operator), a tryptophan promoter operator (when complexed with tryptophan, TrpR repressor protein has a conformation that binds the operator; in the absence of tryptophan, the TrpR repressor protein has a conformation that does not bind to the operator), and a tac promoter operator (see, for example, deBoer et al. (1983) Proc. Natl. Acad. Sci. U.S.A. 80:21-25).

A nucleotide sequence encoding a subject sequence-specific endoribonuclease (e.g., a subject sequence-specific, enzymatically active endoribonuclease; a subject sequence-specific, enzymatically inactive endoribonuclease) can be present in an expression vector and/or a cloning vector. An expression vector can include a selectable marker, an origin of replication, and other features that provide for replication and/or maintenance of the vector.

Large numbers of suitable vectors and promoters are known to those of skill in the art; many are commercially available for generating a subject recombinant construct. The following vectors are provided by way of example. Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia).

Expression vectors generally have convenient restriction sites located near the promoter sequence to provide for the insertion of nucleic acid sequences encoding heterologous proteins. A selectable marker operative in the expression host may be present. Suitable expression vectors include, but are not limited to, viral vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769, WO 93/19191;

WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus); and the like.

The present disclosure provides isolated genetically modified host cells (e.g., in vitro cells) that are genetically modified with a subject nucleic acid. In some embodiments, a subject isolated genetically modified host cell can produce a subject sequence-specific endoribonuclease (e.g., a subject sequence-specific, enzymatically active endoribonuclease; a subject sequence-specific, enzymatically inactive endoribonuclease).

Suitable host cells include eukaryotic host cells, such as a mammalian cell, an insect host cell, a yeast cell; and prokaryotic cells, such as a bacterial cell. Introduction of a subject nucleic acid into the host cell can be effected, for example by calcium phosphate precipitation, DEAE dextran mediated transfection, liposome-mediated transfection, electroporation, or other known method.

Suitable mammalian cells include primary cells and immortalized cell lines. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like.

Suitable yeast cells include, but are not limited to, *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Neurospora crassa, Chlamydomonas reinhardtii*, and the like.

Suitable prokaryotic cells include, but are not limited to, any of a variety of laboratory strains of *Escherichia coli, Lactobacillus* sp., *Salmonella* sp., *Shigella* sp., and the like. See, e.g., Carrier et al. (1992) *J. Immunol.* 148:1176-1181; U.S. Pat. No. 6,447,784; and Sizemore et al. (1995) *Science* 270:299-302. Examples of *Salmonella* strains which can be employed in the present invention include, but are not limited to, *Salmonella typhi* and *S. typhimurium*. Suitable *Shigella* strains include, but are not limited to, *Shigella flexneri, Shigella sonnei,* and *Shigella disenteriae*. Typically, the laboratory strain is one that is non-pathogenic. Non-limiting examples of other suitable bacteria include, but are not limited to, *Bacillus subtilis, Pseudomonas pudita, Pseudomonas aeruginosa, Pseudomonas mevalonii, Rhodobacter sphaeroides, Rhodobacter capsulatus, Rhodospirillum rubrum, Rhodococcus* sp., and the like. In some embodiments, the host cell is *Escherichia coli*.

Kits

The present disclosure also provides kits for determining the nucleotide sequence of a target polyribonucleotide. The present disclosure provides kits for carrying out sequence-specific cleavage of a substrate polyribonucleotide. The present disclosure provides kits for carrying out detection of an RNA sequence in a target polyribonucleotide. The present disclosure provides kits for carrying out isolation of a target RNA. The present disclosure provides kits for carrying out isolation of a polypeptide that binds a target RNA.

Kits for Carrying Out Direct Sequencing of a Polyribonucleotide

A subject kit for carrying out direct sequencing of a polyribonucleotide includes at least a subject sequence-specific, enzymatically inactive endoribonuclease, where the sequence-specific, enzymatically inactive endoribonuclease is purified. In some embodiments, the enzymatically inactive, sequence-specific endoribonuclease is linked to an acceptor molecule or a donor molecule, for FRET detection.

A subject kit for carrying out direct sequencing of a polyribonucleotide includes at least a subject sequence-specific, enzymatically inactive endoribonuclease; and can include one or more additional components, where the one or more additional components can be: 1) a buffer; 2) a probe oligonucleotide comprising a defined sequence; 3) a probe oligonucleotide comprising a defined sequence, where the probe oligonucleotide is linked to an acceptor molecule or a donor molecule, for FRET detection; 4) an insoluble support, for linking to a target polyribonucleotide; 5) a positive control polyribonucleotide, where the positive control polyribonucleotide comprises a known nucleotide sequence; 6) a positive control probe oligonucleotide that binds to and forms a duplex with the known sequence of the positive control polyribonucleotide.

In addition to above-mentioned components, a subject kit can further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Kits for Carrying Out Sequence-Specific Cleavage of a Substrate Polyribonucleotide A subject kit for carrying out sequence-specific cleavage of a substrate polyribonucleotide includes at least a purified sequence-specific endoribonuclease and/or a nucleic acid comprising a nucleotide sequence encoding the sequence-specific endoribonuclease. A subject kit for carrying out sequence-specific cleavage of a substrate polyribonucleotide can include, in addition to a purified sequence-specific endoribonuclease (and/or a nucleic acid comprising a nucleotide sequence encoding the sequence-specific endoribonuclease), one or more additional components. Suitable additional components include, e.g., a buffer; a polyribonucleotide substrate that serves as a positive control; polyribonucleotide size standards; a negative control substrate; and the like. The components can each be in separate containers. The kit can further include one or more positive and negative controls.

In addition to above-mentioned components, a subject kit can further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Kits for Carrying Out Detection of a Sequence in a Target Polyribonucleotide

A subject kit for carrying out detection of a sequence in a target polyribonucleotide (e.g., for carrying out detection of a polyribonucleotide) can include an oligonucleotide probe comprising a known sequence. In some embodiments, the kit will include an oligonucleotide probe comprising a known sequence and comprising a detectable moiety, e.g., a polypeptide that can be detected using an immunological assay; a fluorescent protein; a luciferin; etc. The kit can further include a positive control polyribonucleotide that comprises a nucleotide sequence capable of forming a duplex with the oligonucleotide probe. The kit can further include an enzymatically active, sequence-specific endoribonuclease that specifically detects and cleaves a duplex formed by the oligonucleotide probe and a target polyribonucleotide. The kit can further include one or more of a buffer; components for detecting the detectable moiety; a test strip; and the like. The kit can further include one or more positive and negative controls.

In addition to above-mentioned components, a subject kit can further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Kits for Carrying Out Isolation of a Target RNA

A subject kit for carrying out isolation (e.g., purification) of a target RNA can include one or more of: 1) a subject sequence-specific, enzymatically inactive endoribonuclease; 2) an expression construct comprising a "tag" nucleotide sequence, i.e., a nucleotide sequence that is specifically bound by the sequence-specific, enzymatically inactive endoribonuclease, where a nucleotide sequence encoding a target RNA of choice can be inserted 3' of the "tag" nucleotide sequence; and 3) imidazole. The sequence-specific, enzymatically inactive endoribonuclease can be immobilized on an insoluble support. The kit can further include a liquid composition for contacting a mixed population of nucleic acids with the immobilized sequence-specific, enzymatically inactive endoribonuclease. The kit can further include a wash buffer. The kit can further include one or more positive and negative controls. A positive control could include an expression vector comprising a nucleotide sequence encoding a tagged target RNA, where the tag is specifically bound by the sequence-specific, enzymatically inactive endoribonuclease. The components can each be in separate containers.

For example, a subject kit can include a subject sequence-specific, enzymatically inactive endoribonuclease. A subject kit can further include a recombinant expression vector comprising, in order from 5' to 3' and in operable linkage: a) a nucleotide sequence encoding an RNA substrate that is specifically bound by a subject variant Csy4 endoribonuclease; and b) a multiple cloning site suitable for insertion of a nucleic acid encoding the target RNA. The nucleotide sequence encoding the RNA substrate can be operably linked to a promoter. In some instances, the promoter is an inducible promoter. The RNA substrate can comprise the nucleotide sequence 5'-GUUCACUGCCGUAUAGGCAGCUAAGAAA-3' (SEQ ID NO:1) or any of the recognition sequences depicted in FIG. 5 or FIG. 11. In some cases, the recombinant expression vector comprises, inserted into the multiple cloning site, a nucleotide sequence encoding the target RNA. The kit can further include a buffer that lacks imidazole. The kit can further include imidazole or an imidazole solution. The kit can further include one or more wash buffers. In some cases, the kit will include a positive control expression vector. The variant Csy4 endoribonuclease can be immobilized on an insoluble support, where suitable insoluble supports include, but are not limited to agarose beads, magnetic beads, a test strip, a multi-well dish, and the like. The insoluble support can comprise a variety of substances (glass, polystyrene, polyvinyl chloride, polypropylene, polyethylene, polycarbonate, dextran, nylon, amylose, natural and modified celluloses, polyacrylamides, agaroses, and magnetite) and can be provided in a variety of forms, including, e.g., agarose beads, polystyrene beads, latex beads, magnetic beads, colloid metal particles, glass and/or silicon chips and surfaces, nitrocellulose strips, nylon membranes, sheets, wells of reaction trays (e.g., multi-well plates), plastic tubes, etc.

In addition to above-mentioned components, a subject kit can further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Methods of Directly Sequencing a Target Polyribonucleotide

The present disclosure provides a method of directly determining the nucleotide sequence of a target polyribonucleotide. Thus, for example, the method does not require synthesis of a polydeoxyribonucleotide counterpart of a target polyribonucleotide in order to determine the nucleotide sequence of the target polyribonucleotide.

Viral diagnostics, personalized medicine, single-cell transcript analysis, and translational profiling are all fields in which direct RNA detection and sequencing find use. A subject polyribonucleotide sequencing method, and a subject method of detecting a specific sequence in a polyribonucleotide, find use in these various fields.

A subject polyribonucleotide sequencing method generally involves: a) contacting a target polyribonucleotide with an oligonucleotide probe comprising a specific known sequence and an enzymatically inactive sequence-specific endoribonuclease under conditions that favor duplex formation between the oligonucleotide probe and the target polyribonucleotide, wherein the enzymatically inactive sequence-specific endoribonuclease binds the specific sequence in the duplex; and b) detecting specific binding between the oligonucleotide probe and the target polyribonucleotide, where specific binding of the enzymatically inactive sequence-specific endoribonuclease to the duplex indicates the presence of the specific sequence in the target polyribonucleotide.

In some cases, the enzymatically inactive sequence-specific endoribonuclease is linked (covalently or non-covalently) to an emissive label. By "emissive label" is meant any molecule that may be detected via its inherent emission properties, which include emission detectable upon excitation. Suitable emissive labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, Texas Red, IAEDANS, EDANS, BODIPY FL, LC Red 640, Cy 5, Cy 5.5, LC Red 705 and Oregon green. Suitable optical dyes are described in the 2002 Molecular Probes Handbook, 9th Ed., by Richard P. Haugland.

In some instances, the oligonucleotide probe used in a subject polyribonucleotide sequencing method is linked to a donor molecule, the enzymatically inactive sequence-specific endoribonuclease is linked to an acceptor molecule, and detection of duplex formation is by fluorescence resonance energy transfer (also referred to as "Förster resonance energy transfer" or "FRET").

Förster resonance energy transfer (FRET) is phenomenon known in the art wherein excitation of one emissive dye is transferred to another without emission of a photon. A FRET pair consists of a donor chromophore and an acceptor chromophore (where the acceptor chromophore may be a quencher molecule). The emission spectrum of the donor and the absorption spectrum of the acceptor must overlap, and the two molecules must be in close proximity. The distance between donor and acceptor at which 50% of donors are deactivated (transfer energy to the acceptor) is defined by the Förster radius, which is typically 10-100 angstroms. Changes in the emission spectrum comprising FRET pairs can be detected, indicating changes in the number of that are in close proximity (i.e., within 100 angstroms of each other). This will typically result from the binding or dissociation of two molecules, one of which is labeled with a FRET donor and the other of which is labeled with a FRET acceptor, wherein such binding brings the FRET pair in close proximity.

Binding of such molecules will result in an increased emission of the acceptor and/or quenching of the fluorescence emission of the donor. FRET pairs (donor/acceptor) suitable for use include, but are not limited to, EDANS/fluorescein, IAEDANS/fluorescein, fluorescein/tetramethylrhodamine, fluorescein/Cy 5, IEDANS/DABCYL, fluorescein/QSY-7, fluorescein/LC Red 640, fluorescein/Cy 5.5 and fluorescein/LC Red 705. In addition, a fluorophore/quantum dot donor/acceptor pair can be used. EDANS is (5-((2-Aminoethyl)amino)naphthalene-1-sulfonic acid); IAEDANS is 5-({2-[(iodoacetyl)amino]ethyl}amino)naphthalene-1-sulfonic acid); DABCYL is 4-(4-dimethylaminophenyl) diazenylbenzoic acid.

Cy3, Cy5, Cy 5.5, and the like, are cyanines. For example, Cy3 and Cy5 are reactive water-soluble fluorescent dyes of the cyanine dye family. Cy3 dyes are red (~550 nm excitation, ~570 nm emission and therefore appear green), while Cy5 is fluorescent in the red region (~650/670 nm) but absorbs in the orange region (~649 nm). Alexa Fluor dyes, Dylight, IRIS Dyes, Seta dyes, SeTau dyes, SRfluor dyes and Square dyes can also be used.

In another aspect of FRET, an emissive donor molecule and a nonemissive acceptor molecule ("quencher") may be employed. In this application, emission of the donor will increase when quencher is displaced from close proximity to the donor and emission will decrease when the quencher is brought into close proximity to the donor. Useful quenchers include, but are not limited to, DABCYL, QSY 7 and QSY 33. Useful fluorescent donor/quencher pairs include, but are not limited to EDANS/DABCYL, Texas Red/DABCYL, BODIPY/DABCYL, Lucifer yellow/DABCYL, coumarin/DABCYL and fluorescein/QSY 7 dye.

In some cases, the enzymatically inactive sequence-specific endoribonuclease is linked (covalently or non-covalently) to a label enzyme. By "label enzyme" is meant an enzyme which may be reacted in the presence of a label enzyme substrate which produces a detectable product. Suitable label enzymes also include optically detectable labels (e.g., in the case of horse radish peroxidase (HRP)). Suitable label enzymes include but are not limited to, HRP, alkaline phosphatase, luciferase, β-galactosidase, and glucose oxidase. Methods for the use of such substrates are well known in the art. The presence of the label enzyme is generally revealed through the enzyme's catalysis of a reaction with a label enzyme substrate, producing an identifiable product. Such products may be opaque, such as the reaction of horseradish peroxidase with tetramethyl benzedine, and may have a variety of colors. Other label enzyme substrates, such as Luminol (available from Pierce Chemical Co.), have been developed that produce fluorescent reaction products. Methods for identifying label enzymes with label enzyme substrates are well known in the art and many commercial kits are available. Examples and methods for the use of various label enzymes are described in Savage et al., Previews 247:6-9 (1998), Young, J. Virol. Methods 24:227-236 (1989).

In some cases, the enzymatically inactive sequence-specific endoribonuclease comprises a radioisotope. By "radioisotope" is meant any radioactive molecule. Suitable radioisotopes for use in the invention include, but are not limited to $^{14}$C, $^{3}$H, $^{32}$P, $^{33}$P, $^{35}$S, $^{125}$I, and $^{131}$I. The use of radioisotopes as labels is well known in the art.

In some cases, the enzymatically inactive sequence-specific endoribonuclease is linked (covalently or non-covalently) to a member of a specific binding pair ("partner of a binding pair"). By "partner of a binding pair" or "member of a binding pair" is meant one of a first and a second moiety, wherein the first and the second moiety have a specific binding affinity for each other. Suitable binding pairs include, but are not limited to, antigen/antibodies (for example, digoxigenin/anti-digoxigenin, dinitrophenyl (DNP)/anti-DNP, dansyl-X-anti-dansyl, fluorescein/anti-fluorescein, lucifer yellow/anti-lucifer yellow, and rhodamine anti-rhodamine), biotin/avidin (or biotin/streptavidin) and calmodulin binding protein (CBP)/calmodulin.

In some embodiments, the oligonucleotide probe comprises a modification that provides for increased resistance to non-specific hydrolysis. Such modifications are well known in the art and include, e.g., nuclease-resistant internucleosidic linkages, modified backbones, base modifications, base substitutions, sugar modifications, and the like.

Suitable modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, phosphorodiamidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Suitable oligonucleotides having inverted polarity comprise a single 3' to 3' linkage at the 3'-most internucleotide linkage i.e. a single inverted nucleoside residue which may be a basic (the nucleobase is missing or has a hydroxyl group in place thereof). Various salts (such as, for example, potassium or sodium), mixed salts and free acid forms are also included.

A modified oligonucleotide can comprise one or more phosphorothioate and/or heteroatom internucleoside linkages, in particular —CH$_2$—NH—O—CH$_2$—, —CH$_2$—N (CH$_3$)—O—CH$_2$— (known as a methylene (methylimino) or MMI backbone), —CH$_2$—O—N(CH$_3$)—CH$_2$—, —CH$_2$—N(CH$_3$)—N(CH$_3$)—CH$_2$— and —O—N(CH$_3$)—CH$_2$—CH$_2$— (wherein the native phosphodiester internucleotide linkage is represented as —O—P(=O)(OH)—O—CH$_2$—). MMI type internucleoside linkages are disclosed in the above referenced U.S. Pat. No. 5,489,677. Suitable amide internucleoside linkages are disclosed in t U.S. Pat. No. 5,602,240.

A modified oligonucleotide can comprise one or more morpholino backbone structures as described in, e.g., U.S. Pat. No. 5,034,506. For example, in some embodiments, a modified oligonucleotide comprises a 6-membered morpholino ring in place of a ribose ring. In some of these embodiments, a phosphorodiamidate or other non-phosphodiester internucleoside linkage replaces a phosphodiester linkage. Morpholino nucleic acids ("morpholinos") include bases bound to morpholine rings instead of deoxyribose rings; in addition, the phosphate backbone can include a non-phosphate group, e.g., a phosphorodiamidate group instead of phosphates. Summerton (1999) Biochim. Biophys. Acta 1489:141; Heasman (2002) Dev. Biol. 243:209; Summerton and Weller (1997) Antisense & Nucl. Acid Drug Dev. 7:187; Hudziak et al. (1996) Antisense & Nucl. Acid Drug Dev. 6:267; Partridge et al. (1996) Antisense & Nucl. Acid Drug Dev. 6:169; Amantana et al. (2007) Bioconj. Chem. 18:1325; Morcos et al. (2008) BioTechniques 45:616.

A modified oligonucleotide can comprise a modified backbone. Modified polynucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH$_2$ component parts.

A modified oligonucleotide can comprise one or more substituted sugar moieties. Suitable oligonucleotides comprise a sugar substituent group selected from: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C$_1$ to C$_{10}$ alkyl or C$_2$ to C$_{10}$ alkenyl and alkynyl. Also suitable are O((CH$_2$)$_n$O)$_m$CH$_3$, O(CH$_2$)$_n$OCH$_3$, O(CH$_2$)$_n$NH$_2$, O(CH$_2$)$_n$CH$_3$, O(CH$_2$)$_n$ONH$_2$, and O(CH$_2$)$_n$ON((CH$_2$)$_n$CH$_3$)$_2$, where n and m are from 1 to about 10. Other suitable oligonucleotides comprise a sugar substituent group selected from: C$_1$ to C$_{10}$ lower alkyl, substituted lower alkyl, alkenyl, alkynyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, and the like. A suitable modification includes 2'-methoxyethoxy (2'-O—CH$_2$CH$_2$OCH$_3$, also known as 2'-O-(2-methoxyethyl) or 2'-MOE) (Martin et al., Helv. Chim. Acta, 1995, 78, 486-504) i.e., an alkoxyalkoxy group. A further suitable modification includes 2'-dimethylaminooxyethoxy, i.e., a O(CH$_2$)$_2$ON(CH$_3$)$_2$ group, also known as 2'-DMAOE, and 2'-dimethylaminoethoxyethoxy (also known in the art as 2'-O-dimethyl-amino-ethoxy-ethyl or 2'-DMAEOE), i.e., 2'-O—CH$_2$—O—CH$_2$—N(CH$_3$)$_2$.

A modified oligonucleotide can comprise one or more nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH₃) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine (1H-pyrimido(5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g. 9-(2-aminoethoxy)-H-pyrimido(5,4-(b) (1,4)benzoxazin-2 (3H)-one), carbazole cytidine (2H-pyrimido(4,5-b)indol-2-one), pyridoindole cytidine (H-pyrido(3',2':4,5)pyrrolo(2,3-d)pyrimidin-2-one).

Heterocyclic base moieties may also include those in which the purine or pyrimidine base is replaced with other heterocycles, for example 7-deaza-adenine, 7-deazaguanosine, 2-aminopyridine and 2-pyridone.

A suitable enzymatically inactive sequence-specific endoribonuclease includes an enzymatically inactive sequence-specific endoribonuclease described hereinbelow. For example, an enzymatically inactive sequence-specific endoribonuclease as depicted in FIG. 6 can be used.

In some embodiments, the target polyribonucleotide is linked (covalently or non-covalently) to a solid support (an insoluble support). Suitable insoluble supports include, but are not limited to, beads, plates (e.g., multi-well plates), strips, etc., where the insoluble support can comprise various materials including, but not limited to, polystyrene, polypropylene, agarose, and the like.

Oligonucleotide probes ("detection oligonucleotide") can be RNA, DNA, or any chemically modified version of an RNA or DNA, e.g., peptide nucleic acids (PNAs), locked nucleic acids (LNAs), and the like.

A subject polyribonucleotide sequencing method can include one or more washing steps, e.g., to remove non-specifically bound components such as non-specifically bound oligonucleotide probes, any non-specifically bound detectable moieties, and the like.

A non-limiting example of how to carry out a subject polyribonucleotide sequencing method is as follows. A target polyribonucleotide bound to a solid support. The target polyribonucleotide is of unknown sequence and is the "RNA to be sequenced." Four oligonucleotide probes of four different known nucleotide sequences each comprise a different fluorophore (fluorophores 1-4). The fluorophores are members of FRET pairs. The counterpart members of the FRET pairs are quantum dots. The quantum dot is linked to an enzymatically inactive sequence-specific endoribonuclease. The enzymatically inactive sequence-specific endoribonuclease binds, but does not cleave, the duplex formed between an oligonucleotide probe and the target polyribonucleotide. Only one of the four oligonucleotide probes binds to and forms a duplex with the target polyribonucleotide. A washing step removes any unbound oligonucleotide probes. Binding of oligonucleotide probe-fluorophore2 results in duplex formation with the target polyribonucleotide. Fluorophore2 is thus brought into proximity to the quantum dot linked to the enzymatically inactive sequence-specific endoribonuclease, and fluorescence is quenched.

Methods of Cleaving a Polyribonucleotide

The present disclosure provides a method of cleaving a polyribonucleotide in a sequence-specific manner. The method generally involves contacting a substrate polyribonucleotide with an enzymatically active sequence-specific endoribonuclease (e.g., a Csy4 endoribonuclease) under conditions that favor sequence-specific cleavage of the polyribonucleotide substrate. A subject method of cleaving a polyribonucleotide in a sequence-specific manner can be used to: 1) remove an affinity tag from a substrate polyribonucleotide; 2) to generate a population of product polyribonucleotides having homogeneity at the 5' end, e.g., where the substrate polyribonucleotides are in vitro transcribed mRNAs; and 3) to regulate gene expression in a cell in vitro or in vivo.

Substrate Polyribonucleotides

The terms "substrate polyribonucleotide" and "target polyribonucleotide" are used interchangeably herein to refer to a polyribonucleotide that is bound by a sequence-specific endoribonuclease in a sequence-specific manner. A substrate polyribonucleotide can be single stranded. In some instances, a substrate polyribonucleotide is double stranded.

An endoribonuclease binds to and cleaves a substrate polyribonucleotide in a sequence-specific manner. Thus, for example, an endoribonuclease binds to and cleaves a substrate polyribonucleotide at a specific sequence, referred to herein as a "recognition sequence" or a "recognition site."

A recognition sequence can be a tetranucleotide sequence, a pentanucleotide sequence, a hexanucleotide sequence, a heptanucleotide sequence, an octanucleotide sequence, or longer than an octanucleotide. For example, in some embodiments, the recognition sequence is 9 ribonucleotides, 10 ribonucleotides, 11 ribonucleotides, 12 ribonucleotides, 13 ribonucleotides, 14 ribonucleotides, 15 ribonucleotides, 16 ribonucleotides, 17 ribonucleotides, 18 ribonucleotides, 19 ribonucleotides, or 20 ribonucleotides in length. In some embodiments, a sequence-specific endoribonuclease cleaves immediately 5' of a recognition sequence. In some embodiments, a sequence-specific endoribonuclease cleaves immediately 3' of a recognition sequence. In some embodiments, a sequence-specific endoribonuclease cleaves within a recognition sequence. In some cases, a recognition sequence is immediately 5' of a secondary structure. In some cases, a recognition sequence is located 5' of a secondary structure and within 1 nucleotide (nt), 2 nt, 3 nt, 4 nt, 5 nt, or 5 nt to 10 nt of the secondary structure. In some cases, a recognition sequence is immediately 3' of a secondary structure. In some cases, a recognition sequence is located 3' of a secondary structure and within 1 nucleotide (nt), 2 nt, 3 nt, 4 nt, 5 nt, or 5 nt to 10 nt of the secondary structure.

In some embodiments, the recognition sequence (i.e., RNA recognitions sequence) is derived from an RNA that naturally occurs in the same species as that from which the Csy4 polypeptide is derived. In such a case, the RNA recognition sequence is considered a cognate sequence for the Csy4 polypeptide. For example, FIG. 5 and FIG. 11 depict Csy4 polypeptides derived from a variety of species (i.e., naturally occur in those species). In each case, a cognate RNA recognition sequence (or multiple different cognate RNA recognition sequences) is listed that is derived from the same species. In some embodiments, the recognition sequence is derived from an RNA that naturally occurs in a different species as that from which the Csy4 polypeptide is derived (see FIG. 13 for examples).

In some embodiments, a substrate polyribonucleotide comprises the structure $X_xX_2X_3X_4X_5X_6X_7X_8X_9X_{10}X_{11}X_{12}X_{13}X_{14}X_{15}$, where nucleotides $X_1$-$X_5$ base pair with $X_{11}$-$X_{15}$ such that $X_1$ and $X_{15}$ form the base of a stem structure, and such that $X_6$, $X_7$, $X_8$, $X_9$, and $X_{10}$ form a loop; the structure is a regular A-form helical structure.

In some embodiments, the substrate polyribonucleotide comprises an affinity tag; and a subject method provides for removal of the affinity tag from the substrate polyribonucleotide.

Sequence-Specific Endoribonucleases

Endoribonucleases that bind to and cleave a substrate polyribonucleotide in a sequence-specific manner include enzymatically active polypeptides that cleave (hydrolyze) a substrate polyribonucleotide in a metal ion-independent fashion.

Structural features of an endoribonuclease that binds to and cleaves a substrate polyribonucleotide in a sequence-specific and metal ion-independent manner can include one or more of the following: 1) a highly basic alpha helix for sequence non-specific recognition of the phosphate backbone of RNA through the RNA major groove, e.g., R114, R115, R118, R119, or equivalents thereof; 2) R102 and/or Q104, or equivalents thereof, making hydrogen bonding contacts with the major groove of the RNA stem; 3) and one or more of His29, Ser148, and Tyr176, or equivalents thereof, involved in catalysis; and 4) F155, or an equivalent thereof.

Endoribonucleases that bind to and cleave a substrate polyribonucleotide in a sequence-specific manner include enzymatically active polypeptides that have at least about 75%, at least about 80%, at least about 85%, at least about 90%, at least about 95%, at least about 98%, at least about 99%, or 100%, amino acid sequence identity to an amino acid sequence set forth in FIG. 4 (Csy4 amino acid sequences).

Endoribonucleases that bind to and cleave a substrate polyribonucleotide in a sequence-specific manner include enzymatically active polypeptides that have at least about 75%, at least about 80%, at least about 85%, at least about 90%, at least about 95%, at least about 98%, at least about 99%, or 100%, amino acid sequence identity to an amino acid sequence set forth in FIG. 5 or FIG. 11 (SEQ ID NO: 39, 79, 84, 90, 104, 108, or 110) (Csy4 amino acid sequences).

Endoribonucleases that bind to and cleave a substrate polyribonucleotide in a sequence-specific manner include enzymatically active polypeptides that have at least about 75%, at least about 80%, at least about 85%, at least about 90%, at least about 95%, at least about 98%, at least about 99%, or 100%, amino acid sequence identity to a Cas6 amino acid sequence.

Endoribonucleases that bind to and cleave a substrate polyribonucleotide in a sequence-specific manner include enzymatically active polypeptides that have at least about 75%, at least about 80%, at least about 85%, at least about 90%, at least about 95%, at least about 98%, at least about 99%, or 100%, amino acid sequence identity to a CasE amino acid sequence.

Endoribonucleases that bind to and cleave a substrate polyribonucleotide in a sequence-specific manner include enzymatically active polypeptides that differ from an amino acid sequence set forth in any one of FIG. 4 or 5 by from 1 to 20 (e.g., 1, 2, 3, 4, 5, 6, 7, 8, 9, 10, 11, 12, 13, 14, 15, 16, 17, 18, 19, or 20) amino acid substitutions and/or insertions and/or deletions.

Reaction Conditions

A sequence-specific endoribonuclease can hydrolyze a substrate polyribonucleotide in a sequence-specific manner at a temperature in a range from about 15° C. to about 100° C., e.g., in a range of from about 15° C. to about 17° C., from about 17° C. to about 20° C., from about 20° C. to about 25° C., from about 25° C. to about 30° C., from about 30° C. to about 40° C., from about 40° C. to about 50° C., from about 50° C. to about 60° C., from about 60° C. to about 70° C., from about 70° C. to about 80° C., from about 80° C. to about 90° C., or from about 90° C. to about 100° C.

A sequence-specific endoribonuclease can hydrolyze a substrate polyribonucleotide in a sequence-specific manner in a pH range of from about 4.0 to about 8.0, e.g., from about pH 4.0 to about 4.5, from about pH 4.5 to about 5.0, from about pH 5.0 to about 5.5, from about pH 5.5 to about 6.0, from about pH 6.0 to about 6.5, from about pH 6.5 to about 7.0, from about pH 7.0 to about 7.5, from about pH 6.5 to about 7.5, from about pH 7.5 to about 8.0, from about pH 6.5 to about 8.0, or from about pH 5.5 to about 7.5.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1

Direct RNA Detection and Sequencing Using Csy4 Family Proteins

Materials and Methods

Wild-type Csy4, point mutants and selenomethionine (SeMet)-substituted Csy4 were expressed in Rosetta 2(DE3) cells as either a His$_6$-maltose binding protein (MBP) fusion or a His$_6$ fusion protein and purified by Ni-affinity chromatography, followed by proteolytic removal of the His(MBP) tag, a further Ni-affinity step, and size exclusion chromatography. The pre-crRNAs were transcribed in vitro with T7 polymerase and purified on a denaturing gel. The complex was formed by incubating RNA with Csy4 at a 2:1 ratio for 30 minutes at 30° C. followed by size exclusion chromatography. The complex was crystallized using the hanging-drop method in 200 mM sodium citrate pH 5.0, 100 mM magnesium chloride, 20% (w/v) poly(ethylene glycol) (PEG)-4000 (wild-type (WT) complex) or 150 mM sodium acetate pH 4.6, 17% PEG4000 or 160 mM sodium acetate pH 4.6, 18% PEG4000 (S22C-containing complex). The structure of the WT Csy4-RNA complex was determined by the multiwavelength anomalous dispersion (MAD) method using SeMet-substituted crystals. The structure of the Csy4 (S22C)-RNA complex was determined by molecular replacement.

Gene Annotation, Cloning, Protein Expression and Purification.

Comparative sequence analysis of Csy4 genes across species identified a conserved region 20 codons upstream of the annotated start codon in the PA14 genome. Lee, et al. *Genome Biol* 7, R90 (2006). The conserved Csy4 (PA14_33300) sequence was PCR amplified from *Pseudomonas aeruginosa* UCBPP-PA14 genomic DNA using Pa14Csy4_fwd: caccatggaccactacctcgacattcg and Pa14Csy4_rev: gaaccagggaacgaaacctcc. The polymerase chain reaction (PCR) product was cloned using the Gateway system into the pENTR/TEV/D-TOPO entry vector (Invitrogen), followed by site-specific recombination into expression vector pHGWA or pHMGWA. Busso, et al. *Analytical Biochemistry* 343, 313-321, (2005). Point mutations were introduced into Csy4 using the QuikChange Site-Directed Mutagenesis Kit (Stratagene). The Pa14Csy4 expression plasmid was transform into *E. coli* Rosetta 2 (DE3) cells (Novagen) or co-transformed with a pMK vector expressing CRISPR RNA synthesized by Geneart (Regensburg, Germany). Rosetta 2 (DE3) cells were grown in Luria Broth (LB) supplemented with ampicillin and chloramphenicol. Protein expression was induced with 0.5 mM isopropyl β-D-1-thiogalactopyranoside (IPTG) (Affymetrix) at a cell density of ~0.5OD followed by shaking at 18° C. for 16 hours. Cells were pelleted and resuspended in lysis buffer (15.5 mM disodium hydrogen phosphate, 4.5 mM sodium dihydrogen phosphate, 500 mM sodium chloride, 10 mM imidazole, protease inhibitors, 5% glycerol, 0.01% Triton X-100, 100µ/ml DNaseI, 1 mM Tris[2-carboxyethyl]phosphine hydrochloride (TCEP), 0.5 mM phenylmethylsulfonyl fluoride, pH 7.4) and sonicated on ice for two minutes in 10 second bursts. Lysate was clarified by centrifugation (24,000×g, 30 minutes) and incubated with nickel-nitrilotriacetic acid (Ni-NTA) affinity resin in batch (Qiagen). The bound protein was eluted with high imidazole buffer (15.5 mM disodium hydrogen phosphate, 4.5 mM sodium dihydrogen phosphate, 500 mM sodium chloride, 300 mM imidazole, 1 mM TCEP, 5% glycerol, pH 7.4) and dialyzed overnight in dialysis buffer (elution buffer with only 20 mM imidazole) in the presence of tobacco etch virus (TEV) to cleave the $His_6$ or $His_6$MBP tag. The protein was concentrated (Amicon) and purified on a nickel affinity column (GE) followed by tandem Sup75 (16/60) columns in gel filtration buffer (100 mM HEPES pH 7.5, 500 mM KCl, 5% glycerol, 1 mM TCEP). Sample was then dialyzed against gel filtration buffer containing only 150 mM potassium chloride. A similar protocol was used for preparation of the selenomethionine (SeMet)-derivitized protein and the only notable difference was the expression media. Briefly, BL21 (DE3) cells transformed with Csy4(pHGWA) expression vector were grown in M9 minimal media supplemented with ampicillin, as previously described. Wiedenheft, et al. *Structure* 17, 904-912 (2009).

Nuclease Activity Assays.

75 pmol of wild-type or mutant Csy4 were incubated with 5 pmol in vitro transcribed Pa14 pre-crRNA (prepared as described; Wiedenheft (2009) supra) in 10 µl reactions containing 20 mM HEPES pH 7.5, 100 mM potassium chloride buffer at 25° C. for five minutes. Reactions were quenched with the addition of 50 ul acid phenol-chloroform (Ambion). 10 µl additional reaction buffer were added and samples were centrifuged (16,000×g, 30 minutes) and 16 µl aqueous sample was removed, mixed 1:1 with 2× formamide loading buffer, and separated on 15% denaturing polyacrylamide gel. RNA was visualized with SYBR Gold staining (Invitrogen).

Crystallization.

All crystallization experiments were performed at 18° C. using the hanging drop vapour diffusion method by mixing equal volumes (1 µl+1 µl) of the complex and reservoir solutions. Plate-shaped crystals of the wild-type Csy4-RNA complex were grown in 200 mM sodium citrate pH 5.0, 100 mM magnesium chloride, 20% (w/v) poly(ethylene glycol)-4000 (PEG4000). These crystals belonged to the space group C2, contained one copy of the complex in the asymmetric unit and diffracted to 2.3 Å resolution at synchrotron X-ray sources. Using complex reconstituted with the Csy4S22C point mutant, two additional crystal forms were obtained in 150 mM sodium acetate pH 4.6, 17% (w/v) PEG4000 and 160 mM sodium acetate pH 4.6, 18% PEG4000. Initially, hexagonal crystals appeared within 24 hr. These crystals diffracted to 2.6 Å resolution, belonged to space group $P6_1$ and contained one copy of the complex in the asymmetric unit. 48 hr later, the same crystallization condition yielded needle-shaped crystals that belonged to space group P212121, contained two copies of the complex and diffracted up to 1.8 Å resolution. For data collection, all crystal forms were cryoprotected by soaking in their respective mother liquor supplemented with 30% glycerol prior to flash cooling in liquid nitrogen.

Structure Determination.

All diffraction data we collected at 100 K on beamlines 8.2.2 and 8.3.1 of the Advanced Light Source (Lawrence Berkeley National Laboratory). Data were processed using XDS. Kabsch, *Acta Crystallogr D Biol Crystallogr* 66, 125-132 (2010). Experimental phases were determined from a three-wavelength multiwavelength anomalous dispersion (MAD) experiment (peak, inflection and remote data sets) using the monoclinic Csy4-RNA crystals containing selenomethionine-substituted wild-type Csy4. Two selenium sites were located using the Hybrid Substructure Search (HySS) module of the Phenix package. Grosse-Kunstleve, and Adams. *Acta Crystallogr D Biol Crystallogr* 59, 1966-1973 (2003). Substructure refinement, phasing and density modification were performed using AutoSHARP. Vonrhein, et al. *Methods Mol Biol* 364, 215-230 (2007). The resulting electron density map exhibited clear layers of density attributable to protein and RNA alternating along the c-axis, with the RNA layer made up of two coaxially-stacked RNA helices engaged in a "kissing loop" interaction. An initial atomic model for the Csy4 protein was obtained by automatic building using the Phenix AutoBuild module. Terwilliger, et al. *Acta Crystallogr D Biol Crystallogr* 64, 61-69, (2008). The complex model was completed by iterative cycles of manual building in COOT (Emsley, and Cowtan, *Acta Crystallogr D Biol Crystallogr* 60, 2126-2132 (2004)) and refinement using Phenix.refine[36] (Adams, et al. *Acta Crystallogr D Biol Crystallogr* 66, 213-221 (2010)) against a native 2.33 Å resolution dataset, yielding a final model with a crystallographic $R_{work}$ factor of 21.4% and a $R_{free}$ factor of 26.4% (Table 1).

TABLE 1

Data collection, phasing and refinement statistics

| | Native WT | Native S22C | Native S22C | | SeMet WT | |
|---|---|---|---|---|---|---|
| Data collection | | | | | | |
| Space group | C2 | $P2_12_12_1$ | $P6_1$ | | C2 | |
| Cell dimensions | | | | | | |
| a, b, c (Å) | 62.37, 72.77, 86.82 | 40.1, 78.9, 145.9 | 39.25, 39.25, 297.37 | | 62.33, 47.23, 87.26 | |
| α, β, γ (°) | 90.0, 108.2, 90.0 | 90.0, 90.0, 90.0 | 90.0, 90.0, 120.0 | | 90.0, 108.3, 90.0 | |
| | | | | Peak | Inflection | Remote |
| Wavelength (Å) | 1.11159 | 0.99992 | 1.11588 | 0.97949 | 0.97971 | 0.97204 |
| Resolution (Å)* | 19.68-2.33 | 69.4-1.80 | 22.38-2.60 | 82.86-2.80 | 82.86-2.80 | 82.86-2.80 |
| | (2.50-2.33) | (1.90-1.80) | (2.70-2.60) | (2.90-2.80) | (2.90-2.80) | (2.90-2.80) |
| $R_{sym}$ (%)* | 5.8 (44.6) | 7.0 (52.8) | 3.3 (31.1) | 9.4 (38.3) | 8.9 (38.5) | 9.0 (38.1) |
| I/σ/* | 18.9 (3.35) | 31.1 (3.1) | 29.8 (3.8) | 17.0 (4.4) | 14.5 (3.7) | 14.5 (3.6) |
| Completeness (%)* | 96.6 (98.3) | 98.7 (91.0) | 99.4 (98.5) | 99.6 (96.7) | 99.5 (99.3) | 99.3 (96.4) |
| Redundancy* | 4.4 (4.4) | 19.8 (6.5) | 6.1 (5.4) | 5.7 (5.3) | 3.8 (3.7) | 3.8 (3.7) |
| Refinement | | | | | | |
| Resolution (Å) | 19.70-2.33 | 69.4-1.80 | 19.60-2.60 | | | |
| No. reflections | 9974 | 43284 | 7798 | | | |
| $R_{work}/R_{free}$ | 0.214/0.265 | 0.187/0.220 | 0.255/0.279 | | | |
| No. atoms | | | | | | |
| Protein | 1273 | 2975 | 1364 | | | |
| RNA | 313 | 642 | 321 | | | |
| Water/ligands | 41 | 386 | 5 | | | |
| B-factors | | | | | | |
| Protein | 47.7 | 29.1 | 101.5 | | | |
| RNA | 109.3 | 35.3 | 103.0 | | | |
| Water/ligands | 44.9 | 33.5 | 74.5 | | | |
| R.m.s. deviations | | | | | | |
| Bond lengths (Å) | 0.007 | 0.011 | 0.002 | | | |
| Bond angles (°) | 1.0 | 1.5 | 0.7 | | | |

*Values in parentheses denote highest resolution shell

The model includes RNA nucleotides C1-G15 and the phosphate group of nucleotide C16 and protein residues 1-104, 109-120 and 139-187. Owing to the layered arrangement of protein and RNA in the crystal lattice and the lack of lateral crystal contacts within the RNA layer, the RNA exhibits significant disorder, as evidenced by markedly elevated temperature factors (>100 Å$^2$) and the absence of interpretable density for the nucleotide base of U9. The disorder is also evident in protein residues 109-120, corresponding to the arginine-rich helix inserted in the major groove of the RNA, for which only the polypeptide backbone could be built (except for residues Arg 115 and Arg 118).

The structures of the Csy4(S22C)-RNA complex in the hexagonal and orthorhombic crystal forms were determined by molecular replacement in Phaser (McCoy, et al. *J Appl Crystallogr* 40, 658-674 (2007)), using the Csy4 protein (lacking the arginine-rich helix) and RNA models from the monoclinic crystal form as separate search ensembles. In both crystal forms, electron density for the arginine-rich helix and the linker region comprising Csy4 residues 105-108 was immediately noticeable in $2F_o-F_c$ maps obtained from the molecular replacement solutions. The structure of the Csy4(S22C)-RNA complex in the hexagonal form was refined to an $R_{work}$ factor of 25.5% and $R_{free}$ of 27.9 at 2.6 Å resolution. The final model includes Csy4 residues 1-120 and 139-187 and RNA nucleotides C1-G15 plus the phosphate group of nucleotide C16. The orthorhombic crystal form of the Csy4(S22C)-RNA complex has been solved at 1.8 Å resolution and refined to an $R_{work}$ factor of 18.7% and $R_{free}$ of 22.0%, with excellent stereochemistry. Of the two complexes in the asymmetric unit, complex 1 (chains A and C) contains Csy4 residues 1-187 and RNA nucleotides C1-G15 plus the phosphate group of nucleotide C16, while the less ordered complex 2 (chains B and D) comprises Csy4 residues 1-187 with the exception of residues 13-15 and 135-138, which show no ordered electron density, and RNA nucleotides C1-G15 and the phosphate group of nucleotide C16. The two copies of Csy4 superpose with an rmsd of 1.15 Å over 179 Cα atoms, the greatest differences coming from the slightly different positions of the arginine-rich helix. The two RNA molecules in the asymmetric unit superpose with an rmsd of 1.49 Å, the largest deviation being due to the bulged-out nucleotide U9, which assumes different conformations in the two RNAs. Our discussion and illustrations throughout the manuscript are based on complex 1 of the orthorhombic crystal form. All structural illustrations were generated using Pymol (http://www(dot)pymol(dot)org).

Results

CRISPR-mediated immunity is thought to occur in approximately 90% of archaeal and 40% of bacterial genomes based on the presence of CRISPR loci in sequenced genomes. Horvath and Barrangou, *Science* 327, 167-170 (2010); Jansen, et al. *Molecular Microbiology* 43, 1565-1575 (2002); Sorek, et al. *Nat Rev Microbiol* 6, 181-186 (2008); Marraffini, and Sontheimer, *Nat Rev Genet* 11, 181-190 (2010). CRISPR-associated (Cas) proteins belonging to the eight known CRISPR/Cas subtypes are highly divergent at the primary sequence level, obscuring identification of functional homologues. Haft, et al. *PLoS Comput Biol* 1, e60 (2005); Makarova, et al. *Biology Direct* 1, 1-26 (2006). *Pseudomonas aeruginosa* UCBPP-PA14 (hereafter Pa14), a Gram-negative opportunistic pathogen harboring a CRISPR/Cas system of the *Yersinia* subtype, contains six Cas genes flanked by two CRISPR elements (FIG. 1A). Although Cas1 is found universally among CRISPR-containing organisms, and Cas3 is evident in most subtypes, Csy1-4 are unique to the *Yersinia* subtype. Both CRISPR elements comprise a characteristic arrangement of 28-nucleotide repeats identical within both CRISPRs (save for one nucleotide) interspersed with ~32-nucleotide unique spacers, some of which match sequences found in bacteriophage or plasmids. Grissa, et al. *BMC Bioinformatics* 8, 172 (2007). In many organisms it has been shown that CRISPR loci are transcribed as long single units and are post-transcriptionally processed to yield crRNAs that each contain one unique sequence flanked by sequences derived from the repeat element. Brouns et al. *Science* 321, 960-964 (2008); Carte, et al. *Genes and Development* 22, 3489-3496 (2008); Tang, et al. *Proc. Natl. Acad. Sci. USA* 99, 7536-7541 (2002); Lillestol, et al. *Archaea* 2, 59-72 (2006); Lillestol, et al. *Mol Microbiol* 72, 259-272 (2009); Tang, et al. *Molecular Microbiology* 55, 469-481 (2005).

To identify the protein(s) responsible for producing crRNAs from long CRISPR transcripts (pre-crRNAs) in the *Yersinia* subtype, each of the six Cas proteins from Pa14 was recombinantly expressed, and the recombinantly expressed proteins were tested for endoribonucleolytic function using an in vitro transcribed pre-crRNA. Based on sequence-specific pre-crRNA processing activity, it was found that Csy4 is the endoribonuclease responsible for crRNA biogenesis. As observed for crRNA processing within two other CRISPR/Cas subtypes (Brouns et al. (2008) supra; Carte et al. (2008) supra), CRISPR transcript cleavage is a rapid, metal ion-independent reaction. Csy4 cleaves pre-crRNA within the repeat element at the base of a predicted stem-loop structure, generating ~60 nucleotide crRNAs consisting of a 32-nucleotide unique (phage-derived) sequence flanked on the 5' and 3' ends by eight and 20 nucleotides, respectively, of repeat sequence (FIG. 1A).

For Csy4 to be effective, it was hypothesized that its RNA recognition mechanism must be highly specific in order to target only CRISPR-derived transcripts and not other cellular RNAs containing hairpins and/or related sequences. To test this, Csy4 was expressed in *E. coli* alone or co-expressed with a Pa14 CRISPR RNA. In spite of a high isoelectric point (PI=10.2), Csy4 does not associate with cellular nucleic acids; however, when co-expressed with a Pa14 CRISPR, the protein is associated with a crRNA (FIG. 1B,C). These observations underscored the specificity of Csy4 recognition, leading us to explore the protein/RNA interactions required for Csy4 substrate recognition and cleavage. Csy4 binding and activity assays were performed in vitro using RNA oligonucleotides corresponding to different regions of the 28-nucleotide Pa14 CRISPR repeat sequence. Using this approach, a minimal RNA fragment recognized by Csy4 consisting of the repeat-derived stem-loop and one downstream nucleotide was identified. Cleavage assays utilizing this minimal RNA as a substrate showed that Csy4 activity requires a 2'OH on the ribose immediately upstream of the cleavage site. A 2'-deoxyribose at this position completely abrogates cleavage, but does not disrupt Csy4 binding.

In order to obtain structural insights into crRNA recognition and cleavage, Csy4 was co-crystallized in complex with a minimal RNA substrate. To generate a stable complex for structural analysis, Csy4 was bound to the non-cleavable 16-nucleotide minimal RNA substrate described above in which the nucleotide preceding the cleavage site is a 2'-deoxynucleotide. Crystals of the complex were obtained in three unique space groups, each exhibiting different crystal packing; one contained wild-type Csy4 and two contained a Csy4 point mutant. The crystal structure of the Csy4-RNA complex was solved to a resolution of 1.8 Å (FIG. 2A, Table 1), revealing an unanticipated mechanism by which CRISPR RNA is recognized and processed for use by the CRISPR-mediated silencing machinery. Csy4 makes sequence-specific contacts in the major groove of the stem-loop of the CRISPR repeat sequence and additional sequence non-specific contacts with the phosphate backbone of the RNA stem. The majority of characterized protein/RNA interactions are mediated via the minor groove of an RNA helix; the recognition of the RNA major groove by Csy4 is a highly unusual mechanism of protein/RNA interaction.

At the primary sequence level, Csy4 is highly dissimilar from the other known endoribonucleases involved in crRNA biogenesis (CasE from *Thermus thermophiles* (Ebihara, et al. *Protein Sci* 15, 1494-1499 (2006)) and Cas6 from *Pyrococcus furiosus* Carte et al. (2008) supra), sharing only ~10% identity. The crystal structures of both CasE and Cas6 indicate that these proteins adopt tandem ferrodoxin-like folds. Notably, Csy4 shares this fold with these enzymes; in the Csy4-RNA complex, the N-terminal domain (residues 1-94) of Csy4 indeed adopts a ferredoxin-like fold. However, although the C-terminal domain (residues 95-187) shares the same secondary structure connectivity as a ferredoxin-like fold, but its conformation is markedly different. Strikingly, an arginine-rich helix (residues 108-120) from the putative C-terminal ferredoxin domain inserts into the major groove of the hairpin RNA. Structural superpositions using the DALI server (Holm, and Sander, *J Mol Biol* 233, 123-138 (1993)) indicate that Csy4 in its RNA-binding conformation superposes with CasE and Cas6 with root-mean-square deviation (rmsd) of 3.8 Å (over 111 Ca atoms) and 3.9 Å (over 104 Ca atoms), respectively. Csy4, CasE and Cas6 could be descendants of a single ancestral endoribonuclease that has diverged markedly at the sequence level as it co-evolved with the repeat sequence of the CRISPR locus, while maintaining a similar protein fold.

The crRNA substrate forms a hairpin structure, as predicted for this subclass of crRNA repeats (Kunin, et al. *Genome Biol* 8, R61 (2007)), with nucleotides 1-5 and 11-15 base pairing to produce a regular A-form helical stem. The GUAUA pentaloop contains a sheared G6-A10 base pair and a bulged-out nucleotide U9, its structure reminiscent of GNR(N)A pentaloops found in the yeast U6 small nuclear RNA intramolecular stem-loop (Huppler, et al. *Nat Struct Biol* 9, 431-435 (2002)) and in bacteriophage lamda BoxB RNA (Legault, et al. *Cell* 93, 289-299 (1998)). In the Csy4-RNA complex, the RNA stem-loop straddles the β-hairpin formed by strands β7-β8 of Csy4, with the C1-G15 base-pair directly stacking onto the aromatic side chain of Phe155 (FIG. 2B). This anchors the RNA stem and orients it at the proper angle to permit sequence-specific interactions in the major groove.

Two residues in a linker segment connecting the body of Csy4 to the arginine-rich helix, Arg102 and Gln104, make hydrogen bonding contacts in the major groove of the RNA stem, sequence-specifically recognizing G15 and A14, respectively (FIG. 2B). The Csy4-crRNA interaction is further stabilized by the insertion of the arginine-rich helix into the major groove of the RNA hairpin in the proximity of the bulged-out nucleotide U9 (FIG. 2C). The side chains of Arg 114, Arg 115, Arg 118 and Arg119 contact the phosphate groups of nucleotides 2-6. Additionally, the sidechain of Arg115 engages the base of G6 as the only sequence-specific interaction between the arginine-rich helix and the RNA hairpin. Interestingly, this interaction is highly reminiscent of how certain viral proteins interact with the major groove of dsRNA molecules, for example the Tat/Tar interaction in human immunodeficiency virus (HIV)[23] and the lambda-N/boxB complex in lambdoid phages (Cai, et al. *Nature Structural Biology* 5, 203-212 (1998)). In both cases, a highly basic α-helix is employed for sequence non-specific recognition with the phosphate backbone of RNA through the RNA major groove.

Figure 3A:
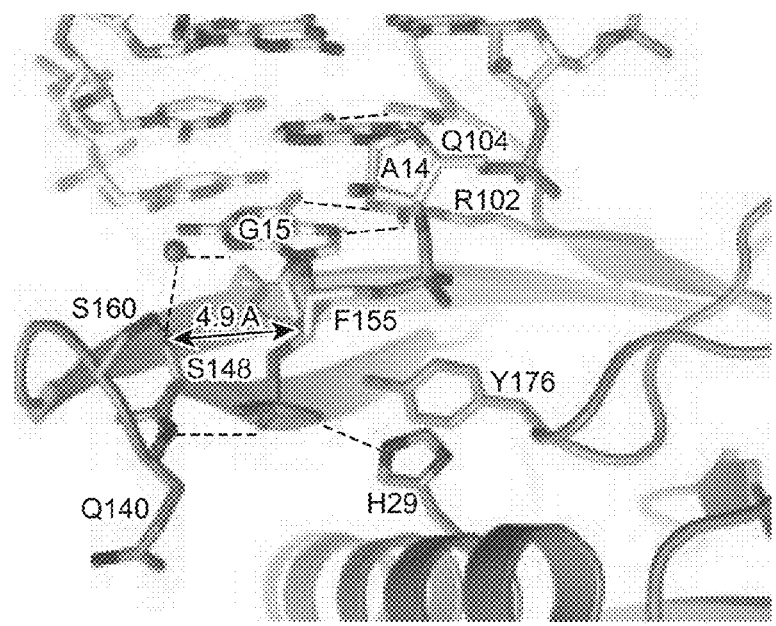
FIGS. 3A and 3B depict: a detailed view of the catalytic center of Csy4 (FIG. 3A); and cleavage activity of Csy4 wild-type (WT) and mutants (FIG. 3B).

Csy4 recognizes the hairpin element of the CRISPR repeat sequence and cleaves immediately downstream of it. The structure described in this Example contains a substrate-mimic RNA, which is not competent for cleavage. In the active site, density was observed only for the phosphate group 3' of the penultimate nucleotide, but no density for the terminal sugar or base, presumably due to the flexibility of this nucleotide (FIG. 3A). The scissile phosphate binds in a pocket located between the β-turn of the β7-β8 hairpin on one side and helix a1 and a glycine-rich loop, previously identified in Cas6 and CasE, on the other. Three residues proximal to that phosphate group are likely to participate in catalysis, His29, Ser148 and Tyr176. These residues are invariant among 12 Csy4 sequences that were identified using a BLAST search (Altschul, et al. *Nucleic Acids Research* 25, 3389-3402 (1997)) coupled with manual verification of a nearby CRISPR locus (Grissa, et al. *BMC Bioinformatics* 8, 172 (2007)) (FIG. 4).

Figure 3B:
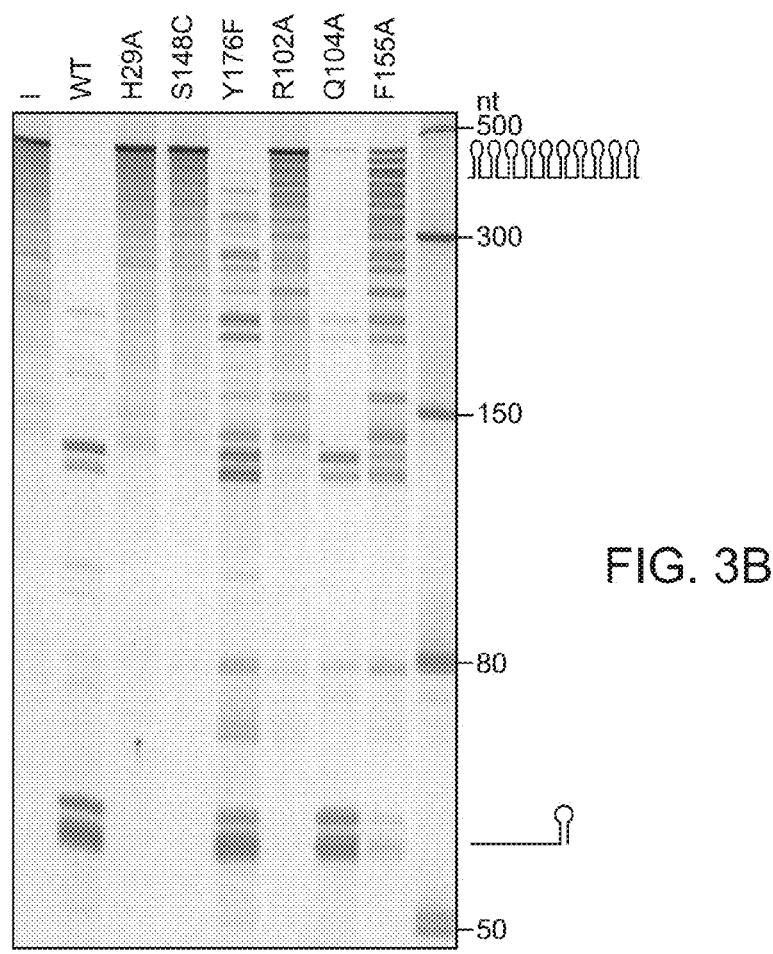

The structure suggests that several residues in Csy4 are important for mediating substrate recognition/binding and catalysis. Point mutants of each of these residues were generated; their cleavage activity was tested biochemically (FIG. 3B). Mutation of putative catalytic site residues His29 or Ser148 abolishes cleavage activity. However, mutation of Tyr176 to phenylalanine does not disrupt activity, indicating that Tyr176 may play a crucial role in orienting His29, though it does not directly participate in catalysis. Mutation of Arg102 to alanine abolishes accumulation of crRNAs, whereas mutation of Gln104 to alanine does not significantly disrupt activity, suggesting that Arg102, which recognizes the terminal base pair, is important for properly orienting the RNA substrate, but that Gln104 is not required for in vitro activity. Phe155 appears to play a large role in appropriately orienting the RNA substrate, as an alanine mutation at this residue severely impairs crRNA biogenesis.

The identification of a serine involved in mediating RNA cleavage is unexpected. Although mutation of His29 to alanine results in a catalytically inactive Csy4, mutation to lysine partially restores activity, strongly suggesting that His29 acts as a proton donor, not to initiate cleavage via a nucleophilic attack.

CRISPRs are the genetic memory of a nucleic acid-based immune system that relies on small CRISPR-derived RNAs for guiding the immune system to cognate sequences associated with invading genetic elements. Phylogenetic analysis of CRISPR repeat sequences has identified distinct CRISPR categories (Kunin, et al. *Genome Biol* 8, R61 (2007)) that correlate with a particular set of Cas genes. The co-variation of Cas genes with specific CRISPR repeat sequence types suggests that CRISPR repeats have co-evolved with the Cas genes that are responsible for CRISPR adaptation, the generation of crRNAs and the silencing of invading genetic elements. The structure described here details an unusual recognition mechanism that discriminates crRNA substrates based on both sequence- and structure-specificity, providing great insight into the ability of Csy4 and its homologues to readily distinguish substrate RNA from among all cellular RNAs.

FIGS. 1A-C. Pa14Csy4 specifically recognizes only its pre-crRNA substrate. a, Schematic of CRISPR/Cas locus in Pa14. The six Cas genes are flanked on both sides by CRISPR loci. Enlarged is a schematic showing the predicted stem-loop in the 28-nucleotide direct repeat (black lettering) separated by 32-nucleotide spacer sequences (blue). The red arrows note the bond cleaved by Csy4. b,c Comparison of protein (b) and RNA content (c) after Pa14Csy4 expression in *E. coli* with (+) and without (−) a plasmid containing a Pa14 CRISPR locus. Purified Csy4 from both preparations was split into two pools. Half were resolved on SDS-PAGE and visualized with Coomassie blue staining; half were acid phenol-chloroform extracted, resolved on UREA-PAGE, and visualized with SYBR Gold (Invitrogen).

Figure 2B:
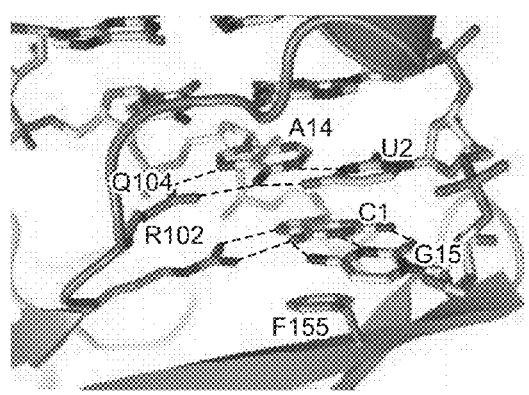
Figure 2C:
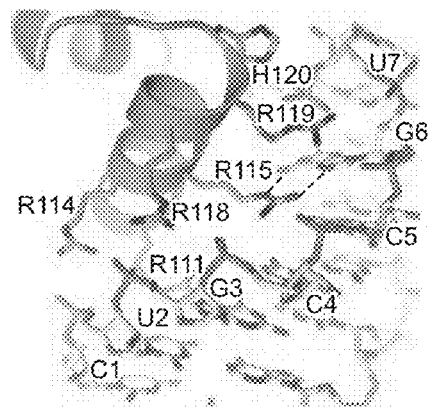

FIGS. 2A-C. The crystal structure of Csy4 bound to RNA substrate. a, Front and back views of the complex. Csy4 is colored in blue and the RNA backbone is colored in orange. b, Detailed interactions between residues R102 and Q104 and nucleotides A14 and G15. Hydrogen bonding is depicted with dashed lines. c, Detailed interactions between an arginine-rich alpha helix and the RNA backbone and G6.

FIGS. 3A and 3B. Putative active site. a, Detailed view of the catalytic center. b, Cleavage activity of Csy4. Wild-type (WT) Csy4 and a series of single point mutants were incubated with in vitro transcribed pre-crRNA for 5 minutes at 25 C. Products were acid phenol-chloroform extracted and resolved on UREA-PAGE and visualized by SYBR Gold staining.

Example 2

Direct RNA Sequencing

An RNA can be sequenced at the single-molecule level using Förster Resonant Energy Transfer (FRET). The RNA to be sequenced will be attached to a solid surface through its 3' ribose. The RNA should be spaced far enough from neighboring RNA molecules on the surface to allow detection at the single-molecule level. The spacing is dictated by diffraction-limited methods, dependent on the wavelength of emitted light. Alternatively, the RNA spacing can be closer than the diffraction limit, if super-resolution imaging methods are used. In the first sequence detection step, a Csy4 family protein of known nucleic acid binding specificity is added to the RNA to be sequenced, along with a pool of detection oligonucleotides. The Csy4 protein will only bind to the RNA to be sequenced if one of the detection oligonucleotides can form a 4 base pair double helix with the RNA to be sequenced. In addition, the detection nucleotide must base pair with an additional 3 nucleotides 3' of the 4 base pair recognition sequence in the RNA to be sequenced, in order for the Csy4 protein to bind stably. The detection oligonucleotides will contain an extension of 3 nucleotides 3' of the 4-nucleotide recognition sequence. In the pool of detection oligonucleotides, the 3-nucleotide extension will have a defined 5' nucleotide followed by two random nucleotide positions; or a random nucleotide at the 5' position followed by a defined nucleotide and a random nucleotide; or 2 random nucleotides at the 5' end, followed by a defined nucleotide. In any of these pools, the defined nucleotide is known based on an attached fluorescent molecule, the emission or excitation spectrum of which is defined by the nucleotide. The Csy4 protein will be attached to a quantum dot whose excitation spectrum overlaps with the emission spectrum of the fluorescent molecule attached to the detection oligonucleotide. After binding of detection oligonucleotides and Csy4, excess reagents will be washed away. A positive binding event is detected only if the detection nucleotide forms a 7-nucleotide double helix with the RNA to be sequenced. If binding occurs, the resulting ternary complex of RNA to be sequenced, detection oligonucleotide, and Csy4 protein can be detected by FRET from the fluorescent molecule attached to the detection oligonucleotide to the quantum dot attached to the Csy4 protein. After each cycle of binding, the Csy4 protein and detection oligonucleotides will be removed from the sample using chemical and/or heat denaturation and washing. In subsequent sequencing steps, other Csy4 proteins of different sequence specificity and their corresponding detection oligonucleotides will be incubated with the RNA to be sequenced, in a similar manner. Other variations of the 3-nucleotide extension on the detection oligonucleotide can be envisioned, such as extensions of different lengths, at either the 5' end or 3' end of the detection oligonucleotide. The detection oligonucleotide could be RNA, DNA, or any chemically modified version of these polymers, such as PNAs or LNAs.

Example 3

Inducible Sequence-Specific Endoribonuclease

Figure 8:
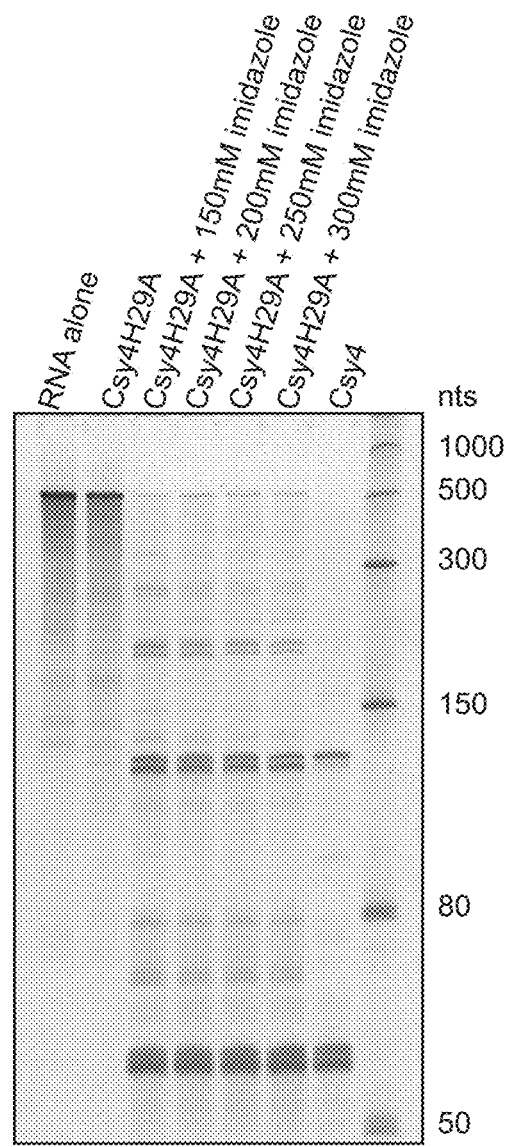
FIG. 8 depicts the effect of imidazole on activation of various enzymatically inactive Csy4 variants.

Via biochemical and structural techniques, point mutants of Csy4 that lack cleavage activity, while retaining substrate binding activity, have been generated. An example is the above-described Csy4(H29A) mutant. The otherwise catalytically inactive Csy4(H29A) mutant can be reactivated in the presence of exogenous imidazole. Addition of between 150 mM and 300 mM imidazole to the reaction buffer is sufficient to stimulate near-wild type cleavage activity. The results are shown in FIG. 8. FIG. 8 shows a cleavage activity assay depicting the imidazole rescue. Csy4H29A is a catalytically inactive mutant of Csy4 that retains the ability to bind its substrate with a kd of <1 nM.

Reaction details for FIG. 8: Each 10 µl reaction contains 5 pmol of the in vitro transcribed pre-crRNA substrate, 100 pmol of Csy4 (WT or H29A, as indicated in FIG. 8), 20 mM HEPES pH 7.5, 100 mM KCl, and 150-300 mM imidazole, as indicated. Reactions were carried out for 30 minutes at 25° C.) Products were acid phenol-chloroform extracted, separated on a 15% denaturing gel, and visualized with SYBR Gold. Biochemical characterization of Csy4(H29A) shows that it binds to its RNA substrate with <1 nM affinity.

FIG. 11 depicts additional examples of sequence-specific Csy4 endoribonucleases and mutant, inactive versions of these endoribonucleases that can be reactivated in the presence of imidazole. The residue to be mutated (His to Ala) is inferred from the conserved histidine (asterisk) revealed by the alignment depicted in FIG. 4. As a non-limiting example, FIG. 11D depicts that a corresponding H29A (His to Ala) mutation according to a sequence alignment such as that depicted in FIG. 4 (which can be readily determined by one of ordinary skill in the art for any Csy4 protein) can be H34A when generating an inactive version (that can be reactivated in the presence of imidazole) of Csy4 (SEQ ID NO: 109, Ala-34) from an active version of Csy4 (SEQ ID NO: 108, His-34) from, for example, *Acinetobacter* sp. ADP1.

The results are shown in FIG. 12. FIG. 12 shows results from five Csy4 enzymes that were mutated to generate active site His to Ala mutations: (A) Ec89, *Escherichia coli* UTI89; (B) Dn, *Dichelobacter nodosus*; (C) AA, *Acinetobacter* sp. ADP1; (D) SspW3, *Shewanella* sp. W3-18-1; and (E) Ab, *Acinetobacter baumannii*. Reaction details for FIG. 12: 75 pmol of wild-type or mutant proteins were incubated with 50 pmol of one or two of the RNA substrates (see FIG. 11) that co-occur with these protein sequences in the absence or presence of 300 mM imidazole in 20 µl reactions. Reactions were carried out at room temperature for 30 minutes (B,D) or 3 hours (A,C,E). Samples were phenol:chloroform extracted, separated on 20% denaturing gels, and stained with SYBR-Gold.

Csy4(H29A) is useful for both in vivo and in vitro applications for which there is no current alternative approach.

Csy4(H29A) or a corresponding variant as described above (also referred to herein as "inducible" Csy4), is useful for purifying a particular RNA/protein complex (RNP) from a complex mixture of RNAs and RNPs (RNA/protein complexes). For example, researchers may be interested in understanding which proteins bind to a particular RNA transcript. Using this system, the researchers could engineer an expression construct for their RNA of choice that would include a 5' tag consisting of the stem-loop Csy4 target sequence. The researchers would then transfect this expression construct into their cell type of choice, leading to the generation of many RNAs and RNPs. Cells would then be lysed and the lysate would be applied to a column that contains inducible Csy4 immobilized on agarose beads. RNAs or RNPs that have the Csy4 target sequence will bind. A subsequent wash step will remove non-specifically bound RNAs. A wash with imidazole (~300 mM) will activate inducible Csy4, which will cleave the target sequence and release the bound RNA/RNP. This method is illustrated schematically in FIG. 9.

A similar method could be useful for assembling RNPs in vitro. For example, an RNA of choice could be transcribed in vitro using a construct similar to the expression plasmid designed for the above experiment. (The construct must introduce the Csy4 stem-loop target sequence at the 5' end of the transcribed RNA.) This in vitro transcribed product could then be incubated with proteins known or suspected to bind the particular transcript. The inducible Csy4-containing column could be used to purify the in vitro formed RNPs away from free protein.

Example 4

The mechanism for specific substrate recognition by the endoribonuclease CasE, an essential component of the CRISPR immune system found in the majority of bacteria and archaea (van der Oost et al., *Trends Biochem Sci.* 34, 401-7 (2009)) has been determined. Using structural and biochemical methods, the minimal RNA sequence required for optimal substrate cleavage, a 20 nucleotide sequence (5-24 of CRISPR repeat sequence) that includes a seven base-pair stem-loop followed by two unpaired nucleotides, was identified. The structure of this RNA bound to CasE from *Thermus thermophilus* was solved at 2.0 Å resolution using X-ray crystallography. This structure reveals numerous sequence specific contacts between the protein and RNA, including several interactions in the major groove of the RNA. The terminal base-pair in the stem-loop in disrupted, with A22 flipped out of the helix and base-stacked with U23. This conformation is partially stabilized by interactions with S34 and E38, which also confer sequence specificity for substrate recognition. Further stabilization of the A22 and U23 conformation is achieved by positioning of the terminal nucleotide, G24, which flips back into register with the stem-loop, but resides well below the helix in a binding pocket made up of residues D18, E24, and K31, with R27 contacting the backbone between U23 and G24.

The positioning of A22 elongates the backbone of the RNA at the scissile phosphate, splaying it between two active site residues, Y23 and H26. Based on this observation, and the apparent stabilization of this RNA conformation by G24 binding, it was hypothesized that G24 may be required for positioning the RNA in a catalytic conformation. Consistent with this hypothesis, deletion or mutation of G24 significantly reduces cleavage activity, as does mutations of protein residues involved in G24 binding. To confirm the role of G24 in inducing the catalytic RNA conformation, the structure of CasE bound to a 19 nucleotide RNA that lacked the terminal G24 residue was determined. This complex crystallized in two different forms, which revealed two different RNA conformations at the active site of the protein. In one crystal form (P2$_1$), the 2.5 Å structure contained 8 molecules in the asymmetric unit. All 8 molecules revealed that A22 base stacks with G21, maintaining A-form geometry with the rest of the stem-loop. In addition to the changes in the RNA structure, the protein structure also differs from the catalytic conformation observed in the 2.0 Å structure. In that structure, a loop containing R158 and K160 is juxtaposed with the active site, suggesting that these residues may play a role in catalysis and/or in stabilization of a transition-state intermediate. In the 2.5 Å structure, this loop is distal from the active site and partially disordered, suggesting that the positioning of the loop is flexible. Interestingly, this loop is also disordered in the apo structure of CasE (Ebihara et al., Protein Sci. 15, 1494-9 (2006)), suggesting that the correct RNA conformation is required for stabilization of this loop.

The second crystal form (P2$_1$2$_1$2$_1$) obtained for the CasE/ 19-nucleotide RNA complex was used to determine a 1.5 Å structure, which revealed the RNA bound in the catalytic conformation with A22 and U23 flipped out of the helix. However, the loop containing R158 and K160 remains disordered in this structure, suggesting that G24 binding may also be required for stabilization of this protein structure. The observation of two different RNA conformations for the same complex suggests that the RNA may sample several structural states, and that it may require G24 to lock it into the catalytically competent conformation.

Example 5

FIG. 13 illustrates that Csy4 endoribonuclease from a given species can cleave RNA substrates from various other species with rate constants that are either greater or less than that achieved when cleaving a cognate (from the same species) RNA substrate. (A) In vitro cleavage reactions were carried out with each of six Csy4 variants paired with either its own cognate RNA(s) or one of the variant RNA sequences. All RNA substrates used in this experiment were the long form. For protein and RNA sequences, see FIGS. 11A-G) (Pa14, *Pseudomonas aeruginosa*; Ec89, *Escherichia coli* UTI89; Dn, *Dichelobacter nodosus*; AA, *Acinetobacter* sp. ADP1; Ab, *Acinetobacter baumannii*; MM, *Marinomonas* sp. MWYL1; and SspW3, *Shewanella* sp. W3-18-1). Values shown are the reaction rate constant (per minute). Reactions contained 50 nM Csy4, 0.1-1 nM RNA, 20 mM HEPES, 100 mM KCl, and 1 mM DTT at pH$_{RT}$ 7.5. (B) Rates are normalized for each Csy4 homolog tested in FIG. 11, such that the largest rate constant in each row is defined as 100%.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An in vitro method of regulating production of a target RNA from a precursor RNA in a eukaryotic cell, the method comprising:

introducing into said eukaryotic cell a recombinant expression vector comprising a nucleotide sequence encoding an enzymatically active sequence-specific Csy4 endoribonuclease, wherein the Csy4 endoribonuclease comprises an amino acid sequence having at least 95% amino acid sequence identity to the amino acid sequence set forth in SEQ ID NO:8, wherein the target RNA comprises a GUUCACUGCCGUAUAG-GCAG (SEQ ID NO:103) cleavage site in the 3' untranslated region of a precursor RNA comprising the target RNA, and wherein said Csy4 endoribonuclease is produced in the cell and cleaves said target RNA from the precursor RNA at the cleavage site, thereby regulating production of the target RNA.

2. The method of claim 1, wherein the target RNA species is a regulatory RNA.

3. The method of claim 1, wherein cleavage of said target RNA from a precursor RNA inactivates the precursor RNA.

4. The method of claim 1, wherein said nucleotide sequence encoding an enzymatically active sequence-specific Csy4 endoribonuclease is operably linked to a promoter.

5. The method of claim 4, wherein said method comprises contacting the promoter with an agent that activates said promoter.

6. The method of claim 4, wherein said cleaving of said target RNA from said precursor RNA inactivates said target RNA.

7. The method of claim 4, wherein said cleaving of said target RNA from said precursor RNA reduces expression levels of said target RNA.

8. The method of claim 4, wherein said precursor RNA comprises a poly-A tail.

9. The method of claim 4, wherein the Csy4 endoribonuclease comprises an amino acid sequence having at least 98% amino acid sequence identity to the amino acid sequence set forth in SEQ ID NO: 8.

10. The method of claim 4, wherein the Csy4 endoribonuclease comprises a moiety that provides a detectable signal.

11. The method of claim 10, wherein the moiety is a fluorophore, a quantum dot, an enzyme other than the endoribonuclease, or a nanoparticle.

12. The method of claim 4, wherein the Csy4 endoribonuclease binds an RNA substrate comprising the nucleotide sequence 5'-GUUCACUGCCGUAUAGGCAGC-UAAGAAA-3' (SEQ ID NO: 1).

13. The method of claim 4, wherein said eukaryotic cell is a primary cell.

14. The method of claim 4, wherein said eukaryotic cell is a mammalian cell.

* * * * *

UNITED STATES PATENT AND TRADEMARK OFFICE
CERTIFICATE OF CORRECTION

PATENT NO.         : 9,605,246 B2
APPLICATION NO.    : 14/735383
DATED              : March 28, 2017
INVENTOR(S)        : Rachel E. Haurwitz et al.

It is certified that error appears in the above-identified patent and that said Letters Patent is hereby corrected as shown below:

In the Specification

The following text should replace the paragraph titled "STATEMENT REGARDING FEDERALLY SPONSORED RESEARCH" of Column 1:
--STATEMENT REGARDING FEDERALLY SPONSORED RESEARCH
This invention was made with government support under Grant No. T32 GM007232 awarded by the National Institutes of Health and Grant No. 0950971 awarded by the National Science Foundation. The government has certain rights in the invention.--

Signed and Sealed this
Ninth Day of May, 2017

Michelle K. Lee
*Director of the United States Patent and Trademark Office*